(12) United States Patent
McDevitt et al.

(10) Patent No.: US 7,645,752 B2
(45) Date of Patent: Jan. 12, 2010

(54) SULFONYL SUBSTITUTED 1H-INDOLES AS LIGANDS FOR THE 5-HYDROXYTRYPTAMINE RECEPTORS

(75) Inventors: Robert E. McDevitt, Freehold, NJ (US); Yanfang Li, Lawrenceville, NJ (US); Albert J. Robichaud, Ringoes, NJ (US); Gavin D. Heffernan, Florence, NJ (US); Richard D. Coghlan, Phoenixville, PA (US); Ronald C. Bernotas, Royersford, PA (US)

(73) Assignee: Wyeth LLC, Madison, NJ (US)

( * ) Notice: Subject to any disclaimer, the term of this patent is extended or adjusted under 35 U.S.C. 154(b) by 28 days.

(21) Appl. No.: 11/622,649

(22) Filed: Jan. 12, 2007

(65) Prior Publication Data

US 2007/0203120 A1 Aug. 30, 2007

Related U.S. Application Data

(60) Provisional application No. 60/758,833, filed on Jan. 13, 2006.

(51) Int. Cl.
| | |
|---|---|
| A61K 31/404 | (2006.01) |
| A61K 31/454 | (2006.01) |
| A61K 31/55 | (2006.01) |
| A61K 31/10 | (2006.01) |
| C07D 403/02 | (2006.01) |
| C07D 209/30 | (2006.01) |
| C07C 317/32 | (2006.01) |

(52) U.S. Cl. .................. 514/217.08; 514/418; 514/419; 514/323; 514/414; 514/709; 540/602; 544/111; 546/201; 548/469; 548/484; 548/950

(58) Field of Classification Search .................. 514/418, 514/235.2, 422, 323, 218, 210.2, 419, 709, 514/217.9; 540/602; 544/111; 546/201; 548/484, 518, 950, 469
See application file for complete search history.

(56) References Cited

U.S. PATENT DOCUMENTS

| | | | |
|---|---|---|---|
| 5,132,319 A | 7/1992 | Girard et al. |
| 5,190,968 A | 3/1993 | Gillard et al. |
| 5,273,980 A | 12/1993 | Frerette et al. |
| 5,290,798 A | 3/1994 | Gillard et al. |
| 5,308,850 A | 5/1994 | Gillard et al. |
| 5,418,242 A | 5/1995 | Bru-Magniez et al. |
| 5,464,861 A | 11/1995 | Dobrusin et al. |
| 5,482,960 A | 1/1996 | Berryman et al. |
| 5,532,237 A | 7/1996 | Gallant et al. |
| 5,556,874 A | 9/1996 | Dobrusin et al. |
| 5,567,711 A | 10/1996 | Sheppard et al. |
| 5,654,305 A | 8/1997 | Sheppard et al. |
| 5,686,481 A | 11/1997 | Elliott et al. |
| 5,840,738 A | 11/1998 | Bell et al. |
| 5,905,070 A | 5/1999 | Schinazi et al. |
| 6,075,037 A | 6/2000 | Elliott et al. |
| 6,207,687 B1 | 3/2001 | Claiborne et al. |
| 6,214,834 B1 | 4/2001 | Jadhav et al. |
| 6,232,300 B1 | 5/2001 | Schinazi et al. |
| 6,239,159 B1 | 5/2001 | Brown et al. |
| 6,251,923 B1 | 6/2001 | Höfgen et al. |
| 6,265,581 B1 | 7/2001 | Bell et al. |
| 6,303,600 B1 | 10/2001 | Cox et al. |
| 6,391,859 B1 | 5/2002 | Schinazi et al. |
| 6,500,853 B1 | 12/2002 | Seehra et al. |
| 6,545,025 B2 | 4/2003 | Hofgen et al. |
| 6,545,158 B2 | 4/2003 | Hofgen et al. |
| 6,552,042 B2 | 4/2003 | Han et al. |
| 6,579,879 B2 | 6/2003 | Mylari et al. |
| 6,602,890 B2 | 8/2003 | Hofgen et al. |
| 6,613,794 B2 | 9/2003 | Hofgen et al. |
| 6,710,068 B2 | 3/2004 | LaColla et al. |
| 6,800,645 B1 | 10/2004 | Cox et al. |
| 6,927,291 B2 | 8/2005 | Jin et al. |
| 2002/0083126 A1 | 6/2002 | Best et al. |
| 2003/0101990 A1 | 6/2003 | Pllach et al. |
| 2003/0162784 A1 | 8/2003 | Mylari et al. |
| 2003/0176421 A1 | 9/2003 | Watson et al. |
| 2003/0195244 A1 | 10/2003 | Hsieh et al. |
| 2004/0009990 A1 | 1/2004 | Higgins et al. |
| 2004/0038958 A1 | 2/2004 | Rundfeldt et al. |

(Continued)

FOREIGN PATENT DOCUMENTS

DE 19818964 11/1999

(Continued)

OTHER PUBLICATIONS

U.S. Appl. No. 11/605,525, Lyer et al.*

(Continued)

*Primary Examiner*—Yong Chu
(74) *Attorney, Agent, or Firm*—Doina G. Ene; Scott Larsen

(57) ABSTRACT

The present invention is directed to compounds of Formula I:

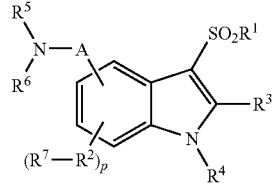

which are modulators of the 5-hydroxtryptamine-6 and 5-hydroxytryptamine-2A receptors and which are inhibitors of norepinephrine reuptake. The compounds of the invention, and pharmaceutical composition thereof, are useful in the treatment of disorders related to or associated with the 5-hydroxytryptamine-6 and 5-hydroxytryptamine-2A receptors or with norepinephrine reuptake inhibition.

29 Claims, No Drawings

U.S. PATENT DOCUMENTS

| | | | |
|---|---|---|---|
| 2004/0087593 A1 | 5/2004 | Clark et al. |
| 2004/0102360 A1 | 5/2004 | Barnett et al. |
| 2004/0132799 A1 | 7/2004 | Zhao |
| 2004/0138286 A1 | 7/2004 | Imazaki et al. |
| 2004/0162784 A1 | 8/2004 | Tadayon et al. |
| 2004/0167030 A1 | 8/2004 | Bernotas et al. |
| 2004/0167122 A1 | 8/2004 | Bernotas et al. |
| 2004/0180945 A1 | 9/2004 | Artico et al. |
| 2004/0242589 A1 | 12/2004 | Bromidge et al. |
| 2005/0153980 A1 | 7/2005 | Schadt et al. |
| 2006/0128722 A1 | 6/2006 | Hermkens et al. |
| 2007/0037802 A1 | 2/2007 | Elokdah et al. |
| 2007/0123527 A1 | 5/2007 | Iyer et al. |

FOREIGN PATENT DOCUMENTS

| | | |
|---|---|---|
| DE | 19846514 | 4/2000 |
| EP | 0345747 | 12/1989 |
| EP | 0535923 | 4/1993 |
| EP | 0535924 | 4/1993 |
| EP | 535925 | 4/1993 |
| EP | 535926 | 4/1993 |
| EP | 562832 | 9/1993 |
| EP | 639573 | 2/1995 |
| EP | 639753 | 2/1995 |
| EP | 937459 | 8/1999 |
| EP | 1040829 | 10/2000 |
| GB | 2309969 | 8/1997 |
| JP | 3257054 | 11/1991 |
| JP | 2006/269128 | 10/2006 |
| WO | WO 93/01169 | 1/1993 |
| WO | WO 93/25546 | 12/1993 |
| WO | WO 94/03427 | 2/1994 |
| WO | WO 94/14434 | 7/1994 |
| WO | WO 95/16687 | 6/1995 |
| WO | WO 95/33748 | 12/1995 |
| WO | WO 96/33196 | 10/1996 |
| WO | WO 97/04998 | 2/1997 |
| WO | WO 97/23480 | 7/1997 |
| WO | WO 97/48697 | 12/1997 |
| WO | WO 97/49698 | 12/1997 |
| WO | WO 98/43962 | 10/1998 |
| WO | WO 99/07678 | 2/1999 |
| WO | WO 99/12903 | 3/1999 |
| WO | WO 99/23076 | 5/1999 |
| WO | WO 99/23077 | 5/1999 |
| WO | WO 93/16069 | 8/1999 |
| WO | WO 99/43654 | 9/1999 |
| WO | WO 99/54295 | 10/1999 |
| WO | WO 99/55696 | 11/1999 |
| WO | WO 00/46169 | 1/2000 |
| WO | WO 00/12073 | 3/2000 |
| WO | WO 00/21954 | 4/2000 |
| WO | WO 00/78310 | 12/2000 |
| WO | WO 01/05758 | 1/2001 |
| WO | WO 01/32621 | 5/2001 |
| WO | WO 02/11765 | 2/2002 |
| WO | WO 02/051849 | 7/2002 |
| WO | WO 02/060900 | 8/2002 |
| WO | WO 02/076926 | 10/2002 |
| WO | WO 02/79165 | 10/2002 |
| WO | WO 02/083126 | 10/2002 |
| WO | WO 02/098857 | 12/2002 |
| WO | WO 02/100833 | 12/2002 |
| WO | WO 03/013510 | 2/2003 |
| WO | WO 03/024969 | 3/2003 |
| WO | WO 03/041644 | 5/2003 |
| WO | WO 03/051277 | 6/2003 |
| WO | WO 03/053989 | 7/2003 |
| WO | WO 03/063771 | 8/2003 |
| WO | WO 03/083488 | 10/2003 |
| WO | WO 03/087086 | 10/2003 |
| WO | WO 03/101961 | 12/2003 |
| WO | WO 03/101962 | 12/2003 |
| WO | WO 03/101990 | 12/2003 |
| WO | WO 2004/006920 | 1/2004 |
| WO | WO 2004/007451 | 1/2004 |
| WO | WO 2004/009548 | 1/2004 |
| WO | WO 2004/009600 | 1/2004 |
| WO | WO 2004/014364 | 2/2004 |
| WO | WO 2004/014851 | 2/2004 |
| WO | WO 2004/035036 | 4/2004 |
| WO | WO 2004/035047 | 4/2004 |
| WO | WO 2004/041782 | 5/2004 |
| WO | WO 2004/050085 | 6/2004 |
| WO | WO 2004/069797 | 8/2004 |
| WO | WO 2004/102360 | 11/2004 |
| WO | WO 2005/035506 | 4/2005 |
| WO | WO 2005/055955 | 6/2005 |
| WO | WO 03/062784 | 7/2005 |
| WO | WO 2007/062996 | 6/2007 |

OTHER PUBLICATIONS

U.S. Appl. No. 60/741,266.*
Cited ref_STN_search_11622649.*
International Search Report for International Application No. PCT/US2007/060454, Jul. 9, 2007.
Bentley, J.C., et al., "Investigation of stretching behaviour induced by the selective 5-HT6 receptor antagonist, Ro 04-6790, in rats", *British Journal of Pharmacology*, 126(7):1537-1542 (1999).
Branchek, T.A., et al., "5-ht6 receptors as emerging targets for drug discovery", *Annual Reviews in Pharmacology and Toxicology*, 40: 391-334 (2000).
Berendsen, H.H., The role of serotonin in hot flashes:, *Maturitas*, 36(3): 155-64, 2000.
Biegon, A., Effects of steroid hormones on the serotonergic system. In: Whitaker-Asmitia, P.M.; Peroutka S.J., editors, *The Neuropharmacology of Serotonin*, 600: 427-34, 1990.
Bioreversible Carriers in Drug Design, ed. Edward B. Roche, American Pharmaceutical Association and Pergamon Press, 1987.
De Angelis, L., "5-HT2A antagonists in psychiatric disorders", *Current Opinion in Investigational Drugs*, 3(1):106-12, 2002.
Doggrell, S.A., "The role of 5-HT on the cardiovascular and renal systems and the clinical potential of 5-HT modulation", *Expert Opinion on Investigational Drugs*, 12(5):805-23, 2003.
Dawson, L.A., et la., "In vivo effects of the 5-HT(6) antagonist SB-271046 on striatal and frontal cortex extracellular concentrations of noradrenaline, dopamine, 5-HT, glutamate and aspartate", *British Journal of Pharmacology*, 130(1):23-26, 2000.
Eliel, E.L., Steriochemistry of Carbon Compounds (McGraw Hill, NY, 1962).
Ernst, M., et al., "DOPA decarboxylase activity in attention deficit hyperactivity disorder adults. A [fluorine-18]fluorodopa positron emission tomographic study", *Journal of Neuroscience*, 18(15):5901-5907, 1998.
Fink, G., et al., "Oestrogen and mental state", *Nature*, 383(6598):306, 1996.
Greene, et al., Protective Groups in Organic Synthesis, $2^{nd}$ ed., Wiley and Sons, 1991.
Gerard, C., et al, Immuno-localization of serotonin 5-HT6 receptor-like material in the rat central nervous system, Brain Research, 746(1-2):207-219, 1997.
Garcia, J., et al., "A novel synthesis of 3-cyanoindoles and a new route to indole-3-carboxylic acid derivatives", *Tetrahedron Letters*, 26:1827-1830, 1985.
Higuchi, T. and Stellla V, eds., Pro-drugs as Novel Delivery System, vol. 14 of the A.C.S. Symposium Series, American Chemical Society, 1975.
Jain, S., et al., "The Reaction of Acyloxysulfonium Salt with Cyclic Enol Ethers: Novel Synthesis of Vinyl.Sulfides", *Synthetic Communication*, 20:1315-1320, 1990.
*Journal of Pharmaceutical Science*, 66:2 , 1997.

Jacques, et al., "Enantiomers, racemates and resolutions" (Wiley Interscience, New York, 1981).

Kohen, R., et al, "Coning, characterizations, and chromosomal localization of a human 5-HT6 serotonin receptor", *Journal of Neurochemistry*, 66(1):47-56, 1996.

Kardos, N., et al., "Synthesis of (−)-chanoclavine I", *Tetrahedron:Asymmetry*, 5:1525-1533, 1994.

Lowry, et al., "Protein measurement with the Folin phenol reagent", *J. Biol. Chem.*, 193:265-75, 1951.

Leysen, E. et al, "5-HT2 Antagonists: a Concept for the Treatment of Schizophrenia", *Current Pharmaceutical Design*, 3:367, 1997.

Monsma, F.J., et al, "Cloning and expression of a novel serotonin receptor with high affinity for tricyclic psychotropic drugs", *Molecular Pharmacology*, 43:320-327, 1993.

Meltzer, H.H., "The role of serotonin in antipsychotic drug action", *Neuropsychopharmacology*, 21: 106S, 1999.

Mazzola-Pomietto, P., et al., "Evidence that 1-(2,5-dimethoxy-4-iodophenyl)-2-amineopropane (DOI)-induced hyperthermia in rats is mediated by stimulation of 5-HT2A receptors", *Psychopharmacology*, 117(2):193-09, 1995.

M.H. Beers, et al., The Merck Manual of Diagnosis and Treatment, section 3 (17$^{th}$ ed. John Wiley and Sons, 1999).

M.H. Beers, et al., The Merck Manual of Diagnosis and Treatment, section 17 (17$^{th}$ ed. John Wiley and Sons, 1999).

Makosza, M., et al., "Synthesis of a 1,3,4,5-tetrahydrobenz [cd] indole via the vicarious nucleophilic substitution of hydrogen", *Tetrahedron*, 53(1): 192-214, 1997.

Nishiyama, T., "Effects of a 5-HT$_{2A}$ receptor antagonist, sarpogrelate on thermal or inflammatory pain", *European Journal of Pharmacology*, 516:18, 2005.

Nitanda, A., et al., "Contribution of the peripheral 5-HT 2A receptor to mechanical hyperalgesia in a rat model of neuropathic pain", *Neurochemistry International*, 47(6):394-400, 2005.

Nisijima, K., Potent serotonin (5-HT)(2A) receptor antagonists completely prevent the development of hyperthermia in an animal model of the 5-HT syndrome:, *Brain Research*, 890:23-31, 2001.

Pacholczyk, T., et al., "Expression cloning of a cocaine-and antidepressant-sensitive human noradrenaline transporter", *Nature*, 350(6316):350-4, 1991.

Ruat, M., et al., "A novel rat serotonin (5-HT6) receptor: molecular cloning, localization and stimulation of cAMP accumulation", *Biochemical Biophysical Research Communications*, 193(1):268-276, 1993.

Rogers, D.C., "The Selective 5HT6 Receptor Antagonist, SB-271046-A, Enhances Performance of Maze Tasks in the Rat", *Society of Neuroscience, Abstracts 2000*, 26:680.10.

Routledge, C., et al., "Characterization of SB-271046: a potent, selective and orally active 5-HT(6) receptor antagonist", *British Journal of Pharmacology*, 130(7):1606-1612. 2000.

Roberts, J.C., et al., "Autoradiographic Localisation of the 5-HT2 Receptor in the CNS of the Rat Using [???]SB-239595", *British Journal of Pharmacology*, 128:156P, 2000.

Orlemans, E.O.M., et al., "Synihesis of 3-substituted indoles via a modified madeling reaction", *Tetrahdedron Letters*, 43:3817-3826, 1987.

*Remington's Pharmaceutical Sciences*, 17$^{th}$ ed., Mack Publishing Company, Easton, PA., p. 1418,1985.

Stean, T., et al., "Anticonvulsant Properties of the Selective 5-HT2 Receptor Antagonist SB-271046 in the Rat Maximal Electroshock Seizure Thrreshold Test", *British Journal of Pharmacology*, 127 Suppl: 1P-143P, 1999 (Proceedings of the British Pharmacological Society Meetings, joint meeting with the Portuguese Society of Pharmacolaogy, Abstracts.

Woolley, M.L., et al., "Reversal of a cholinergic-induced deficit in a rodent model of recognition memory by the selective 5-HT6 receptor antagonist, RO 04-6790", *Psychopharmacology*, 170(4): 358-367, 2003. (Abstract only).

Ward, R.P., et al., "Localization of serotonin subtype 6 receptor messenger RNA in the rat brain by in situ hybridization histochemistry", *Neuroscience*, 64(4):1105-1111, 1995.

Waldinger, M.D., et al., "Treatment of hot flushes with mirtazapine: four case reports", *Maturitas*, 36(3):165-8, 2000.

Wilen, S.H., et al., "Strategies in Optical Resolutions", *Tetrahedron*, 33:2725, 1977.

Wilen, S.H., Tables of Resolving Agents and Optical Resolutions, 268 (E.L. Eliel, Ed., Univ. of Notre Dame Press, Notre Dame, IN, 1972).

Wojciechowski, K., et al., "A Facile Synthesis of 3-Sulfonyl-Substituted Indole Derivatives", *Synthesis*, 651-653, 1986.

Zhou, J., "Norepinephrine transporter inhibitors and their therapeutic potential", *Drugs of the Future*, 29(12):1235-1244, 2004.

Tagaki, S., et al., Mianserin Hydrochloride, *Sanfujinka No Sekai (World Obstet Gynecol)*, 36:853, 1986.

Wermuth, C.G., "Molecular Variations Based on Isosteric Replacements", *Practice of Medicinal Chemistry*, 203-237, 1996.

Grinev, A.N., et al., "Reaction of 5-hydroxyindole derivatives with o-nitrophenylsulfenyl chloride", *Khimiya Getarotsiklicheskikh Soedinenii*, (2):220-03, 1974.

Mills, D., et al., Decision on Appeal 2006-0690, Sep. 26, 2006.

* cited by examiner

SULFONYL SUBSTITUTED 1H-INDOLES AS LIGANDS FOR THE 5-HYDROXYTRYPTAMINE RECEPTORS

This application claims benefit of priority of U.S. Provisional Application Ser. No. 60/758,833, filed Jan. 13, 2006, which is hereby incorporated by reference in its entirety.

FIELD OF THE INVENTION

The present invention is directed to compounds that are modulators of the 5-hydroxytryptamine-6 receptor, pharmaceutical compositions thereof, and methods of using the same. The present invention is also directed to compounds that are modulators of the 5-hydroxytryptamine-2A receptor, pharmaceutical compositions thereof, and methods of using the same. The present invention is also directed to compounds that are norepinephrine reuptake inhibitors, pharmaceutical compositions thereof, and methods of using the same.

BACKGROUND OF THE INVENTION

Serotonin (5-hydroxytryptamine) (5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the $5\text{-HT}_6$ receptor, first cloned from rat tissue in 1993 (Monsma, F. J.; Shen, Y.; Ward, R. P.; Hamblin, M. W. *Molecular Pharmacology* 1993, 43, 320-327, incorporated herein by reference in its entirety) and subsequently from human tissue (Kohen, R.; Metcalf, M. A.; Khan, N.; Druck, T.; Huebner, K.; Sibley, D. R. *Journal of Neurochemistry* 1996, 66, 47-56, both of which are incorporated herein by reference in their entireties). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276, incorporated herein by reference in its entirety) The receptor is found almost exclusively in the central nervous system (CNS) areas both in rat and in human. In situ hybridization studies of the $5\text{-HT}_6$ receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111, incorporated herein by reference in its entirety).

There are many potential therapeutic uses for $5\text{-HT}_6$ ligands in humans based on direct effects and on indications from available scientific studies. These studies include the localization of the receptor, the affinity of ligands with known in vivo activity, and various animal studies conducted so far.

One potential therapeutic use of modulators of $5\text{-HT}_6$ receptor function is in the enhancement of cognition and memory in human diseases such as Alzheimer's disease. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research,* 1997, 746, 207-219, incorporated herein by reference in its entirety). The ability of known $5\text{-HT}_6$ receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology,* 1999, 126(7), 1537-1542, incorporated herein by reference in its entirety). Studies have found that a known $5\text{-HT}_6$ selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for $5\text{-HT}_6$ ligands in cognition (Dawson, L. A.; Nguyen, H. Q.; Li, P. *British Journal of Pharmacology,* 2000, 130(1), 23-26, incorporated herein by reference in its entirety). Animal studies of memory and learning with a known selective $5\text{-HT}_6$ antagonist found some positive effects (Rogers, D. C.; Hatcher, P. D.; Hagan, J. J. *Society of Neuroscience, Abstracts* 2000, 26, 680, incorporated herein by reference in its entirety). Further support for the role of a selective $5\text{-HT}_6$ ligand in cognition can be found in Woolley, M. L.; Marsden, C. A.; Sleight, A. J.; and Fone, K. C. F., *Psychopharmacology,* 2003, 170(4), 358-367, incorporated herein by reference in its entirety.

A related potential therapeutic use for $5\text{-HT}_6$ ligands is the treatment of attention deficit disorders (ADD, also known as Attention Deficit Hyperactivity Disorder or ADHD) in both children and adults. Because $5\text{-HT}_6$ antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907, incorporated herein by reference in its entirety), $5\text{-HT}_6$ antagonists may attenuate attention deficit disorders.

Early studies examining the affinity of various CNS ligands with known therapeutic utility or a strong structural resemblance to known drugs suggests a role for $5\text{-HT}_6$ ligands in the treatment of schizophrenia and depression. For example, clozapine (an effective clinical antipsychotic) has high affinity for the $5\text{-HT}_6$ receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334, incorporated herein by reference in its entirety).

Further, recent in vivo studies in rats indicate $5\text{-HT}_6$ modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612, each of which is incorporated herein by reference in its entirety).

Taken together, the above studies strongly suggest that compounds which are $5\text{-HT}_6$ receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Another of the 5-hydroxytryptamine receptors, the $5\text{-HT}_{2A}$ receptor, has also been found to be important in a number of areas, including the regulation of the cardiovascular and central nervous systems, and the control of body temperature and vasomotor symptoms. Consistent with this receptor's involvement with regulation of the central nervous system, modulators of the 5-HT$_{2A}$ receptor may be beneficial in the treatment of neurological conditions such as schizophrenia, tardive dyskinesia, depression, suicidality, anxiety, panic disorder, obsessive-compulsive disorder, sleep disorders such as insomnia, eating disorders such as anorexia nervosa and dependency or acute toxicity associated with certain psychotomimetic agents such as LSD or MDMA (de Angelis, L. *Current Opinion in Investigational Drugs* 2002, 3(1), 106; Meltzer, H. Y. *Neuropsychopharmacolgy* 1999, 21, 106S; Leysen, D.; Linders, J. T. M.; Ottenheijm, H. C. J. *Current Pharmaceutical Design* 1997, 3, 367, each of which is incorporated herein by reference in its entirety). Additionally, recent in vivo studies also have suggested the use of 5-HT$_{2A}$ modulators for treating inflammatory or neuropathic pain (Nishiyama T. *European Journal of Pharmacology* 2005, 516, 18; Nitanda, A.; Yasunami, N.; Tokumo, K.; Fujii, H.; Hirai, T.; Nishio, H. *Neurochemistry International* 2005, 47(6), 394, each of which is incorporated herein by reference in its entirety).

In addition to its importance to the nervous system, the 5-HT$_{2A}$ receptor is also found in the cardiovascular system. Hence, compounds with 5-HT$_{2A}$ modulatory activity have benefit for the prophylaxis or treatment of cardiovascular conditions including coronary artery disease, myocardial infarction, transient ischemic attack, angina, atrial fibrillation, reducing platelet aggregation and reducing the risk of blood clot formation. (Doggrell, S. A. *Expert Opinion on Investigational Drugs* 2003, 12(5), 805, incorporated herein by reference in its entirety).

Additionally, recent reports have identified a function for the 5-HT$_{2A}$ receptor in temperature regulation (Mazzola-Pomietto, P.; Aulakh, C. S.; Wozniak, K. M.; Hill J. L.; Murphy, D. L. *Psychopharmacolgy* 1995, 117, 193, incorporated herein by reference in its entirety). Accordingly, 5-HT$_{2A}$ receptor antagonists have been effective in preventing the development of hyperthermia in animal models of serotonin syndrome (Nisijima, K.; Yoshino, T.; Yui, K.; Katoh, S. *Brain Research* 2001, 890, 23, incorporated herein by reference in its entirety).

Further, it has been hypothesized that the 5-HT$_{2A}$ receptor plays a key role in the occurrence of hot flushes and night sweats following menopause (Berendsen H. H. G., *Maturitas*, 2000, 36, 155, incorporated herein by reference in its entirety). Studies have shown that a low blood estrogen level correlates with a high concentration of the 5-HT$_{2A}$ receptor subtype on blood platelets (Biegon, A. Effects of steroid hormones on the serotonergic system. In: Whitaker-Azmitia, P. M.; Peroutka S. J. editors. *The Neuropharmacology of Serotonin*. 1990, 427-34, incorporated herein by reference in its entirety) and an upregulation of central 5-HT$_{2A}$ receptors (Fink G.; Sumner B. E. H. *Nature*, 1996, 383, 306, incorporated herein by reference in its entirety). The 5-HT$_{2A}$ and 5-HT$_{2C}$ receptor antagonist, mirtazapine, was effective in reducing the frequency and intensity of hot flushes (Waldinger M. D.; Berendsen, H. H. G.; Schweitzer, D. H. *Maturitas*, 2000, 36, 165, incorporated herein by reference in its entirety). Similarly, the 5-HT$_{2A}$ receptor antagonist mianserin also had efficacy in treating hot flushes (Takagi S.; Yanagisawa, Y. *Sanfujinka No Sekai* (*World Obstet Gynecol*) 1986, 36, 853, incorporated herein by reference in its entirety). It has also been reported that the combination of a norepinephrine reuptake inhibitor with a 5-HT$_{2A}$ receptor antagonist results in enhanced activity in animal models of thermoregulatory dysfunction (Deecher D. C.; Merchenthaler, I. J. WO 2004/035036, incorporated herein by reference in its entirety).

Besides the attention in the scientific community to modulators of the 5-HT receptors, there is also a growing interest in developing new inhibitors of the norepinephrine reuptake. It has been hypothesized that norepinephrine reuptake inhibitors have benefit in the treatment of conditions associated with norepinephrine dysfunction and include, for example, vasomotor symptoms (VMS), major depressive disorder, sexual dysfunction, gastrointestinal and genitourinary disorders, chronic fatigue syndrome, fibromyalgia syndrome, diabetic neuropathy, nervous system disorders, and stress and urge urinary incontinence, attention deficit disorder, and pain including chronic pain, neuropathic pain and antinociceptive pain. (Zhou, J. *Drugs of the Future* 2004, 29(12), 1235, incorporated herein by reference in its entirety).

Due to the large number of people afflicted by the disorders related to the 5-HT$_6$ and 5-HT$_{2A}$ receptors and to norepinephrine reuptake, there is a need to develop new compounds, methods, and pharmaceutical compositions to treat and alleviate these conditions. This invention addresses these needs and others.

SUMMARY OF THE INVENTION

The present invention provides compounds of Formula I:

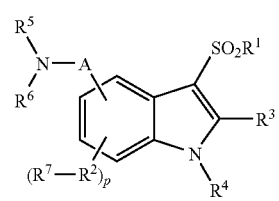

I or pharmaceutically acceptable salts or prodrugs thereof, wherein:

A is $C_{2-5}$ alkylene, $C_{2-5}$ alkenylene, or $C_{2-5}$ alkynylene, wherein each is optionally substituted with 1, 2, 3, or 4 independently selected $R^4$ groups;

$R^1$ is $C_{1-6}$ alkyl, cycloalkyl, heterocycloalkyl, aryl, heteroaryl, cycloalkylalkyl, heterocycloalkylalkyl, arylalkyl, or heteroarylalkyl, wherein each is optionally substituted by 1, 2, 3, or 4 independently selected $R^{1a}$ groups;

each $R^2$ is, independently, a bond, O, S, C(O), C(O)O, C(O)N($R^{2a}$), OC(O)N($R^{2a}$), S(O), S(O)$_2$, S(O)N($R^{2a}$), S(O)$_2$N($R^{2a}$), or N($R^{2a}$);

$R^3$ is H, $C_{1-6}$ alkyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, cycloalkyl, heterocycloalkyl, aryl, heteroaryl, cycloalkylalkyl, heterocycloalkylalkyl, arylalkyl, or heteroarylalkyl are each optionally substituted by 1, 2, 3, or 4 independently selected $R^{3a}$ groups;

$R^4$ is H, $C_{1-6}$ alkyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, cycloalkyl, heterocycloalkyl, aryl, heteroaryl, cycloalkylalkyl, heterocycloalkylalkyl, arylalkyl, or heteroarylalkyl are each optionally substituted by 1, 2, 3, or 4 independently $R^{4a}$ groups;

$R^5$ is H, $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{5a}$ groups;

$R^6$ is H, $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups;

each $R^7$ is, independently, H, halogen, CN, $NO_2$, $C_{1-6}$alkyl, $C_{1-6}$haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl are each optionally substituted by 1, 2, 3, or 4 independently selected $R^{7a}$ groups;

each $R^8$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{8b}$, $SR^{8b}$, $C(O)R^{8b}$, $C(O)NR^{8e}R^{8f}$, $C(O)OR^{8c}$, $OC(O)R^{8b}$, $OC(O)NR^{8e}R^{8f}$, $NR^{8e}R^{8f}$, $NR^{8b}C(O)R^{8c}$, $NR^{8b}C(O)OR^{8c}$, $S(O)R^{8d}$, $S(O)NR^{8e}R^{8}$, $S(O)_2R^{8c}$, $NR^{8b}S(O)_2R^{8c}$, or $S(O)_2NR^{8e}R^{8f}$, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{8a}$ groups;

each $R^A$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{Ab}$, $SR^{Ab}$, $C(O)R^{Ab}$, $C(O)NR^{Ae}R^{Af}$, $C(O)OR^{Ac}$, $OC(O)R^{Ab}$, $OC(O)NR^{Ae}R^{Af}$, $NR^{Ae}R^{Af}$, $NR^{Ab}C(O)R^{Ac}$, $NR^{Ab}C(O)OR^{Ac}$, $S(O)R^{Ad}$, $S(O)NR^{Ae}R^{Af}$, $S(O)_2R^{Ac}$, $NR^{Ab}S(O)_2R^{Ac}$, or $S(O)_2NR^{Ae}R^{Af}$;

each $R^{Ab}$, $R^{Ac}$, $R^{Ae}$, and $R^{Af}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{Ad}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{Ae}$ and $R^{Af}$, together with the N atom to which they are attached, form a 4-, 5-, 6- or 7-membered heterocycloalkyl group;

each $R^{1a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{1b}$, $SR^{1b}$, $C(O)R^{1b}$, $C(O)NR^{1e}R^{1f}$, $C(O)OR^{1c}$, $OC(O)R^{1b}$, $OC(O)NR^{1e}R^{1f}$, $NR^{1e}R^{1f}$, $NR^{1b}C(O)R^{1c}$, $NR^{1b}C(O)OR^{1c}$, $S(O)R^{1d}$, $S(O)NR^{1e}R^{1f}$, $S(O)_2R^{1c}$, $NR^{1b}S(O)_2R^{1c}$, or $S(O)_2NR^{1e}R^{1f}$;

each $R^{1b}$, $R^{1c}$, $R^{1e}$, and $R^{1f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{1d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{1e}$ and $R^{1f}$, together with the N atom to which they are attached, form a 4-, 5-, 6- or 7-membered heterocycloalkyl group;

each $R^{2a}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl are each optionally substituted with 1, 2, 3, or 4 independently selected $R^{2b}$ groups;

each $R^{2b}$ is, independently, halogen, CN, $NO_2$, OH, $C_{1-6}$ alkyl, $C_{1-6}$ haloalkyl, $C_{1-6}$ alkyloxy, cycloalkyloxy, heterocycloalkyloxy, aryloxy, heteroaryloxy, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{3a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{3b}$, $SR^{3b}$, $C(O)R^{3b}$, $C(O)NR^{3e}R^{3f}$, $C(O)OR^{3c}$, $OC(O)R^{3b}$, $OC(O)NR^{3e}R^{3f}$, $NR^{3e}R^{3f}$, $NR^{3b}C(O)R^{3c}$, $NR^{3b}C(O)OR^{3c}$, $S(O)R^{3d}$, $S(O)NR^{3e}R^{3f}$, $S(O)_2R^{3c}$, $NR^{3b}S(O)_2R^{3c}$, or $S(O)_2NR^{3e}R^{3f}$;

each $R^{3b}$, $R^{3c}$, $R^{3e}$, and $R^{3f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{3d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{3e}$ and $R^{3f}$, together with the N atom to which they are attached, form a 4-, 5-, 6- or 7-membered heterocycloalkyl group;

each $R^{4a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{4b}$, $SR^{4b}$, $C(O)R^{4b}$, $C(O)NR^{4e}R^{4f}$, $C(O)OR^{4c}$, $OC(O)R^{4b}$, $OC(O)NR^{4e}R^{4f}$, $NR^{4e}R^{4f}$, $NR^{4b}C(O)R^{4c}$, $NR^{4b}C(O)OR^{4c}$, $S(O)R^{4d}$, $S(O)NR^{4e}R^{4f}$, $S(O)_2R^{4c}NR^{4b}S(O)_2R^{4c}$, or $S(O)_2NR^{4e}R^{4f}$;

each $R^{4b}$, $R^{4c}$, $R^{4e}$, and $R^{4f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{4d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{4e}$ and $R^{4f}$, together with the N atom to which they are attached, form a 4-, 5-, 6- or 7-membered heterocycloalkyl group;

each $R^{5a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{5b}$, $SR^{5b}$, $C(O)R^{5b}$, $C(O)NR^{5e}R^{5f}$, $C(O)OR^{5c}$, $OC(O)R^{5b}$, $OC(O)NR^{5e}R^{5f}$, $NR^{5e}R^{5f}$, $NR^{5b}C(O)R^{5c}$, $NR^{5b}C(O)OR^{5c}$, $S(O)R^{5d}$, $S(O)NR^{5e}R^{5f}$, $S(O)_2R^{5c}NR^{5b}S(O)_2R^{5c}$, or $S(O)_2NR^{5e}R^{5f}$;

each $R^{5b}$, $R^{5c}$, $R^{5e}$, and $R^{5f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl is optionally substituted with 1, 2, 3, or 4 independently selected $R^{5'}$ groups;

each $R^{5d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein each is optionally substituted with 1, 2, 3, or 4 independently selected $R^{5'}$ groups;

or any $R^{5e}$ and $R^{5f}$, together with the N atom to which they are attached, form a 4-, 5-, 6- or 7-membered heterocycloalkyl group;

each $R^{6a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{6b}$, $SR^{6b}$, $C(O)R^{6b}$, $C(O)NR^{6e}R^{6f}$, $C(O)OR^{6c}$, $OC(O)R^{6b}$, $OC(O)NR^{6e}R^{6f}$, $NR^{6e}R^{6f}$, $NR^{6b}C(O)R^{6c}$, $NR^{6b}C(O)OR^{6c}$, $S(O)R^{6d}$, $S(O)NR^{6e}R^{6f}$, $S(O)_2R^{6c}NR^{6b}S(O)_2R^{6c}$, or $S(O)_2NR^{6e}R^{6f}$, each $R^{6b}$, $R^{6c}$, $R^{6e}$, and $R^{6f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl is optionally substituted with 1, 2, 3, or 4 independently selected $R^{6'}$ groups;

each $R^{6d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein each is optionally substituted with 1, 2, 3, or 4 independently selected $R^{6'}$ groups;

or any $R^{6e}$ and $R^{6f}$, together with the N atom to which they are attached, form a 4-, 5-, 6- or 7-membered heterocycloalkyl group;

each $R^{5'}$ and $R^{6'}$ is, independently, halogen, CN, $NO_2$, $C_{1-6}$alkyl, $C_{2-6}$alkenyl, $C_{2-6}$ alkynyl, $C_{1-6}$ haloalkyl, $C_{1-6}$ alkyloxy, cycloalkyloxy, heterocycloalkyloxy, aryloxy, heteroaryloxy, cycloalkyl, heterocycloalkyl, aryl, heteroaryl, cycloalkylalkyl, heterocycloalkylalkyl, arylalkyl, or heteroarylalkyl;

each $R^{7a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{7b}$, $SR^{7b}$, $C(O)R^{7b}$, $C(O)NR^{7e}R^{7f}$, $C(O)OR^{7c}$, $OC(O)R^{7b}$, $OC(O)NR^{7e}R^{7f}$, $NR^{7e}R^{7f}$, $NR^{7b}C(O)R^{7c}$, $NR^{7b}C(O)OR^{7c}$, $S(O)R^{7d}$, $S(O)NR^{7e}R^{7f}$, $S(O)_2R^{7c}NR^{7b}S(O)_2R^{7c}$, or $S(O)_2NR^{7e}R^{7f}$;

each $R^{7b}$, $R^{7c}$, $R^{7e}$, and $R^{7f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{7d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{7e}$ and $R^{7f}$, together with the N atom to which they are attached, form a 4-, 5-, 6- or 7-membered heterocycloalkyl group;

each $R^{8a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{8b'}$, $SR^{8b'}$, $C(O)$ $R^{8b'}$, $C(O)NR^{8e'}R^{8f'}$, $C(O)OR^{8c'}$, $OC(O)R^{8b'}$, $OC(O)NR^{8e'}R^{8f'}NR^{8e'}R^{8f'}$, $NR^{8b'}C(O)R^{8c'}$, $NR^{8b'}C(O)OR^{8c'}$, $S(O)R^{8d'}S(O)NR^{8e'}R^{8f'}$, $S(O)_2R^{8c'}$, $NR^{8b'}S(O)_2R^{8c'}$, or $S(O)_2NR^{8e'}R^{8f'}$;

each $R^{8b}$, $R^{8c}$, $R^{8e}$, and $R^{8f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{8e}$ and $R^{8f}$, together with the N atom to which they are attached, form a 4-, 5-, 6- or 7-membered heterocycloalkyl group;

each $R^{8b'}$, $R^{8c'}$, $R^{8e'}$, and $R^{8f'}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8d'}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{8e'}$ and $R^{8f'}$, together with the N atom to which they are attached, form a 4-, 5-, 6- or 7-membered heterocycloalkyl group; and p is 0, 1, 2, or 3;

with the proviso that if $R^7$ is halogen, CN, or $NO_2$, then $R^2$ is a bond.

The present invention further provides compounds of the invention having Formula I-A:

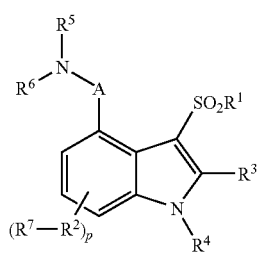

I-A or pharmaceutically acceptable salt or prodrug thereof.

The present invention further provides compounds of the invention having Formula I-B:

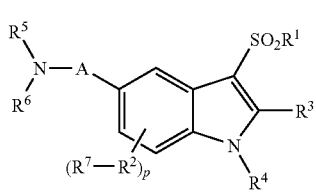

I-B or pharmaceutically acceptable salt or prodrug thereof.

The present invention further provides compounds of the invention having Formula I-C:

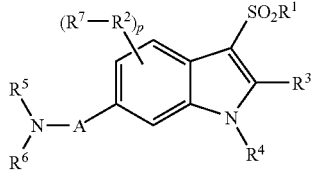

I-C or pharmaceutically acceptable salt or prodrug thereof.

The present invention further provides compounds of the invention having Formula I-D:

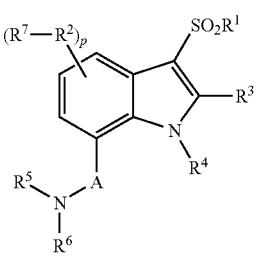

I-D or pharmaceutically acceptable salt or prodrug thereof.

The present invention further provides pharmaceutical compositions comprising a pharmaceutically acceptable carrier and a compound of the invention, or pharmaceutically acceptable salt or prodrug thereof.

The present invention further provides methods of treating disorders that are related to or affected by the 5-HT$_6$ receptor comprising administering to a patient in need thereof a therapeutically effective amount of a compound of the invention, or pharmaceutically acceptable salt or prodrug thereof.

The present invention further provides methods of treating disorders that are related to or affected by the 5-HT$_{2A}$ receptor comprising administering to a patient in need thereof a therapeutically effective amount of a compound of the invention, or pharmaceutically acceptable salt or prodrug thereof.

The present invention further provides methods of treating disorders that are related to or affected by norepinephrine reuptake inhibition comprising administering to a patient in need thereof a therapeutically effective amount of a compound of the invention, or pharmaceutically acceptable salt or prodrug thereof.

The present invention further provides methods of treating learning disorders, cognitive disorders or memory disorders comprising administering to a patient in need thereof a therapeutically effective amount of a compound of the invention, or pharmaceutically acceptable salt or prodrug thereof The present invention further provides methods of treating personality disorders comprising administering to a patient in need thereof a therapeutically effective amount of a compound of the invention, or pharmaceutically acceptable salt or prodrug thereof.

The present invention further provides methods of treating behavioral disorders comprising administering to a patient in need thereof a therapeutically effective amount of a compound of the invention, or pharmaceutically acceptable salt or prodrug thereof.

The present invention further provides methods of treating movement disorders comprising administering to a patient in need thereof a therapeutically effective amount of a compound of the invention, or pharmaceutically acceptable salt or prodrug thereof.

The present invention further provides methods of treating neurodegenerative disorders comprising administering to a patient in need thereof a therapeutically effective amount of a compound of the invention, or pharmaceutically acceptable salt or prodrug thereof.

The present invention further provides methods of treating drug withdrawal comprising administering to a patient in need thereof a therapeutically effective amount of a compound of the invention, or pharmaceutically acceptable salt or prodrug thereof.

The present invention further provides methods of treating sleep disorders comprising administering to a patient in need thereof a therapeutically effective amount of a compound of the invention, or pharmaceutically acceptable salt or prodrug thereof.

The present invention further provides methods of treating eating disorders comprising administering to a patient in need thereof a therapeutically effective amount of a compound of the invention, or pharmaceutically acceptable salt or prodrug thereof.

The present invention further provides methods of treating acute drug toxicity comprising administering to a patient in need thereof a therapeutically effective amount of a compound of the invention, or pharmaceutically acceptable salt or prodrug thereof.

The present invention further provides methods of treating cardiovascular disorders comprising administering to a patient in need thereof a therapeutically effective amount of a compound of the invention, or pharmaceutically acceptable salt or prodrug thereof.

The present invention further provides methods of treating sexual dysfunction comprising administering to a patient in need thereof a therapeutically effective amount of a compound of the invention, or pharmaceutically acceptable salt or prodrug thereof.

The present invention further provides methods of treating gastrointestinal disorders comprising administering to a patient in need thereof a therapeutically effective amount of a compound of the invention, or pharmaceutically acceptable salt or prodrug thereof.

The present invention further provides methods of treating genitourinary disorders comprising administering to a patient in need thereof a therapeutically effective amount of a compound of the invention, or pharmaceutically acceptable salt or prodrug thereof.

The present invention further provides methods of treating pain disorders or nerve disorders comprising administering to a patient in need thereof a therapeutically effective amount of a compound of the invention, or pharmaceutically acceptable salt or prodrug thereof.

The present invention further provides methods of treating vasomotor symptom disorders comprising administering to a patient in need thereof a therapeutically effective amount of a compound of the invention, or pharmaceutically acceptable salt or prodrug thereof.

DETAILED DESCRIPTION OF THE INVENTION

In one aspect, the present invention provides a compound of Formula I:

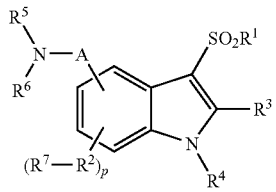

or pharmaceutically acceptable salt or prodrug thereof, wherein:

A is $C_{2-5}$ alkylene, $C_{2-5}$ alkenylene, or $C_{2-5}$ alkynylene, wherein each is optionally substituted with 1, 2, 3, or 4 independently selected $R^A$ groups;

$R^1$ is $C_{1-6}$ alkyl, cycloalkyl, heterocycloalkyl, aryl, heteroaryl, cycloalkylalkyl, heterocycloalkylalkyl, arylalkyl, or heteroarylalkyl, wherein each is optionally substituted by 1, 2, 3, or 4 independently selected $R^{1a}$ groups;

each $R^2$ is, independently, a bond, O, S, C(O), C(O)O, C(O)N($R^{2a}$), OC(O)N($R^{2a}$), S(O), S(O)$_2$, S(O)N($R^{2a}$), S(O)$_2$N($R^{2a}$), or N($R^{2a}$);

$R^3$ is H, $C_{1-6}$ alkyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, cycloalkyl, heterocycloalkyl, aryl, heteroaryl, cycloalkylalkyl, heterocycloalkylalkyl, arylalkyl, or heteroarylalkyl are each optionally substituted by 1, 2, 3, or 4 independently selected $R^{3a}$ groups;

$R^4$ is H, $C_{1-6}$ alkyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, cycloalkyl, heterocycloalkyl, aryl, heteroaryl, cycloalkylalkyl, heterocycloalkylalkyl, arylalkyl, or heteroarylalkyl are each optionally substituted by 1, 2, 3, or 4 independently $R^{4a}$ groups;

$R^5$ is H, $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{5a}$ groups;

$R^6$ is H, $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups;

each $R^7$ is, independently, H, halogen, CN, NO$_2$, $C_{1-6}$alkyl, $C_{1-6}$haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl are each optionally substituted by 1, 2, 3, or 4 independently selected $R^{7a}$ groups;

each $R^8$ is, independently, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, OR$^{8b}$, SR$^{8b}$, C(O)R$^{8b}$, C(O)NR$^{8e}$R$^{8f}$, C(O)OR$^{8c}$, OC(O)R$^{8b}$, OC(O)NR$^{8e}$R$^{8f}$, NR$^{8e}$R$^{8f}$, NR$^{8b}$C(O)R$^{8c}$, NR$^{8b}$C(O)OR$^{8c}$, S(O)R$^{8d}$, S(O)NR$^{8e}$R$^{8f}$, S(O)$_2$R$^{8c}$, NR$^{8b}$S(O)$_2$R$^{8c}$, or S(O)$_2$NR$^{8e}$R$^{8f}$, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{8a}$ groups;

each $R^A$ is, independently, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, OR$^{Ab}$, SR$^{Ab}$, C(O)R$^{Ab}$, C(O)NR$^{Ae}$R$^{Af}$, C(O)OR$^{Ac}$, OC(O)R$^{Ab}$, OC(O)NR$^{Ae}$R$^{Af}$, NR$^{Ae}$R$^{Af}$, NR$^{Ab}$C(O)R$^{Ac}$, NR$^{Ab}$C(O)OR$^{Ac}$, S(O)R$^{Ad}$, S(O)NR$^{Ae}$R$^{Af}$, S(O)$_2$R$^{Ac}$, NR$^{Ab}$S(O)$_2$R$^{Ac}$, or S(O)$_2$NR$^{Ae}$R$^{Af}$;

each R$^{Ab}$, R$^{Ac}$, R$^{Ae}$, and R$^{Af}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each R$^{Ad}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any R$^{Ae}$ and R$^{Af}$, together with the N atom to which they are attached, form a 4-, 5-, 6- or 7-membered heterocycloalkyl group;

each $R^{1a}$ is, independently, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, OR$^{1b}$, SR$^{1b}$, C(O)R$^{1b}$, C(O)NR$^{1e}$R$^{1f}$, C(O)OR$^{1c}$, OC(O)R$^{1b}$, OC(O)NR$^{1e}$R$^{1f}$, NR$^{1e}$R$^{1f}$, NR$^{1b}$C(O)R$^{1c}$, NR$^{1b}$C(O)OR$^{1c}$, S(O)R$^{1d}$, S(O)NR$^{1e}$R$^{1f}$, S(O)$_2$R$^{1c}$, NR$^{1b}$S(O)$_2$R$^{1c}$, or S(O)$_2$NR$^{1e}$R$^{1f}$;

each R$^{1b}$, R$^{1c}$, R$^{1e}$, and R$^{1f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each R$^{1d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any R$^{1e}$ and R$^{1f}$, together with the N atom to which they are attached, form a 4-, 5-, 6- or 7-membered heterocycloalkyl group;

each $R^{2a}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl are each optionally substituted with 1, 2, 3, or 4 independently selected $R^{2b}$ groups;

each $R^{2b}$ is, independently, halogen, CN, NO$_2$, OH, $C_{1-6}$ alkyl, $C_{1-6}$ haloalkyl, $C_{1-6}$ alkyloxy, cycloalkyloxy, heterocycloalkyloxy, aryloxy, heteroaryloxy, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{3a}$ is, independently, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{3b}$, $SR^{3b}$, $C(O)R^{3b}$, $C(O)NR^{3e}R^{3f}$, $C(O)OR^{3c}$, $OC(O)R^{3b}$, $OC(O)NR^{3e}R^{3f}$, $NR^{3e}R^{3f}$, $NR^{3b}C(O)R^{3c}$, $NR^{3b}C(O)OR^{3c}$, $S(O)R^{3d}$, $S(O)NR^{3e}R^{3f}$, $S(O)_2R^{3c}NR^{3b}S(O)_2R^{3c}$, or $S(O)_2NR^{3e}R^{3f}$;

each $R^{3b}$, $R^{3c}$, $R^{3e}$, and $R^{3f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{3d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{3e}$ and $R^{3f}$, together with the N atom to which they are attached, form a 4-, 5-, 6- or 7-membered heterocycloalkyl group;

each $R^{4a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{4b}$, $SR^{4b}$, $C(O)R^{4b}$, $C(O)NR^{4e}R^{4f}$, $C(O)OR^{4c}$, $OC(O)R^{4b}$, $OC(O)NR^{4e}R^{4f}$, $NR^{4e}R^{4f}$, $NR^{4b}C(O)R^{4c}$, $NR^{4b}C(O)OR^{4c}$, $S(O)R^{4d}$, $S(O)NR^{4e}R^{4f}$, $S(O)_2R^{4c}NR^{4b}S(O)_2R^{4c}$, or $S(O)_2NR^{4e}R^{4f}$;

each $R^{4b}$, $R^{4c}$, $R^{4e}$, and $R^{4f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{4d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{4e}$ and $R^{4f}$, together with the N atom to which they are attached, form a 4-, 5-, 6- or 7-membered heterocycloalkyl group;

each $R^{5a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{5b}$, $SR^{5b}$, $C(O)R^{5b}$, $C(O)NR^{5e}R^{5f}$, $C(O)OR^{5c}$, $OC(O)R^{5b}$, $OC(O)NR^{5e}R^{5f}$, $NR^{5e}R^{5f}$, $NR^{5b}C(O)R^{5c}$, $NR^{5b}C(O)OR^{5c}$, $S(O)R^{5d}$, $S(O)NR^{5e}R^{5f}$, $S(O)_2R^{5c}NR^{5b}S(O)_2R^{5c}$, or $S(O)_2NR^{5e}R^{5f}$;

each $R^{5b}$, $R^{5c}$, $R^{5e}$, and $R^{5f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl is optionally substituted with 1, 2, 3, or 4 independently selected $R^{5'}$ groups;

each $R^{5d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein each is optionally substituted with 1, 2, 3, or 4 independently selected $R^{5'}$ groups;

or any $R^{5e}$ and $R^{5f}$, together with the N atom to which they are attached, form a 4-, 5-, 6- or 7-membered heterocycloalkyl group;

each $R^{6a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{6b}$, $SR^{6b}$, $C(O)R^{6b}$, $C(O)NR^{6e}R^{6f}$, $C(O)OR^{6c}$, $OC(O)R^{6b}$, $OC(O)NR^{6e}R^{6f}$, $NR^{6e}R^{6f}$, $NR^{6b}C(O)R^{6c}$, $NR^{6b}C(O)OR^{6c}$, $S(O)R^{6d}$, $S(O)NR^{6e}R^{6f}$, $S(O)_2R^{6c}$, $NR^{6b}S(O)_2R^{6c}$, or $S(O)_2NR^{6e}R^{6f}$;

each $R^{6b}$, $R^{6c}$, $R^{6e}$, and $R^{6f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl is optionally substituted with 1, 2, 3, or 4 independently selected $R^{6'}$ groups;

each $R^{6d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein each is optionally substituted with 1, 2, 3, or 4 independently selected $R^{6'}$ groups;

or any $R^{6e}$ and $R^{6f}$, together with the N atom to which they are attached, form a 4-, 5-, 6- or 7-membered heterocycloalkyl group;

each $R^{5'}$ and $R^{6'}$ is, independently, halogen, CN, $NO_2$, $C_{1-6}$ alkyl, $C_{2-6}$ alkenyl, $C_{2-6}$ alkynyl, $C_{1-6}$ haloalkyl, $C_{1-6}$ alkyloxy, cycloalkyloxy, heterocycloalkyloxy, aryloxy, heteroaryloxy, cycloalkyl, heterocycloalkyl, aryl, heteroaryl, cycloalkylalkyl, heterocycloalkylalkyl, arylalkyl, or heteroarylalkyl;

each $R^{7a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{7b}$, $SR^{7b}$, $C(O)R^{7b}$, $C(O)NR^{7e}R^{7f}$, $C(O)OR^{7c}$, $OC(O)R^{7b}$, $OC(O)NR^{7e}R^{7f}$, $NR^{7e}R^{7f}$, $NR^{7b}C(O)R^{7c}$, $NR^{7b}C(O)OR^{7c}$, $S(O)R^{7d}$, $S(O)NR^{7e}R^{7f}$, $S(O)_2R^{7c}NR^{7b}S(O)_2R^{7c}$, or $S(O)_2NR^{7e}R^{7}$;

each $R^{7b}$, $R^{7c}$, $R^{7e}$, and $R^{7f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{7d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{7e}$ and $R^{7f}$, together with the N atom to which they are attached, form a 4-, 5-, 6- or 7-membered heterocycloalkyl group;

each $R^{8a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{8b'}$, $SR^{8b'}$, $C(O)R^{8b'}$, $C(O)NR^{8e'}R^{8f'}$, $C(O)OR^{8c'}$, $OC(O)R^{8b'}$, $OC(O)NR^{8e'}R^{8f'}$, $NR^{8e'}R^{8f'}$, $NR^{8b'}C(O)OR^{8c'}$, $S(O)R^{8d'}$, $S(O)NR^{8e'}R^{8f'}$, $S(O)_2R^{8c'}$, $NR^{8b'}S(O)_2R^{8c'}$, or $S(O)_2NR^{8e'}R^{8f'}$;

each $R^{8b}$, $R^{8c}$, $R^{8e}$, and $R^{8f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{8e}$ and $R^{8f}$, together with the N atom to which they are attached, form a 4-, 5-, 6- or 7-membered heterocycloalkyl group;

each $R^{8b'}$, $R^{8c'}$, $R^{8e'}$, and $R^{8f'}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8d'}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{8e'}$ and $R^{8f'}$, together with the N atom to which they are attached, form a 4-, 5-, 6- or 7-membered heterocycloalkyl group; and p is 0, 1, 2, or 3;

with the proviso that if $R^7$ is halogen, CN, or $NO_2$, then $R^2$ is a bond.

In some embodiments, A is $C_{2-5}$ alkylene.

In some embodiments, A is ethan-1,2-diyl or propan-1,3-diyl.

In some embodiments, $R^1$ is aryl substituted with 1, 2, 3, or 4 independently selected $R^{1a}$ groups.

In some embodiments, $R^1$ is phenyl substituted with 1, 2, 3, or 4 independently selected $R^{1a}$ groups.

In some embodiments, $R^1$ is phenyl or 3-fluorophenyl.

In some embodiments, $R^1$ is phenyl.

In some embodiments, each $R^2$ is, independently, a bond.

In some embodiments, $R^3$ is H, $C_{1-6}$ alkyl, or aryl.

In some embodiments, $R^3$ is H, methyl, ethyl, or phenyl.

In some embodiments, $R^4$ is H.

In some embodiments, $R^5$ is H, $C_{1-10}$alkyl, cycloalkyl, heterocycloalkylalkyl, or arylalkyl, wherein said $C_{1-10}$ alkyl is substituted with 1, 2, 3, or 4 independently selected $R^{5a}$ groups.

In some embodiments, $R^6$ is H, $C_{1-10}$alkyl, cycloalkyl, heterocycloalkylalkyl, or arylalkyl, wherein said $C_{1-10}$ alkyl is substituted with 1, 2, 3, or 4 independently selected $R^{6a}$ groups.

In some embodiments, $R^5$ and $R^6$ are each, independently, H, methyl, ethyl, propyl, isopropyl, isobutyl, pentan-3-yl, 1,2,2-trimethylpropyl, 2,2-dimethylpropyl, 2-methyl-1-butyl, 2-hydroxyethyl, dimethylaminopropyl, cyclopropyl, cyclobutyl, cyclopentyl, cyclohexyl, benzyl, or (tetrahydrofur-2-yl)methyl.

In some embodiments, $R^5$ and $R^6$, together with the N atom to which they are attached, form a 3-, 4-, 5-, 6-, 7-, or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups.

In some embodiments, $R^5$ and $R^6$, together with the N atom to which they are attached, form a 3-, 4-, 5-, 6-, 7-, or 8-membered heterocycloalkyl ring, wherein said heterocycloalkyl ring is optionally substituted with 1, 2, 3, or 4 independently selected $R^8$ groups.

In some embodiments, $R^5$ and $R^6$, together with the N atom to which they are attached, form a pyrrolidin-1-yl, piperidin-1-yl, morpholin-4-yl, piperazin-1-yl, 2-methylpiperidin-1-yl, 3-methylpiperidin-1-yl, 2,6-dimethylpiperidin-1-yl, 2-methylpyrrolidin-1-yl, azepan-1-yl, 4-methylpiperazin-1-yl, or azetidin-1-yl ring.

In some embodiments, each $R^7$ is H.

In some embodiments, each $R^{1a}$ is, independently, halogen.

In some embodiments, each $R^{1a}$ is F.

In some embodiments, each $R^{5a}$ is, independently, $OR^{5b}$ or $NR^{5e}R^{5f}$.

In some embodiments, each $R^{6a}$ is, independently, $OR^{6b}$ or $NR^{6e}R^{6f}$.

In some embodiments, each $R^{5b}$, $R^{5e}$, $R^{5f}$, $R^{6b}$, $R^{6e}$, and $R^{6f}$ is, independently, H or $C_{1-6}$ alkyl.

In some embodiments, each $R^{5b}$, $R^{5e}$, $R^{5f}$, $R^{6b}$, $R^{6e}$, and $R^{6f}$ is, independently, H or methyl.

In some embodiments, A is $C_{2-5}$ alkylene which is optionally substituted with 1, 2, 3, or 4 independently selected $R^A$ groups;

$R^1$ is $C_{1-6}$ alkyl, cycloalkyl, aryl, or heteroaryl, wherein each is optionally substituted by 1, 2, 3, or 4 $R^{1a}$;

each $R^2$ is, independently, a bond;

$R^3$ is H, $C_{1-6}$ alkyl, cycloalkyl, aryl, or heteroaryl, wherein said $C_{1-6}$ alkyl, cycloalkyl, aryl, and heteroaryl are each optionally substituted by 1, 2, 3, or 4 independently selected $R^{3a}$ groups;

$R^4$ is H, $C_{1-6}$ alkyl, cycloalkyl, aryl, or heteroaryl, wherein said $C_{1-6}$ alkyl, cycloalkyl, aryl, and heteroaryl are each optionally substituted by 1, 2, 3, or 4 independently selected $R^{4a}$ groups;

$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{5a}$ groups;

$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups; and each $R^7$ is, independently, H, halogen, $C_{1-6}$ alkyl, cycloalkyl, aryl, or heteroaryl, wherein said $C_{1-6}$alkyl, cycloalkyl, aryl, and heteroaryl are each optionally substituted by 1, 2, 3, or 4 independently selected $R^{7a}$ groups.

In some embodiments, A is $C_{2-5}$ alkylene;

$R^1$ is aryl, which is optionally substituted by 1, 2, 3, or 4 independently selected $R^{1a}$ groups;

each $R^2$ is, independently, a bond;

$R^3$ is H, $C_{1-6}$ alkyl, or aryl, wherein said $C_{1-6}$ alkyl and aryl are each optionally substituted by 1, 2, 3, or 4 independently selected $R^{3a}$ groups;

$R^4$ is H;

$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{5a}$ groups;

$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$, groups;

or $R^5$ and $R^6$, together with the N atom to which they are attached, form a 3-, 4-, 5-, 6- 7- or 8-membered heterocycloalkyl ring, wherein said heterocycloalkyl ring is optionally substituted with 1, 2, 3, or 4 independently selected $R^8$ groups; and each $R^7$ is, independently, H.

In some embodiments, A is ethan-1,2-diyl or propan-1,3-diyl;

$R^1$ is phenyl, which is optionally substituted by 1, 2, 3, or 4 independently selected $R^{1a}$ groups;

each $R^2$ is, independently, a bond;

$R^3$ is H, $C_{1-6}$ alkyl, or phenyl;

$R^4$ is H;

$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{5a}$ groups;

$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring, wherein said heterocycloalkyl ring is optionally substituted with 1, 2, 3, or 4 independently selected $R^8$ groups;

each $R^7$ is, independently, H;
each $R^{1a}$ is, independently, halogen;
each $R^{5a}$ is, independently, $OR^{5b}$ or $NR^{5e}R^{5f}$;
each $R^{6a}$ is, independently, $OR^{6b}$ or $NR^{6e}R^{6f}$;
each $R^8$ is, independently, $C_{1-6}$alkyl.

In some embodiments, A is ethan-1,2-diyl or propan-1,3-diyl;

$R^1$ is phenyl, which is optionally substituted by 1, 2, 3, or 4 independently selected $R^{1a}$ groups;
each $R^2$ is, independently, a bond;
$R^3$ is H, methyl, ethyl, or phenyl;
$R^4$ is H;
$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^5$, groups;
$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$ groups;
or $R^5$ and $R^6$, together with the N atom to which they are attached, form a 3-, 4-, 5-, 6- 7- or 8-membered heterocycloalkyl ring, wherein said heterocycloalkyl ring is optionally substituted with 1, 2, 3, or 4 independently selected $R^8$ groups;
each $R^7$ is, independently, H;
each $R^{1a}$ is, independently, F;
each $R^{5a}$ is, independently, OH or $N(CH_3)_2$;
each $R^{6a}$ is, independently, OH or $N(CH_3)_2$;
each $R^8$ is, independently, methyl; and
p is 0 or 1.

In some embodiments, A is ethan-1,2-diyl or propan-1,3-diyl;

$R^1$ is phenyl or 3-fluorophenyl;
$R^3$ is H, methyl, ethyl or phenyl;
$R^4$ is H;
$R^5$ is H, methyl, ethyl, propyl, isopropyl, isobutyl, pentan-3-yl, 1,2,2-trimethylpropyl, 2,2-dimethylpropyl, 2-methyl-1-butyl, cyclopropyl, cyclobutyl, cyclopentyl, cyclohexyl, benzyl, or (tetrahydrofur-2-yl)methyl, wherein said ethyl is optionally substituted with 1 $R^{5a}$;
$R^6$ is H, methyl, ethyl, propyl, isopropyl, isobutyl, pentan-3-yl, 1,2,2-trimethylpropyl, 2,2-dimethylpropyl, 2-methyl-1-butyl, cyclopropyl, cyclobutyl, cyclopentyl, cyclohexyl, benzyl, or (tetrahydrofur-2-yl)methyl, wherein said propyl is optionally substituted with 1 $R^{6a}$;
or $R^5$ and $R^6$, together with the N atom to which they are attached, form a pyrrolidin-1-yl, piperidin-1-yl, morpholin-4-yl, piperazin-1-yl, 2-methylpiperidin-1-yl, 3-methylpiperidin-1-yl, 2,6-dimethylpiperidin-1-yl, 2-methylpyrrolidin-1-yl, azepan-1-yl, 4-methylpiperazin-1-yl, or azetidin-1-yl ring;

each $R^{5a}$ is, independently, OH;
each $R^{6a}$ is, independently, $N(CH_3)_2$; and
p is 0.

In some embodiments, A is ethan-1,2-diyl or propan-1,3-diyl;

$R^1$ is phenyl or 3-fluorophenyl;
$R^3$ is H, methyl, ethyl or phenyl;
$R^4$ is H;
$R^5$ is H, methyl, ethyl, propyl, isopropyl, isobutyl, pentan-3-yl, 1,2,2-trimethylpropyl, 2,2-dimethylpropyl, 2-methyl-1-butyl, 2-hydroxyethyl, dimethylaminopropyl, cyclopropyl, cyclobutyl, cyclopentyl, cyclohexyl, benzyl, or (tetrahydrofur-2-yl)methyl.
$R^6$ is H, methyl, ethyl, propyl, isopropyl, isobutyl, pentan-3-yl, 1,2,2-trimethylpropyl, 2,2-dimethylpropyl, 2-methyl-1-butyl, 2-hydroxyethyl, dimethylaminopropyl, cyclopropyl, cyclobutyl, cyclopentyl, cyclohexyl, benzyl, or (tetrahydrofur-2-yl)methyl.
or $R^5$ and $R^6$, together with the N atom to which they are attached, form a pyrrolidin-1-yl, piperidin-1-yl, morpholin-4-yl, piperazin-1-yl, 2-methylpiperidin-1-yl, 3-methylpiperidin-1-yl, 2,6-dimethylpiperidin-1-yl, 2-methylpyrrolidin-1-yl, azepan-1-yl, 4-methylpiperazin-1-yl, or azetidin-1-yl ring; and
p is 0.

In some embodiments, the compound has Formula I-A:

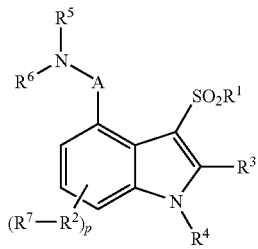

I-A or pharmaceutically acceptable salt or prodrug thereof.

In some embodiments, the compound has Formula I-B:

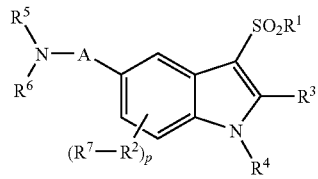

I-B or pharmaceutically acceptable salt or prodrug thereof.

In some embodiments, the compound has Formula I-C:

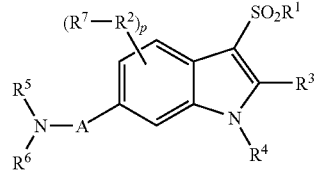

I-C or pharmaceutically acceptable salt or prodrug thereof.

In some embodiments, the compound has Formula I-D:

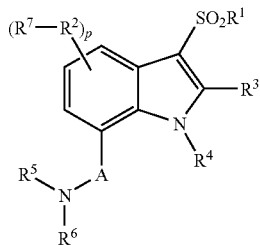

I-D or pharmaceutically acceptable salt or prodrug thereof.

In some embodiments, the compound of Formula I is:
N,N-dimethyl-N-{2-[3-(phenylsulfonyl)-1H-indol-5-yl]ethyl}amine;
N-{2-[3-(phenylsulfonyl)-1H-indol-5-yl]ethyl}-N-propylamine;
N-{2-[3-(phenylsulfonyl)-1H-indol-5-yl]ethyl}propan-2-amine;
N-{2-[3-(phenylsulfonyl)-1H-indol-5-yl]ethyl}cyclopropanamine;
N-{2-[3-(phenylsulfonyl)-1H-indol-5-yl]ethyl}cyclopentanamine;
N-benzyl-N-{2-[3-(phenylsulfonyl)-1H-indol-5-yl]ethyl}amine;
N-ethyl-N-methyl-N-{2-[3-(phenylsulfonyl)-1H-indol-5-yl]ethyl}amine;
N,N-diethyl-N-{2-[3-(phenylsulfonyl)-1H-indol-5-yl]ethyl}amine;
3-(phenylsulfonyl)-5-(2-pyrrolidin-1-ylethyl)-1H-indole;
3-(phenylsulfonyl)-5-(2-piperidin-1-ylethyl)-1H-indole;
5-(2-morpholin-4-ylethyl)-3-(phenylsulfonyl)-1H-indole;
{2-[3-(phenylsulfonyl)-1H-indol-5-yl]ethyl}amine;
3-(phenylsulfonyl)-5-(2-piperazin-1-ylethyl)-1H-indole;
N-methyl-N-{2-[3-(phenylsulfonyl)-1H-indol-5-yl]ethyl}amine;
N-methyl-N-{2-[2-methyl-3-(phenylsulfonyl)-1H-indol-5-yl]ethyl}amine;
N-{2-[2-ethyl-3-(phenylsulfonyl)-1H-indol-5-yl]ethyl}-N-methylamine;
N-methyl-N-{2-[2-phenyl-3-(phenylsulfonyl)-1H-indol-5-yl]ethyl}amine;
N,N-dimethyl-N-{2-[3-(phenylsulfonyl)-1H-indol-7-yl]ethyl}amine;
N-methyl-N-{2-[3-(phenylsulfonyl)-1H-indol-7-yl]ethyl}amine;
N-{2-[3-(phenylsulfonyl)-1H-indol-7-yl]ethyl}-N-propylamine;
N-{2-[3-(phenylsulfonyl)-1H-indol-7-yl]ethyl}propan-2-amine;
N-{2-[3-(phenylsulfonyl)-1H-indol-7-yl]ethyl}cyclopropanamine;
N-{2-[3-(phenylsulfonyl)-1H-indol-7-yl]ethyl}cyclopentanamine;
N-ethyl-N-methyl-N-{2-[3-(phenylsulfonyl)-1H-indol-7-yl]ethyl}amine;
N,N-diethyl-N-{2-[3-(phenylsulfonyl)-1H-indol-7-yl]ethyl}amine;
3-(phenylsulfonyl)-7-(2-pyrrolidin-1-ylethyl)-1H-indole;
3-(phenylsulfonyl)-7-(2-piperidin-1-ylethyl)-1H-indole;
7-(2-morpholin-4-ylethyl)-3-(phenylsulfonyl)-1H-indole;
{2-[3-(phenylsulfonyl)-1H-indol-7-yl]ethyl}amine;
3-(phenylsulfonyl)-7-(2-piperazin-1-ylethyl)-1H-indole;
N,N-dimethyl-N-{2-[3-(phenylsulfonyl)-1H-indol-4-yl]ethyl}amine;
N-methyl-N-{2-[3-(phenylsulfonyl)-1H-indol-4-yl]ethyl}amine;
N-ethyl-N-{2-[3-(phenylsulfonyl)-1H-indol-4-yl]ethyl}amine;
N-{2-[3-(phenylsulfonyl)-1H-indol-4-yl]ethyl}-N-propylamine;
N-{2-[3-(phenylsulfonyl)-1H-indol-4-yl]ethyl}propan-2-amine;
N-{2-[3-(phenylsulfonyl)-1H-indol-4-yl]ethyl}cyclopropanamine;
N-{2-[3-(phenylsulfonyl)-1H-indol-4-yl]ethyl}cyclobutanamine;
N-{2-[3-(phenylsulfonyl)-1H-indol-4-yl]ethyl}cyclopentanamine;
N-{2-[3-(phenylsulfonyl)-1H-indol-4-yl]ethyl}cyclohexanamine;
N-ethyl-N-methyl-N-{2-[3-(phenylsulfonyl)-1H-indol-4-yl]ethyl}amine;
N-cyclohexyl-N-methyl-N-{2-[3-(phenylsulfonyl)-1H-indol-4-yl]ethyl}amine;
N,N-diethyl-N-{2-[3-(phenylsulfonyl)-1H-indol-4-yl]ethyl}amine;
3-(phenylsulfonyl)-4-(2-pyrrolidin-1-ylethyl)-1H-indole;
3-(phenylsulfonyl)-4-(2-piperidin-1-ylethyl)-1H-indole;
4-(2-morpholin-4-ylethyl)-3-(phenylsulfonyl)-1H-indole;
N-{2-[3-(phenylsulfonyl)-1H-indol-4-yl]ethyl}-N-(1,2,2-trimethylpropyl)amine;
N-benzyl-N-{2-[3-(phenylsulfonyl)-1H-indol-4-yl]ethyl}amine;
N-isobutyl-N-{2-[3-(phenylsulfonyl)-1H-indol-4-yl]ethyl}amine;
N-(2,2-dimethylpropyl)-N-{2-[3-(phenylsulfonyl)-1H-indol-4-yl]ethyl}amine;
N,N-dimethyl-N'-{2-[3-(phenylsulfonyl)-1H-indol-4-yl]ethyl}propane-1,3-diamine;
N-{2-[3-(phenylsulfonyl)-1H-indol-4-yl]ethyl}-N-((tetrahydrofur-2-yl)methyl)amine;
4-{2-[(2R*,6S)-2,6-dimethylpiperidin-1-yl]ethyl}-3-(phenylsulfonyl)-1H-indole;
N-methyl-N-{2-[3-(phenylsulfonyl)-1H-indol-4-yl]ethyl}propan-2-amine;
N-ethyl-N-{2-[3-(phenylsulfonyl)-1H-indol-4-yl]ethyl}propan-2-amine;
4-[2-(2-methylpyrrolidin-1-yl)ethyl]-3-(phenylsulfonyl)-1H-indole;
4-[2-(2-methylpiperidin-1-yl)ethyl]-3-(phenylsulfonyl)-1H-indole;
4-[2-(3-methylpiperidin-1-yl)ethyl]-3-(phenylsulfonyl)-1H-indole;
4-(2-azepan-1-ylethyl)-3-(phenylsulfonyl)-1H-indole;
4-[2-(4-methylpiperazin-1-yl)ethyl]-3-(phenylsulfonyl)-1H-indole;
3-(phenylsulfonyl)-4-(2-piperazin-1-ylethyl)-1H-indole;
{2-[3-(phenylsulfonyl)-1H-indol-4-yl]ethyl}amine;
N-methyl-N-{2-[3-(3-fluorophenylsulfonyl)-1H-indol-4-yl]ethyl}amine;
N-ethyl-N-{2-[3-(3-fluorophenylsulfonyl)-1H-indol-4-yl]ethyl}amine;
N,N-dimethyl-N-{2-[3-(3-fluorophenylsulfonyl)-1H-indol-4-yl]ethyl}amine;
N-{2-[3-(3-fluorophenylsulfonyl)-1H-indol-4-yl]ethyl}-N-propylamine;
N-{2-[3-(3-fluorophenylsulfonyl)-1H-indol-4-yl]ethyl}propan-2-amine;

N-{2-[3-(3-fluorophenylsulfonyl)-1H-indol-4-yl]
ethyl}cyclopropanamine;
N-{2-[3-(3-fluorophenylsulfonyl)-1H-indol-4-yl]
ethyl}cyclobutanamine;
N-{2-[3-(3-fluorophenylsulfonyl)-1H-indol-4-yl]
ethyl}cyclopentanamine;
N-{2-[3-(3-fluorophenylsulfonyl)-1H-indol-4-yl]
ethyl}cyclohexanamine;
N-ethyl-N-methyl-N-{2-[3-(3-fluorophenylsulfonyl)-1H-
indol-4-yl]ethyl}amine;
N-cyclohexyl-N-methyl-N-{2-[3-(3-fluorophenylsulfo-
nyl)-1H-indol-4-yl]ethyl}amine;
N,N-diethyl-N-{2-[3-(3-fluorophenylsulfonyl)-1H-indol-
4-yl]ethyl}amine;
3-(3-fluorophenylsulfonyl)-4-(2-pyrrolidin-1-ylethyl)-
1H-indole;
3-(3-fluorophenylsulfonyl)-4-(2-piperidin-1-ylethyl)-1H-
indole;
4-(2-morpholin-4-ylethyl)-3-(3-fluorophenylsulfonyl)-
1H-indole;
N-isobutyl-N-{2-[3-(3-fluorophenylsulfonyl)-1H-indol-
4-yl]ethyl}amine;
(1-Ethyl-propyl)-{2-[3-(3-fluorophenylsulfonyl)-1H-in-
dol-4-yl]-ethyl}-amine;
{2-[3-(3-Fluorophenylsulfonyl)-1H-indol-4-yl]-ethyl}-
(2-methyl-butyl)-amine;
N-{2-[3-(3-fluorophenylsulfonyl)-1H-indol-4-yl]ethyl}-
N-(1,2,2-trimethylpropyl)amine;
N-(2,2-dimethylpropyl)-N-{2-[3-(3-fluorophenylsulfo-
nyl)-1H-indol-4-yl]ethyl}amine;
N-{2-[3-(3-fluorophenylsulfonyl)-1H-indol-4-yl]ethyl}-
N-((tetrahydrofur-2-yl)methyl)amine;
N'-{2-[3-(3-Fluorophenylsulfonyl)-1H-indol-4-yl]-
ethyl}-N,N-dimethyl-propane-1,3-diamine;
2-({2-[3-(3-Fluorophenylsulfonyl)-1H-indol-4-yl]-
ethyl}-methyl-amino)-ethanol;
{2-[3-(3-fluorophenylsulfonyl)-1H-indol-4-yl]
ethyl}amine;
N,N-dimethyl-N-{2-[3-(phenylsulfonyl)-1H-indol-6-yl]
ethyl}amine;
N-methyl-N-{2-[3-(phenylsulfonyl)-1H-indol-6-yl]
ethyl}amine;
N-ethyl-N-{2-[3-(phenylsulfonyl)-1H-indol-6-yl]
ethyl}amine;
N-{2-[3-(phenylsulfonyl)-1H-indol-6-yl]ethyl}-N-propy-
lamine;
N-{2-[3-(phenylsulfonyl)-1H-indol-6-yl]ethyl}propan-2-
amine;
N-{2-[3-(phenylsulfonyl)-1H-indol-6-yl]
ethyl}cyclopropanamine;
N-{2-[3-(phenylsulfonyl)-1H-indol-6-yl]
ethyl}cyclobutanamine;
N-{2-[3-(phenylsulfonyl)-1H-indol-6-yl]
ethyl}cyclopentanamine;
N-{2-[3-(phenylsulfonyl)-1H-indol-6-yl]
ethyl}cyclohexanamine;
N-ethyl-N-methyl-N-{2-[3-(phenylsulfonyl)-1H-indol-6-
yl]ethyl}amine;
N-cyclohexyl-N-methyl-N-{2-[3-(phenylsulfonyl)-1H-
indol-6-yl]ethyl}amine;
N,N-diethyl-N-{2-[3-(phenylsulfonyl)-1H-indol-6-yl]
ethyl}amine;
3-(phenylsulfonyl)-6-(2-pyrrolidin-1-ylethyl)-1H-indole;
3-(phenylsulfonyl)-6-(2-piperidin-1-ylethyl)-1H-indole;
4-(2-morpholin-6-ylethyl)-3-(phenylsulfonyl)-1H-indole;
3-phenylsulfonyl-6-(2-piperazin-1-yl-ethyl)-1H-indole;
N-isobutyl-N-{2-[3-(phenylsulfonyl)-1H-indol-6-yl]
ethyl}amine;
(1-Ethyl-propyl)-{2-[3-(phenylsulfonyl)-1H-indol-6-yl]-
ethyl}-amine;
{2-[3-(phenylsulfonyl)-1H-indol-6-yl]-ethyl}-(2-methyl-
butyl)-amine;
N-{2-[3-(phenylsulfonyl)-1H-indol-6-yl]ethyl}-N-(1,2,2-
trimethylpropyl)amine;
N-(2,2-dimethylpropyl)-N-{2-[3-(phenylsulfonyl)-1H-in-
dol-6-yl]ethyl}amine;
N-{2-[3-(phenylsulfonyl)-1H-indol-6-yl]ethyl}-N-((tet-
rahydrofur-2-yl)methyl)amine;
6-(2-Azetidin-1-yl-ethyl)-3-phenylsulfonyl-1H-indole;
{2-[3-(phenylsulfonyl)-1H-indol-6-yl]ethyl}amine;
N-isopropyl-3-[3-(phenylsulfonyl)-1H-indol-4-yl]pro-
pan-1-amine;
3-(phenylsulfonyl)-4-(3-piperidin-1-ylpropyl)-1H-indole;
or
N-ethyl-N-methyl-3-[3-(phenylsulfonyl)-1H-indol-4-yl]
propan-1-amine;

or pharmaceutically acceptable salt or prodrug thereof.
In some embodiments, the compound of Formula I-A is:
N,N-dimethyl-N-{2-[3-(phenylsulfonyl)-1H-indol-4-yl]
ethyl}amine;
N-methyl-N-{2-[3-(phenylsulfonyl)-1H-indol-4-yl]
ethyl}amine;
N-ethyl-N-{2-[3-(phenylsulfonyl)-1H-indol-4-yl]
ethyl}amine;
N-{2-[3-(phenylsulfonyl)-1H-indol-4-yl]ethyl}-N-propy-
lamine;
N-{2-[3-(phenylsulfonyl)-1H-indol-4-yl]ethyl}propan-2-
amine;
N-{2-[3-(phenylsulfonyl)-1H-indol-4-yl]
ethyl}cyclopropanamine;
N-{2-[3-(phenylsulfonyl)-1H-indol-4-yl]
ethyl}cyclobutanamine;
N-{2-[3-(phenylsulfonyl)-1H-indol-4-yl]
ethyl}cyclopentanamine;
N-{2-[3-(phenylsulfonyl)-1H-indol-4-yl]
ethyl}cyclohexanamine;
N-ethyl-N-methyl-N-{2-[3-(phenylsulfonyl)-1H-indol-4-
yl]ethyl}amine;
N-cyclohexyl-N-methyl-N-{2-[3-(phenylsulfonyl)-1H-
indol-4-yl]ethyl}amine;
N,N-diethyl-N-{2-[3-(phenylsulfonyl)-1H-indol-4-yl]
ethyl}amine;
3-(phenylsulfonyl)-4-(2-pyrrolidin-1-ylethyl)-1H-indole;
3-(phenylsulfonyl)-4-(2-piperidin-1-ylethyl)-1H-indole;
4-(2-morpholin-4-ylethyl)-3-(phenylsulfonyl)-1H-indole;
N-{2-[3-(phenylsulfonyl)-1H-indol-4-yl]ethyl}-N-(1,2,2-
trimethylpropyl)amine;
N-benzyl-N-{2-[3-(phenylsulfonyl)-1H-indol-4-yl]
ethyl}amine;
N-isobutyl-N-{2-[3-(phenylsulfonyl)-1H-indol-4-yl]
ethyl}amine;
N-(2,2-dimethylpropyl)-N-{2-[3-(phenylsulfonyl)-1H-in-
dol-4-yl]ethyl}amine;
N,N-dimethyl-N'-{2-[3-(phenylsulfonyl)-1H-indol-4-yl]
ethyl}propane-1,3-diamine;
N-{2-[3-(phenylsulfonyl)-1H-indol-4-yl]ethyl}-N-((tet-
rahydrofur-2-yl)methyl)amine;
4-{2-[(2R*,6S)-2,6-dimethylpiperidin-1-yl]ethyl}-3-
(phenylsulfonyl)-1H-indole;
N-methyl-N-{2-[3-(phenylsulfonyl)-1H-indol-4-yl]
ethyl}propan-2-amine;

N-ethyl-N-{2-[3-(phenylsulfonyl)-1H-indol-4-yl]ethyl}propan-2-amine;
4-[2-(2-methylpyrrolidin-1-yl)ethyl]-3-(phenylsulfonyl)-1H-indole;
4-[2-(2-methylpiperidin-1-yl)ethyl]-3-(phenylsulfonyl)-1H-indole;
4-[2-(3-methylpiperidin-1-yl)ethyl]-3-(phenylsulfonyl)-1H-indole;
4-(2-azepan-1-ylethyl)-3-(phenylsulfonyl)-1H-indole;
4-[2-(4-methylpiperazin-1-yl)ethyl]-3-(phenylsulfonyl)-1H-indole;
3-(phenylsulfonyl)-4-(2-piperazin-1-ylethyl)-1H-indole;
{2-[3-(phenylsulfonyl)-1H-indol-4-yl]ethyl}amine;
N-methyl-N-{2-[3-(3-fluorophenylsulfonyl)-1H-indol-4-yl]ethyl}amine;
N-ethyl-N-{2-[3-(3-fluorophenylsulfonyl)-1H-indol-4-yl]ethyl}amine;
N,N-dimethyl-N-{2-[3-(3-fluorophenylsulfonyl)-1H-indol-4-yl]ethyl}amine;
N-{2-[3-(3-fluorophenylsulfonyl)-1H-indol-4-yl]ethyl}-N-propylamine;
N-{2-[3-(3-fluorophenylsulfonyl)-1H-indol-4-yl]ethyl}propan-2-amine;
N-{2-[3-(3-fluorophenylsulfonyl)-1H-indol-4-yl]ethyl}cyclopropanamine;
N-{2-[3-(3-fluorophenylsulfonyl)-1H-indol-4-yl]ethyl}cyclobutanamine;
N-{2-[3-(3-fluorophenylsulfonyl)-1H-indol-4-yl]ethyl}cyclopentanamine;
N-{2-[3-(3-fluorophenylsulfonyl)-1H-indol-4-yl]ethyl}cyclohexanamine;
N-ethyl-N-methyl-N-{2-[3-(3-fluorophenylsulfonyl)-1H-indol-4-yl]ethyl}amine;
N-cyclohexyl-N-methyl-N-{2-[3-(3-fluorophenylsulfonyl)-1H-indol-4-yl]ethyl}amine;
N,N-diethyl-N-{2-[3-(3-fluorophenylsulfonyl)-1H-indol-4-yl]ethyl}amine;
3-(3-fluorophenylsulfonyl)-4-(2-pyrrolidin-1-ylethyl)-1H-indole;
3-(3-fluorophenylsulfonyl)-4-(2-piperidin-1-ylethyl)-1H-indole;
4-(2-morpholin-4-ylethyl)-3-(3-fluorophenylsulfonyl)-1H-indole;
N-isobutyl-N-{2-[3-(3-fluorophenylsulfonyl)-1H-indol-4-yl]ethyl}amine;
(1-Ethyl-propyl)-{2-[3-(3-fluorophenylsulfonyl)-1H-indol-4-yl]-ethyl}-amine;
{2-[3-(3-Fluorophenylsulfonyl)-1H-indol-4-yl]-ethyl}-(2-methyl-butyl)-amine;
N-{2-[3-(3-fluorophenylsulfonyl)-1H-indol-4-yl]ethyl}-N-(1,2,2-trimethylpropyl)amine;
N-(2,2-dimethylpropyl)-N-{2-[3-(3-fluorophenylsulfonyl)-1H-indol-4-yl]ethyl}amine;
N-{2-[3-(3-fluorophenylsulfonyl)-1H-indol-4-yl]ethyl}-N-((tetrahydrofur-2-yl)methyl)amine;
N'-{2-[3-(3-Fluorophenylsulfonyl)-1H-indol-4-yl]-ethyl}-N,N-dimethyl-propane-1,3-diamine;
2-({2-[3-(3-Fluorophenylsulfonyl)-1H-indol-4-yl]-ethyl}-methyl-amino)-ethanol;
{2-[3-(3-fluorophenylsulfonyl)-1H-indol-4-yl]ethyl}amine;
N-isopropyl-3-[3-(phenylsulfonyl)-1H-indol-4-yl]propan-1-amine;
3-(phenylsulfonyl)-4-(3-piperidin-1-ylpropyl)-1H-indole; or
N-ethyl-N-methyl-3-[3-(phenylsulfonyl)-1H-indol-4-yl]propan-1-amine;

or pharmaceutically acceptable salt or prodrug thereof.

In some embodiments, the compound of Formula I-B is:
N,N-dimethyl-N-{2-[3-(phenylsulfonyl)-1H-indol-5-yl]ethyl}amine;
N-{2-[3-(phenylsulfonyl)-1H-indol-5-yl]ethyl}-N-propylamine;
N-{2-[3-(phenylsulfonyl)-1H-indol-5-yl]ethyl}propan-2-amine;
N-{2-[3-(phenylsulfonyl)-1H-indol-5-yl]ethyl}cyclopropanamine;
N-{2-[3-(phenylsulfonyl)-1H-indol-5-yl]ethyl}cyclopentanamine;
N-benzyl-N-{2-[3-(phenylsulfonyl)-1H-indol-5-yl]ethyl}amine;
N-ethyl-N-methyl-N-{2-[3-(phenylsulfonyl)-1H-indol-5-yl]ethyl}amine;
N,N-diethyl-N-{2-[3-(phenylsulfonyl)-1H-indol-5-yl]ethyl}amine;
3-(phenylsulfonyl)-5-(2-pyrrolidin-1-ylethyl)-1H-indole;
3-(phenylsulfonyl)-5-(2-piperidin-1-ylethyl)-1H-indole;
5-(2-morpholin-4-ylethyl)-3-(phenylsulfonyl)-1H-indole;
{2-[3-(phenylsulfonyl)-1H-indol-5-yl]ethyl}amine;
3-(phenylsulfonyl)-5-(2-piperazin-1-ylethyl)-1H-indole;
N-methyl-N-{2-[3-(phenylsulfonyl)-1H-indol-5-yl]ethyl}amine;
N-methyl-N-{2-[2-methyl-3-(phenylsulfonyl)-1H-indol-5-yl]ethyl}amine;
N-{2-[2-ethyl-3-(phenylsulfonyl)-1H-indol-5-yl]ethyl}-N-methylamine; or
N-methyl-N-{2-[2-phenyl-3-(phenylsulfonyl)-1H-indol-5-yl]ethyl}amine;

or pharmaceutically acceptable salt or prodrug thereof.

In some embodiments, the compound of Formula I-C is:
N,N-dimethyl-N-{2-[3-(phenylsulfonyl)-1H-indol-6-yl]ethyl}amine;
N-methyl-N-{2-[3-(phenylsulfonyl)-1H-indol-6-yl]ethyl}amine;
N-ethyl-N-{2-[3-(phenylsulfonyl)-1H-indol-6-yl]ethyl}amine;
N-{2-[3-(phenylsulfonyl)-1H-indol-6-yl]ethyl}-N-propylamine;
N-{2-[3-(phenylsulfonyl)-1H-indol-6-yl]ethyl}propan-2-amine;
N-{2-[3-(phenylsulfonyl)-1H-indol-6-yl]ethyl}cyclopropanamine;
N-{2-[3-(phenylsulfonyl)-1H-indol-6-yl]ethyl}cyclobutanamine;
N-{2-[3-(phenylsulfonyl)-1H-indol-6-yl]ethyl}cyclopentanamine;
N-{2-[3-(phenylsulfonyl)-1H-indol-6-yl]ethyl}cyclohexanamine;
N-ethyl-N-methyl-N-{2-[3-(phenylsulfonyl)-1H-indol-6-yl]ethyl}amine;
N-cyclohexyl-N-methyl-N-{2-[3-(phenylsulfonyl)-1H-indol-6-yl]ethyl}amine;
N,N-diethyl-N-{2-[3-(phenylsulfonyl)-1H-indol-6-yl]ethyl}amine;
3-(phenylsulfonyl)-6-(2-pyrrolidin-1-ylethyl)-1H-indole;
3-(phenylsulfonyl)-6-(2-piperidin-1-ylethyl)-1H-indole;
4-(2-morpholin-6-ylethyl)-3-(phenylsulfonyl)-1H-indole;
3-phenylsulfonyl-6-(2-piperazin-1-yl-ethyl)-1H-indole;
N-isobutyl-N-{2-[3-(phenylsulfonyl)-1H-indol-6-yl]ethyl}amine;
(1-Ethyl-propyl)-{2-[3-(phenylsulfonyl)-1H-indol-6-yl]-ethyl}-amine;

{2-[3-(phenylsulfonyl)-1H-indol-6-yl]-ethyl}-(2-methyl-butyl)-amine;
N-{2-[3-(phenylsulfonyl)-1H-indol-6-yl]ethyl}-N-(1,2,2-trimethylpropyl)amine;
N-(2,2-dimethylpropyl)-N-{2-[3-(phenylsulfonyl)-1H-indol-6-yl]ethyl}amine;
N-{2-[3-(phenylsulfonyl)-1H-indol-6-yl]ethyl}-N-((tetrahydrofur-2-yl)methyl)amine;
6-(2-Azetidin-1-yl-ethyl)-3-phenylsulfonyl-1H-indole; or
{2-[3-(phenylsulfonyl)-1H-indol-6-yl]ethyl}amine;

or pharmaceutically acceptable salt or prodrug thereof.

In some embodiments, the compound of Formula I-D is:
N,N-dimethyl-N-{2-[3-(phenylsulfonyl)-1H-indol-7-yl]ethyl}amine;
N-methyl-N-{2-[3-(phenylsulfonyl)-1H-indol-7-yl]ethyl}amine;
N-{2-[3-(phenylsulfonyl)-1H-indol-7-yl]ethyl}-N-propylamine;
N-{2-[3-(phenylsulfonyl)-1H-indol-7-yl]ethyl}propan-2-amine;
N-{2-[3-(phenylsulfonyl)-1H-indol-7-yl]ethyl}cyclopropanamine;
N-{2-[3-(phenylsulfonyl)-1H-indol-7-yl]ethyl}cyclopentanamine;
N-ethyl-N-methyl-N-{2-[3-(phenylsulfonyl)-1H-indol-7-yl]ethyl}amine;
N,N-diethyl-N-{2-[3-(phenylsulfonyl)-1H-indol-7-yl]ethyl}amine;
3-(phenylsulfonyl)-7-(2-pyrrolidin-1-ylethyl)-1H-indole;
3-(phenylsulfonyl)-7-(2-piperidin-1-ylethyl)-1H-indole;
7-(2-morpholin-4-ylethyl)-3-(phenylsulfonyl)-1H-indole;
{2-[3-(phenylsulfonyl)-1H-indol-7-yl]ethyl}amine; or
3-(phenylsulfonyl)-7-(2-piperazin-1-ylethyl)-1H-indole;

or pharmaceutically acceptable salt or prodrug thereof.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination. For example, the embodiments described in the context of Formula I can also be provided for Formulas I-A, I-B, I-C, or I-D.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

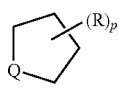

then it is understood that substituent R can occur p number of times on the ring, and R can be a different moiety at each occurrence. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

At various places in the present specification, linking substituents are described. It is specifically intended that each linking substituent include both the forward and backward forms of the linking substituent. For example, C(O)O includes both C(O)O and OC(O).

As used herein, the term "alkyl", employed alone or in combination with other terms, refers to a saturated hydrocarbon group that may be straight-chain or branched. In some embodiments, the alkyl group contains 1 to 10 or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like.

As used herein, the term "alkylene", employed alone or in combination with other terms, refers to a divalent alkyl linking group. In some embodiments, the alkylene group contains 2 to 5 carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "alkenyl", employed alone or in combination with other terms, refers to an alkyl group having one or more double carbon-carbon bonds. In some embodiments, the alkenyl moiety contains 2 to 10 or 2 to 6 carbon atoms. Example alkenyl groups include, but are not limited to, ethenyl, n-propenyl, isopropenyl, n-butenyl, sec-butenyl, and the like.

As used herein, the term "alkenylene", employed alone or in combination with other terms, refers to a divalent alkenyl group. In some embodiments, the alkenylene moiety contains 2 to 5 carbon atoms. Example alkenylene groups include, but are not limited to, ethen-1,2-diyl, propen-1,3-diyl, propen-1,2-diyl, buten-1,4-diyl, buten-1,3-diyl, buten-1,2-diyl, 2-methyl-propen-1,3-diyl, and the like.

As used herein, "alkynyl", employed alone or in combination with other terms, refers to an alkyl group having one or more triple carbon-carbon bonds. Example alkynyl groups include, but are not limited to, ethynyl, propyn-1-yl, propyn-2-yl, and the like. In some embodiments, the alkynyl moiety contains 2 to 10 or 2 to 6 carbon atoms.

As used herein, the term "alkynylene", employed alone or in combination with other terms, refers to a divalent alkynyl group. In some embodiments, the alkynylene moiety contains 2 to 5 carbon atoms. Example alkynylene groups include, but are not limited to, ethyn-1,2-diyl, propyn-1,3,-diyl, 1-butyn-1,4-diyl, 1-butyn-1,3-diyl, 2-butyn-1,4-diyl, and the like.

As used herein, the term "haloalkyl", employed alone or in combination with other terms, refers to an alkyl group having from one halogen atom to 2n+1 halogen atoms which may be the same or different, where "n" is the number of carbon atoms in the alkyl group.

As used herein, the term "carbonyl", employed alone or in combination with other terms, refers to a —C(O)— group, which is a divalent one-carbon moiety further bonded to an oxygen atom with a double bond.

As used herein, the term "sulfinyl", employed alone or in combination with other terms, refers to a —S(O)— group, which is a divalent one-sulfur moiety further bonded to an oxygen atom with a double bond.

As used herein, the term "sulfonyl", employed alone or in combination with other terms, refers to a —S(O)$_2$— group, which is a divalent one-sulfur moiety further bonded to two oxygen atoms via double bonds.

As used herein, the term "cycloalkyl", employed alone or in combination with other terms, refers to a non-aromatic cyclic hydrocarbon moiety, which may optionally contain one or more alkenylene or alkynylene groups as part of the ring structure. Cycloalkyl groups can include mono- or polycyclic (e.g., having 2, 3 or 4 fused or covalently linked rings) ring systems. Also included in the definition of cycloalkyl are moieties that have one or more aromatic rings fused (i.e., having a bond in common with) to the cycloalkyl ring, for example, benzo derivatives of pentane, pentene, hexane, and the like. Cycloalkyl groups can be characterized as having 3 to 14 ring members. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "heterocycloalkyl", "heterocycloalkyl ring", or "heterocycloalkyl group", employed alone or in combination with other terms, refers to non-aromatic ring system, which may optionally contain one or more alkenylene or alkynylene groups as part of the ring structure, and which has at least one heteroatom ring member selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused or covalently bonded rings) ring systems. Heterocycloalkyl groups can be characterized as having 3-20 ring-forming atoms. The carbon atoms or hetereoatoms in the ring(s) of the heterocycloalkyl group can be oxidized to form a carbonyl, sulfinyl, or sulfonyl group (or other oxidized linkage) or a nitrogen atom can be quaternized. Example heterocycloalkyl groups include, but are not limited to, the following rings wherein Q is NR, O or S:

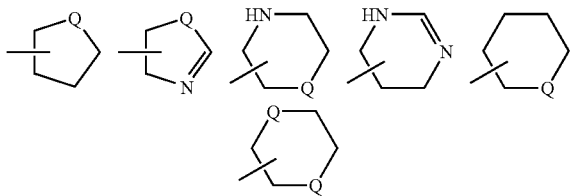

In some embodiments, the heterocyclyl group may be substituted as specified. In some embodiments, the heterocycloalkyl group is pyrrolidin-1-yl, piperidin-1-yl, morpholin-4-yl, piperazin-1-yl, azepan-1-yl, azetidin-1-yl, 2,6-dimethylpiperidin-1-yl, 2-methylpyrrolidin-1-yl, 2-methylpiperidin-1-yl, 3-methylpiperidin-1-yl, or 4-methylpiperazin-1-yl.

As used herein, the term "aryl", employed alone or in combination with other terms, refers to a monocyclic or polycyclic (e.g., having 2, 3 or 4 fused or covalently linked rings) aromatic hydrocarbon moiety, such as, but not limited to, phenyl, 1-naphthyl, 2-naphthyl, anthracenyl, phenanthrenyl, and the like. In some embodiments, the aryl group may be substituted as specified. For example, in some embodiments, the aryl group is phenyl optionally substituted by 1, 2, 3, or 4 halogen atoms.

As used herein, the term "heteroaryl", "heteroaryl ring", or "heteroaryl group", employed alone or in combination with other terms, refers to a monocyclic or polycyclic (e.g., having 2, 3 or 4 fused or covalently linked rings) aromatic hydrocarbon moiety, having one or more heteroatom ring members selected from nitrogen, sulfur and oxygen. When the heteroaryl group contains more than one heteroatom ring member, the heteroatoms may be the same or different. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. In some embodiments, the heteroaryl group has 5 to 10 carbon atoms.

As used herein, the term "cycloalkylalkyl" refers to a group of formula -alkyl-cycloalkyl. In some embodiments, the alkyl portion of the cycloalkylalkyl group has 1 to 6 carbon atoms.

As used herein, the term "heterocycloalkylalkyl" refers to a group of formula -alkyl-heterocycloalkyl. In some embodiments, the alkyl portion of the heterocycloalkylalkyl group has 1 to 6 carbon atoms. In some embodiments, the alkyl portion of the heterocycloalkylalkyl group is methylene. In some embodiments, the heterocycloalkylalkyl group is (tetrahydrofur-2-yl)methyl.

As used herein, the term "arylalkyl" refers to a group of formula -alkyl-aryl. In some embodiments, the alkyl portion of the arylalkyl group has 1 to 6 carbon atoms.

In some embodiments, the alkyl portion of the arylalkyl group is methyl. In some embodiments, the arylalkyl group is benzyl.

As used herein, the term "heteroarylalkyl" refers to a group of formula -alkyl-heteroaryl. In some embodiments, the alkyl portion of the heteroaryl group has 1 to 6 carbon atoms.

As used herein, the term "cycloalkyloxy" refers to a group of formula —O-cycloalkyl.

As used herein, the term "heterocycloalkyloxy" refers to a group of formula —O-heterocycloalkyl.

As used herein, the term "aryloxy" refers to a group of formula —O-aryl.

As used herein, the term "heteroaryloxy" refers to a group of formula —O-heteroaryl.

The compounds in this invention may contain one or more asymmetric centers, which can thus give rise to optical isomers (enantiomers) and diastereomers. While shown without respect to the stereochemistry in Formulas I, I-A, I-B, I-C, and I-D, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. The use of these compounds is intended to cover the racemic mixture or either of the chiral enantiomers.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

One skilled in the art will also recognize that it is possible for tautomers to exist for the compounds of the present invention. The present invention includes all such tautomers even though not shown in the formulas herein.

Compounds of the invention can also include all isotopes of atoms occurring in the intermediates or final compounds. Isotopes include those atoms having the same atomic number but different mass numbers. For example, isotopes of hydrogen include tritium and deuterium.

The compounds of the present invention also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

The present invention also includes prodrugs of the compounds described herein. As used herein, "prodrug" refers to a moiety that releases a compound of the invention when administered to a patient. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference in their entireties.

The Formula I, I-A, I-B, I-C, and I-D compounds of the invention are useful for the treatment of disorders that are related to or affected by the $5\text{-HT}_6$ receptor, including, without limitation, learning, cognitive, and memory disorders; personality disorders; behavioral disorders; movement disorders; neurodegenerative disorders; and drug withdrawal. As used herein, the term "$5\text{-HT}_6$ receptor" refers to the 5-hydroxytryptamine-6 receptor. Disorders that are related to or affected by the $5\text{-HT}_6$ receptor includes those disorders whose symptomatology, progression, development, and/or pathology are associated or affected by the $5\text{-HT}_6$ receptor. Accordingly, the present invention provides a method of treating disorders that are related to or affected by the $5\text{-HT}_6$ receptor which comprises administering to a patient in need thereof a therapeutically effective amount of a compound of Formula I or pharmaceutically acceptable salt or prodrug thereof.

In some embodiments, the present invention provides a method of treating disorders that are related to or affected by the $5\text{-HT}_6$ receptor which comprises administering to a patient in need thereof a therapeutically effective amount of a compound of Formula I-A, or pharmaceutically acceptable salt or prodrug thereof. In some embodiments, the present invention provides a method of treating disorders that are related to or affected by the $5\text{-HT}_6$ receptor which comprises administering to a patient in need thereof a therapeutically effective amount of a compound of Formula I-B, or pharmaceutically acceptable salt or prodrug thereof. In some embodiments, the present invention provides a method of treating disorders that are related to or affected by the $5\text{-HT}_6$ receptor which comprises administering to a patient in need thereof a therapeutically effective amount of a compound of Formula I-C, or pharmaceutically acceptable salt or prodrug thereof. In some embodiments, the present invention provides a method of treating disorders that are related to or affected by the $5\text{-HT}_6$ receptor which comprises administering to a patient in need thereof a therapeutically effective amount of a compound of Formula I-D, or pharmaceutically acceptable salt or prodrug thereof. The methods can include all of the embodiments for the compounds of Formulas I, I-A, I-B, I-C, and I-D hereinbefore described, including various combinations and subcombinations of the embodiments.

Additionally, compounds of Formulas I, I-A, I-B, I-C, and I-D are useful for the treatment of disorders that are related to or affected by the $5\text{-HT}_{2A}$ receptor, including, without limitation, personality disorders such as schizophrenia; movement disorders such as Parkinson's disease, tardive dyskinesia, ataxia, bradykinesia, paroxysmal dyskinesia, restless leg syndrome, tremor, essential tremor, and epilepsy; behavioral disorders such as depression, obsessive compulsive disorder, suicidality, anxiety disorder, bipolar disorder, and panic disorder; eating disorders such as anorexia nervosa, bulimia nervosa, night eating syndrome, and compulsive overeating; sleep disorders such as insomnia, sleep apnea, narcolepsy, seasonal affective disorder, restless leg syndrome, shift work sleep disorder, and delayed sleep phase syndrome; drug withdrawal; acute toxicity associated with certain psychotomimetic agents such as LSD or MDMA; cardiovascular conditions such as coronary artery disease, myocardial infarction, transient ischemic attack, angina, atrial fibrillation, reducing platelet aggregation and reducing the risk of blood clot formation; sexual dysfunction; gastrointestinal disorders such as irritable bowel syndrome, chronic constipation, gastroesophageal reflux disease, and dyspepsia; genitourinary disorders such as stress urinary incontinence and urge urinary incontinence; vasomotor disorders; and pain and nerve disorders. As used herein, the term "$5\text{-HT}_{2A}$ receptor" refers to the 5-hydroxytryptamine-2A receptor. Disorders that are related to or affected by the $5\text{-HT}_{2A}$ receptor includes those disorders whose symptomatology, progression, development, and/or pathology are associated or affected by the $5\text{-HT}_{2A}$ receptor. Accordingly, the present invention provides a method of treating disorders that are related to or affected by the $5\text{-HT}_{2A}$ receptor which comprises administering to a patient in need thereof a therapeutically effective amount of a compound of Formula I, or pharmaceutically acceptable salt or prodrug thereof.

In some embodiments, the present invention provides a method of treating disorders that are related to or affected by the $5\text{-HT}_{2A}$ receptor which comprises administering to a patient in need thereof a therapeutically effective amount of a compound of Formula I-A, or pharmaceutically acceptable salt or prodrug thereof. In some embodiments, the present invention provides a method of treating disorders that are related to or affected by the $5\text{-HT}_{2A}$ receptor which comprises administering to a patient in need thereof a therapeutically effective amount of a compound of Formula I-B, or pharmaceutically acceptable salt or prodrug thereof. In some embodiments, the present invention provides a method of treating disorders that are related to or affected by the $5\text{-HT}_{2A}$ receptor which comprises administering to a patient in need thereof a therapeutically effective amount of a compound of Formula I-C, or pharmaceutically acceptable salt or prodrug thereof. In some embodiments, the present invention provides a method of treating disorders that are related to or affected by the $5\text{-HT}_{2A}$ receptor which comprises administering to a patient in need thereof a therapeutically effective amount of a compound of Formula I-D, or pharmaceutically acceptable salt or prodrug thereof. The methods can include all of the embodiments for the compounds of Formulas I, I-A, I-B, I-C, and I-D hereinbefore described, including various combinations and subcombinations of the embodiments.

Additionally, compounds of Formula I, I-A, I-B, I-C, and I-D are useful for the treatment of disorders that are related to or affected by norepinephrine reuptake inhibition, including, without limitation, vasomotor symptoms (VMS) disorders such as hot flushes and night sweats; behavioral disorders such as major depressive disorder, obsessive compulsive disorder, suicidality, anxiety disorder, bipolar disorder, and panic disorder; sexual dysfunction; gastrointestinal disorders such as irritable bowel syndrome, chronic constipation, gastroesophageal reflux disease, and dyspepsia; genitourinary disorders such as stress urinary incontinence and urge urinary incontinence; learning, cognitive, or memory disorders such as attention deficit disorder or Alzheimer's disease; and nerve or pain disorders such as chronic fatigue syndrome, fibromyalgia syndrome, diabetic neuropathy, chronic pain, pain neuropathy, and antinociceptive pain. Accordingly, the present invention provides a method of treating disorders that are related to or affected by norepinephrine reuptake inhibition which comprises administering to a patient in need thereof a therapeutically effective amount of a compound of Formula I, or pharmaceutically acceptable salt or prodrug thereof.

In some embodiments, the present invention provides a method of treating disorders that are related to or affected by norepinephrine reuptake inhibition which comprises administering to a patient in need thereof a therapeutically effective amount of a compound of Formula I-A, or pharmaceutically acceptable salt or prodrug thereof. In some embodiments, the present invention provides a method of treating disorders that are related to or affected by norepinephrine reuptake inhibition which comprises administering to a patient in need thereof a therapeutically effective amount of a compound of Formula I-B, or pharmaceutically acceptable salt or prodrug thereof. In some embodiments, the present invention provides a method of treating disorders that are related to or affected by norepinephrine reuptake inhibition which comprises administering to a patient in need thereof a therapeutically effective amount of a compound of Formula I-C, or pharmaceutically acceptable salt or prodrug thereof. In some embodiments, the present invention provides a method of treating disorders that are related to or affected by norepinephrine reuptake inhibition which comprises administering to a patient in need thereof a therapeutically effective amount of a compound of Formula I-D, or pharmaceutically acceptable salt or prodrug thereof. The methods can include all of the embodiments for the compounds of Formulas I, I-A, I-B, I-C, and I-D hereinbefore described, including various combinations and subcombinations of the embodiments.

In some embodiments, the present invention provides a method of treating a learning disorder, cognitive disorder or memory disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "learning disorder" refers to a disorder, injury or disease that interferes with the ability of a patient to learn or to make academic progress. As used herein, the term "cognitive disorder" refers to a disorder, injury or disease that interferes with the ability of a patient to understand or comprehend external stimuli or concepts, or that interferes with the ability of a patient to interact socially. As used herein, the term "memory disorder" refers to a disorder, injury or disease that interferes with the short- or long-term memory of a patient.

In some embodiments, the learning disorder, cognitive disorder, or memory disorder is Alzheimer's disease or attention deficit disorder. As used herein, the term "attention deficit disorder" refers to ADD or ADHD. As used herein, the term "ADD" refers to attention deficit disorder, and the term "ADHD" refers to attention deficit hyperactivity disorder.

In some embodiments, the present invention provides a method of treating a personality disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "personality disorder" refers to any disorder, injury or disease that interferes with the personality or social functioning of a patient.

In some embodiments, the personality disorder is schizophrenia.

In some embodiments, the present invention provides a method of treating a behavioral disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "behavioral disorder" refers to a disorder, injury or disease that interferes with the behavior or emotional state of a patient.

In some embodiments, the behavorial disorder is depression, obsessive compulsive disorder, suicidality, anxiety disorder, bipolar disorder, or panic disorder.

In some embodiments, the present invention provides a method of treating a movement disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "movement disorder" refers to a disorder, injury, or disease that interferes with the bodily movements of a patient.

In some embodiments, the movement disorder is Parkinson's disease, tardive dyskinesia, ataxia, bradykinesia, paroxysmal dyskinesias, restless leg syndrome, tremor, essential tremor, or epilepsy.

In some embodiments, the present invention provides a method of treating a neurodegenerative disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "neurodegenerative disorder" refers to disorders associated with the nervous system of a patient, including, but not limited to the brain, spinal cord, and nerves.

In some embodiments, the neurodegenerative disorder is stroke, head trauma, Parkinson's disease, or Alzheimer's disease.

In some embodiments, the present invention provides a method of treating drug withdrawal comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the phrase "drug withdrawal" refers to symptoms and/or pathology associated with discontinuing or reducing use of a compound or substance by a patient who has become physically and/or psychologically dependent on the compound or substance after a period of use.

In some embodiments, the drug withdrawal is nicotine withdrawal, alcohol withdrawal, cocaine withdrawal, heroin withdrawal, amphetamine withdrawal or narcotic drug withdrawal.

In some embodiments, the present invention provides a method of treating a sleep disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "sleep disorder" refers to a disorder, injury, or disease that interferes with the normal sleep of a patient.

In some embodiments, the sleep disorder is insomnia, sleep apnea, narcolepsy, seasonal affective disorder, restless leg syndrome, shift work sleep disorder, or delayed sleep phase syndrome.

In some embodiments, the present invention provides a method of treating an eating disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "eating disorder" refers to a disorder or syndrome in which the patient eats in a way that disturbs his or her physical or mental health or that disrupts his or her normal daily activities.

In some embodiments, the eating disorder is anorexia nervosa, bulimia nervosa, night eating syndrome, or compulsive overeating.

In some embodiments, the present invention provides a method of treating acute drug toxicity comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "acute drug toxicity" refers to adverse physical, neurological, or mental effects occurring within a short time of administration of a single dose of a chemical substance, or immediately following short or continuous exposure, or multiple doses over a short period of time, such as twenty-four hours. The adverse effects include long-term and short-term effects on the patient from the exposure to the drug. Acute drug toxicity can result from exposure to various drugs, including, but not limited to, 3,4-methylenedioxymethamphetamine (MDMA) or lysergic acid diethylamide (LSD).

In some embodiments, the present invention provides a method of treating a cardiovascular disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "cardiovascular disease" refers to a disorder, injury, or disease that detrimentally affects the heart or blood vessels.

In some embodiments, the cardiovascular disorder is coronary artery disease, myocardial infarction, transient ischemic attack, angina, atrial fibrillation, platelet aggregation, or risk of blood clot formation.

In some embodiments, the present invention provides a method of treating sexual dysfunction comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

In some embodiments, the present invention provides a method of treating a gastrointenstinal disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "gastrointenstinal disorder" refers to a condition or disease affecting the gastrointestinal system as it extends from the esophagus to the rectum. Examples of gastrointestinal disorders that are treatable by the methods of the invention include the gastrointestinal disorders listed in M. H. Beers & R. Berkow, The Merck Manual of Diagnosis and Treatment, section 3 (17th ed., John Wiley and Sons, 1999), which is incorporated herein by reference in its entirety.

In some embodiments, the gastrointenstinal disorder is irritable bowel syndrome, chronic constipation, gastroesophageal reflux disease, or dyspepsia.

In some embodiments, the present invention provides a method of treating a genitourinary disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "genitourinary disorder" refers to a disorder, disease, or injury associated with urinary and genital organs. Examples of genitourinary disorders that are treatable by the methods of the invention include the genitourinary disorders listed in M. H. Beers & R. Berkow, The Merck Manual of Diagnosis and Treatment, section 17 (17th ed., John Wiley and Sons, 1999), which is incorporated herein by reference in its entirety.

In some embodiments, the genitourinary disorder is stress urinary incontinence or urge urinary incontinence.

In some embodiments, the present invention provides a method of treating a pain disorder or nerve disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "nerve disorder" refers to a disorder, disease, or injury that affects the nervous system of a patient, including the brain, spinal cord, and nerves. As used herein, the term "pain disorder" refers to a disorder, disease, or injury that causes pain in parts of a patient's body that include, but are not limited to, the muscles, nerves, or bones.

In some embodiments, the pain disorder or nerve disorder is chronic fatigue syndrome, fibromyalgia, pain neuropathy, antinociceptive pain, chronic pain syndrome, or diabetic neuropathy.

In some embodiments, the present invention provides a method of treating a vasomotor symptom disorder comprising administering to a patient in need thereof a therapeutically effective amount of a compound of Formula I, or pharmaceutically acceptable salt or prodrug thereof. In some embodiments of the method, the compound has Formula I-A. In some embodiments of the method, the compound has Formula I-B. In some embodiments of the method, the compound has Formula I-C. In some embodiments of the method, the compound has Formula I-D. The method can include all of the embodiments for the compounds of Formulas I, I-A, I-B, I-C, and I-D hereinbefore described, including various combinations and subcombinations of the embodiments.

As used herein, the term "vasomotor symptom disorder" refers to symptoms and/or pathology associated with the nerves or muscles that cause the blood vessels to constrict or dilate.

In some embodiments, the vasomotor symptom disorder is hot flushes or night sweats.

The disorders specified in the embodiments herein can fall into one or more of the defined disorders, and are not restricted to one particular classification. For example, Parkinson's disease can be classified as either a neurodegenerative disorder or a movement disorder.

As used herein, the term "patient" refers to any animal, including mammals, preferably mice, rats, other rodents, rabbits, dogs, cats, swine, cattle, sheep, horses, or primates, and most preferably humans. The patient may be an adult, child, or infant.

The phrase "therapeutically effective amount" refers to the amount of a compound of the invention that elicits the biological or medicinal response in a tissue, system, animal, individual, patient, or human that is being sought by a researcher, veterinarian, medical doctor or other clinician. The desired biological or medicinal response may include preventing the disorder in a patient (e.g., preventing the disorder in a patient that may be predisposed to the disorder, but does not yet experience or display the pathology or symptomatology of the disease). The desired biological or medicinal response may also include inhibiting the disorder in a patient that is experiencing or displaying the pathology or symptomatology of the disorder (i.e., arresting or slowing further development of the pathology and/or symptomatology). The desired biological or medicinal response may also include ameliorating the disorder in a patient that is experiencing or displaying the pathology or symptomatology of the disease (i.e., reversing the pathology or symptomatology).

The therapeutically effective amount provided in the treatment of a specific disorder will vary depending the specific disorder(s) being treated, the size, age, and response pattern of the patient, the severity of the disorder(s), the judgment of the attending clinician, the manner of administration, and the purpose of the administration, such as prophylaxis or therapy. In general, effective amounts for daily oral administration may be about 0.01 to 50 mg/kg, preferably about 0.1 to 10 mg/kg and effective amounts for parenteral administration may be about 0.01 to 10 mg/kg, preferably about 0.1 to 5 mg/kg.

The compounds of the invention may be administered orally or parenterally, neat or in combination with one or more conventional pharmaceutically acceptable carriers or excipients. Accordingly, the present invention provides a pharmaceutical composition which comprises a compound of Formula I, or a pharmaceutically salt or prodrug thereof, and a pharmaceutically acceptable carrier. In some embodiments, the pharmaceutical composition comprises a compound of Formula I-A, or a pharmaceutically acceptable salt or prodrug thereof, and a pharmaceutically acceptable carrier. In some embodiments, the pharmaceutical composition comprises a compound of Formula I-B, or a pharmaceutically acceptable salt or prodrug thereof, and a pharmaceutically acceptable carrier. In some embodiments, the pharmaceutical composition comprises a compound of Formula I-C, or a pharmaceutically acceptable salt or prodrug thereof, and a pharmaceutically acceptable carrier. In some embodiments, the pharmaceutical composition comprises a compound of Formula I-D, or a pharmaceutically acceptable salt or prodrug thereof, and a pharmaceutically acceptable carrier. The pharmaceutical compositions can include all of the embodiments for the compounds of Formulas I, I-A, I-B, I-C, and I-D hereinbefore described, including various combinations and subcombinations of the embodiments.

In some embodiments, the present invention provides a compound of the invention, or pharmaceutically acceptable salt thereof. In some embodiments, the methods or pharmaceutical compositions of the invention utilize a compound of the invention, or pharmaceutically acceptable salt thereof.

Solid carriers suitable for use in the compositions of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided active ingredient. As used herein, the term "active ingredient" refers to a compound of Formula I, I-A, I-B, I-C, or I-D, or a pharmaceutically acceptable salt or prodrug thereof. In tablets, the active ingredient may be mixed with a carrier having the necessary compression properties in suitable proportions and compacted in the shape and size desired. The powders and tablets may contain up to 99% by weight of the active ingredient. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the compositions of the invention. The active ingredient may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate. Sterile liquid carriers can be used in sterile liquid form compositions for parenteral administration. The liquid carrier for pressurized compositions can be halogenated hydrocarbon or other pharmaceutically acceptable propellant.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

The compounds of the invention can be administered rectally or vaginally in the form of a conventional suppository. For administration by intranasal or intrabronchial inhalation or insufflation, the compounds of the present invention can be formulated into an aqueous or partially aqueous solution, which can then be utilized in the form of an aerosol. The compounds of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

The pharmaceutical composition can be administered in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C NMR) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the present invention can be prepared, in part, by the methods described by Makosa and Wojciechowski (Wojciechowski, K; Makosza, M. *Synthesis* 1986, 651-653) and by Reinhoudt and co-workers (Orlemans, E. O. M.; Schreuder, A. H.; Conti, P. G. M.; Verboom, W.; Reinhoudt, D. N. *Tetrahedron* 1987, 43, 3817-3826), both of which are incorporated herein by reference in their entireties. Alternatively, the compounds of the present invention can be prepared by introducing a 3-phenylsulfide group onto an indole using the procedures described in Jain, S.; Shukla, K.; Mukhopadhyay, A.; Suryawanshi, S. N.; Bhakuni, D. S. *Synthetic Communications*, 1990, 20, 1315-1320, incorporated herein by reference in its entirety, followed by oxidation to a 3-arylsulfonylindole as described in Garcia, J.; Greenhouse, R.; Muchowski, F. J. M.; Ruiz, J. A., *Tetrahedron Letters* 1985, 26, 1827-1830, incorporated herein by reference in its entirety. These two approaches are the basis for parts of Schemes 1 and 2.

Compounds of Formula I (wherein A is $C_{2-5}$ alkylene) may be made as outlined in Scheme 1. In step 1, compounds of Formula IV can be formed by vicarious nucleophilic substitution using compounds of Formula II and Formula III. Compounds of Formula III are commercially available or readily made by one skilled in the art using methods as described by M. Makosza and J. Golinski in *J. Org. Chem.* 1984, 49, 1488-1494, incorporated herein by reference in its entirety, or other methods. The vicarious nucleophilic substitution of step 1 is typically performed by treating a compound of Formula II with a compound of Formula III in a solvent (e.g., THF or DMSO) at ambient temperature or below. The mixture is then treated with two or more equivalents of a strong base (e.g., KO$^t$Bu or powdered KOH) which will afford compounds of Formula IV. The preferred conditions for step 1 utilize THF as solvent, KO$^t$Bu as base, and temperatures between –78° C. and –20° C.

In step 2, compounds of Formula V are formed by treating compounds of Formula IV with a reducing agent such as Fe(0), Zn(0), or Sn(0) in the presence of a solvent and an acid, such as acetic acid or concentrated hydrochloric acid. Alternatively, the conditions for step 2 may employ catalytic hydrogenation utilizing either Raney nickel or platinum on sulfided carbon. The preferred conditions for step 2 depend upon the starting substrate and include catalytic hydrogenation or use of SnCl$_2$ in ethyl acetate at a reflux temperature of 95° C.

In step 3, compounds of Formula VI are formed by heating compounds of Formula V with an appropriate orthoformate (i.e., R$^3$C(O-alkyl)$_3$), such as triethyl orthoformate or triethyl orthoacetate, and a catalytic acid. Typical reaction conditions for step 3 utilize para-toluenesulfonic acid as a catalytic acid and the reaction mixture is heated to reflux for several hours. Compounds of Formula VI are typically isolated, but may be carried on without purification or characterization to avoid potential hydrolysis of the iminoether moiety.

In step 4, compounds of Formula VII are formed by treating compounds of Formula VI with a base in an appropriate solvent. Typically, THF is used as a solvent with KO$^t$Bu as the base. Alternatively, KOH may be used as a base in DMSO solvent.

In step 5, compounds of Formula VIII can be formed by Stille coupling from compounds of Formula VII. In a typical process for step 5, a compound of Formula VII is reacted with an appropriately substituted stannane in the presence of a Pd(0) catalyst at the reflux temperature of the solvent (e.g., toluene or benzene).

In step 6, compounds of Formula IX having a terminal hydroxyl group are formed by a one pot hydroboration followed by oxidation in THF. Typically compounds of Formula VIII are dissolved in anhydrous THF and cooled to 0° C., and then BH$_3$-THF complex is added. After stirring for several hours a mixture of 10% NaOH and 30% hydrogen peroxide is added to form compounds of Formula IX.

In step 7, compounds of Formula X are formed by conversion of the hydroxyl group of compounds of Formula IX to a leaving group (LG). Appropriate reaction conditions for step 7 will vary widely depending on the choice of leaving group (LG). Such methods of conversion are well known to persons skilled in the art.

In step 8, compounds of Formula I, where R$^4$ is H, are formed by displacing the leaving group (LG) of the compounds of Formula X with an amine of formula HNR$^5$R$^6$. Step 8 is typically carried out by reacting compounds of Formula X with an excess of the amine in an appropriate solvent such as THF. Optionally, in step 9, the compound from step 8 may be directly alkylated, using an alkylating agent of formula R$^4$-LG, to give a compound of Formula I, where R$^4$≠H. Step 9 is typically performed using a base, such as NaOH or KOH, in an appropriate solvent. Step 9 may also include a phase transfer catalyst such as tetrabutylammonium chloride. Typically, LG is a leaving group, such as a chlorine, bromine, or iodine atom, or an activated hydroxyl group such as a tosyl alcohol (p-toluenesulfonyloxy leaving group).

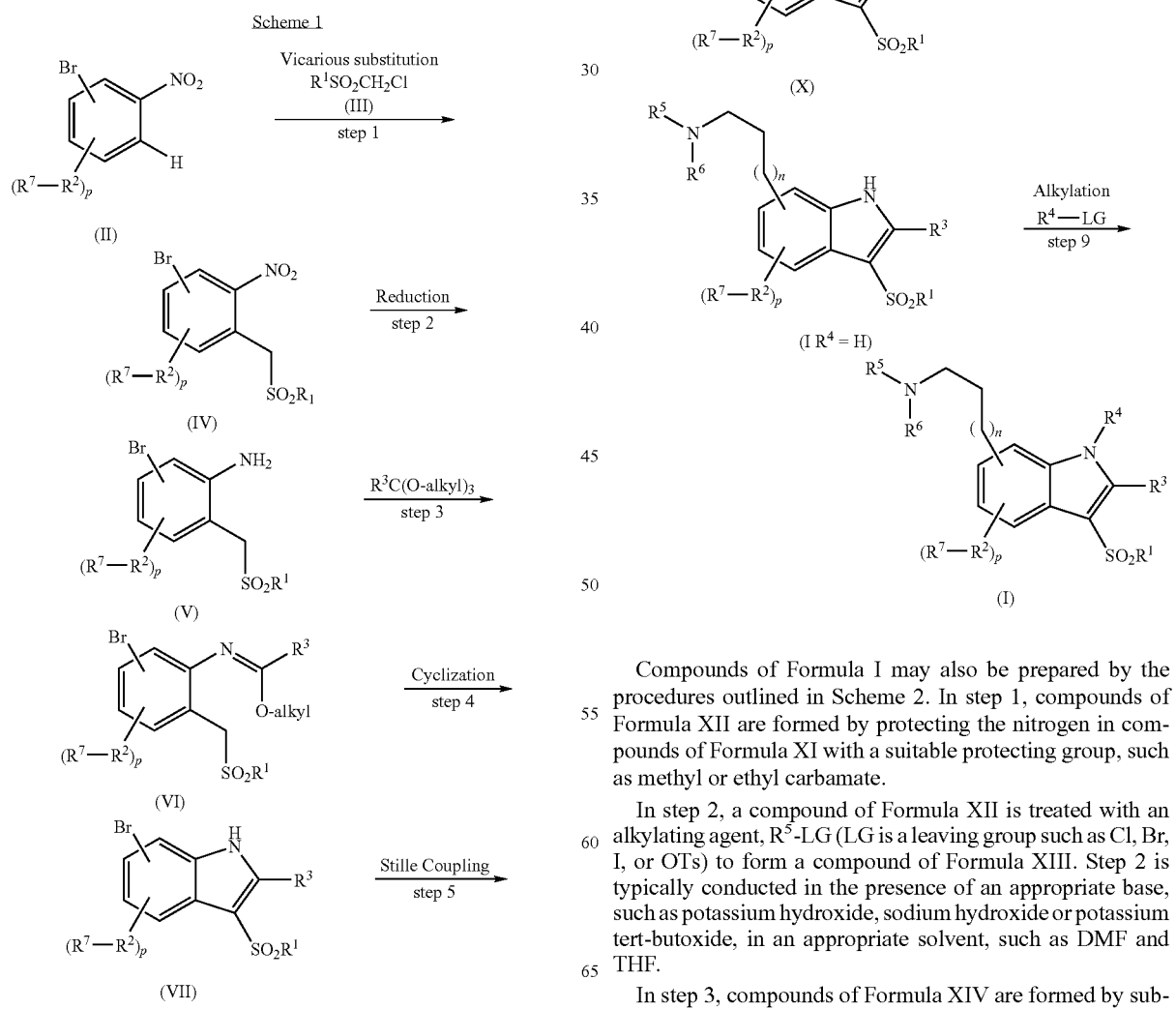

Compounds of Formula I may also be prepared by the procedures outlined in Scheme 2. In step 1, compounds of Formula XII are formed by protecting the nitrogen in compounds of Formula XI with a suitable protecting group, such as methyl or ethyl carbamate.

In step 2, a compound of Formula XII is treated with an alkylating agent, R$^5$-LG (LG is a leaving group such as Cl, Br, I, or OTs) to form a compound of Formula XIII. Step 2 is typically conducted in the presence of an appropriate base, such as potassium hydroxide, sodium hydroxide or potassium tert-butoxide, in an appropriate solvent, such as DMF and THF.

In step 3, compounds of Formula XIV are formed by subjecting compounds of Formula XIII to vicarious nucleophilic displacement through treatment with a compound of Formula III in a solvent (e.g., THF or DMSO) at ambient temperature or below. The mixture is then treated with two or more equivalents of a strong base, typically KO$^t$Bu or powdered KOH, which will afford compounds of Formula XIV. Compounds of Formula III are commercially available or readily made by one skilled in the art using methods as described by M. Makosza and J. Golinski in *J. Org. Chem.* 1984, 49, 1488-1494, incorporated herein by reference in its entirety, or other methods. The preferred conditions for effecting step 3 are THF as solvent, KO$^t$Bu as base, and temperatures between −60° C. and −20° C.

In step 4, compounds of Formula XV are formed by treating compounds of Formula XIV with a reducing agent, such as Fe(0), Zn(0), or Sn(0), in the presence of a solvent and an acid, such as acetic acid or concentrated hydrochloric acid. Alternatively, the conditions for step 4 may employ catalytic hydrogenation utilizing either Raney nickel or platinum on sulfided carbon. The preferred conditions for step 4 are catalytic hydrogenation, or use of SnCl$_2$ in ethyl acetate at a reflux temperature of 95° C. depending on starting substrate.

In step 5, compounds of formula XV are converted to the resultant indoles of Formula XVI, as previously described in Scheme 1, step 3-4. In step 6, the pendant protected amine group of the compounds of Formula XVI is deprotected to provide compounds of Formula I, where $R^4$ and $R^6$ are hydrogen. The deprotection conditions used in step 6 will vary widely depending on the initial choice of protecting group (PG). Such methods of deprotection are well known to persons skilled in the art. For example, compounds of Formula XVI (where the protecting group is methyl or ethyl carbamate) can be deprotected with hydrazine in refluxing ethylene glycol to give compounds of Formula I, where $R^4$ and $R^6$ are hydrogen.

In step 7, compounds of Formula I, where $R^6$ is not hydrogen, are formed by reductive amination. Conditions for performing this reductive amination include, but are not limited to, treatment with a substituted aldehyde in a solvent with an appropriate hydride source. Typical solvents are methanol and THF, typical hydride sources are sodium cyanoborohydride, sodium triacetoxy borohydride, and sodium borohydride. Optionally, the product of step 7 can be directly alkylated, using an alkylating agent of formula $R^4$-LG, to give a compound of Formula I, where $R^4 \ne H$, as in Scheme I, step 9 (vide supra).

Scheme 2

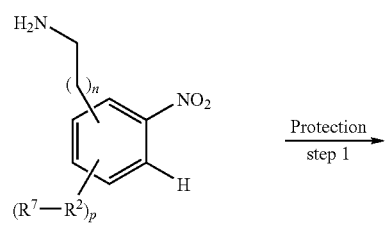

(XI)

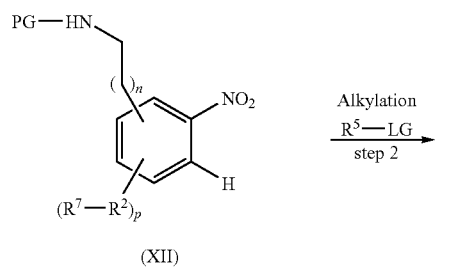

(XII)

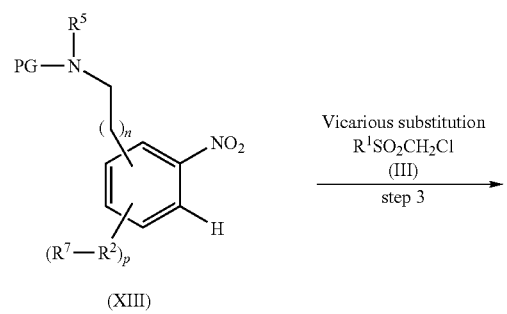

(XIII)

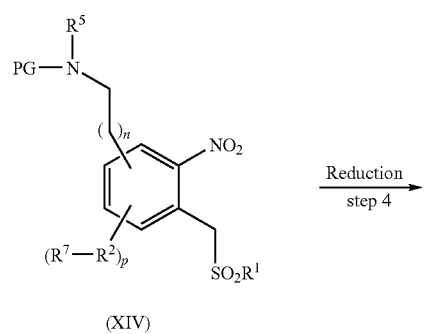

(XIV)

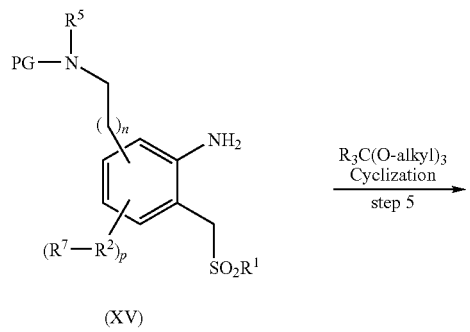

(XV)

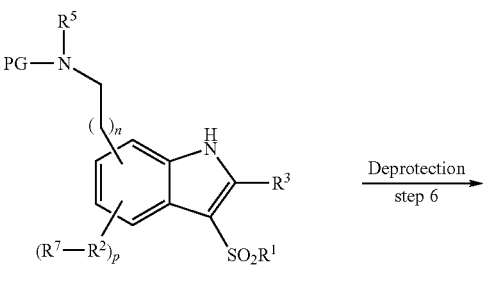

(XVI)

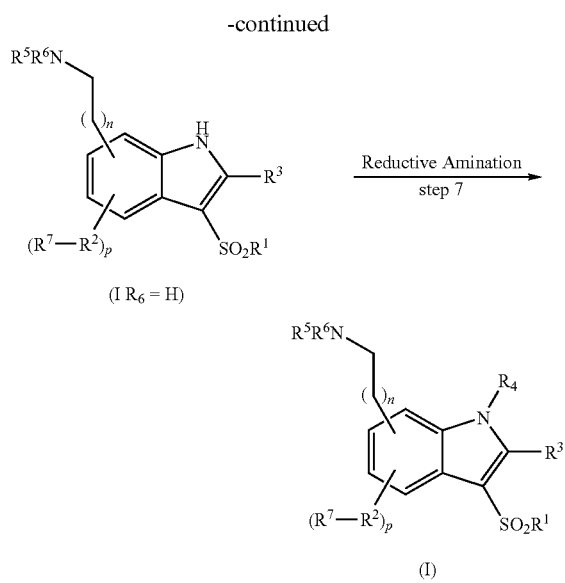

An alternative preparation of compounds of Formula I is shown in Scheme 3. In step 1, compounds of Formula XVIII are formed by treating commercially available substituted bromo indoles of Formula XVII with substituted thiophenols or alkylthiols in ethanol with a mixture of iodine and potassium iodide. In step 2, compounds of Formula VII are formed by oxidation of compounds of Formula XVIII, typically using meta-chloroperbenzoic acid as an oxidizing agent. The compounds of Formula VII are then modified as described in Scheme 1, steps 5-8, and optionally step 9 (vide supra) to provide compounds of Formula I.

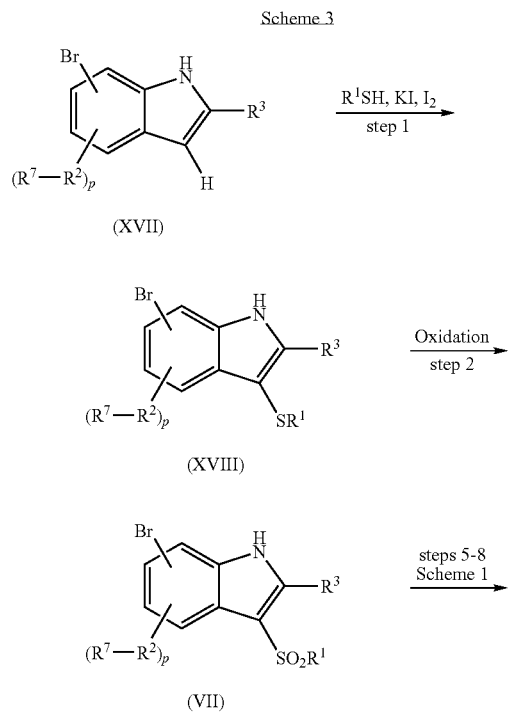

An alternative preparation of compounds of Formula I is shown in Scheme 4. In step 1, compounds of Formula XX are formed by Horner-Emmons reaction of a formyl indole of Formula XIX. Preferably, compounds of Formula XIX are treated with triethylphosphonoacetate in the presence of a suitable base, typically sodium or potassium carbonate, at temperatures ranging from room temperature to about 100° C. in a suitable solvent such as THF or 1,4-dioxane. Formyl indoles of Formula XIX are either available from commercial sources or can be synthesized through methods well established in the literature.

In step 2, compounds of Formula XXI are formed by treating a compound of Formula XX with a reducing agent, such as diisobutylaluminum hydride or lithium aluminum hydride, in the presence of a solvent, such as THF or diethyl ether. In step 3, a compound of Formula XXII is formed by hydrogenation of the double bond in a compound of Formula XXI. Preferably, compounds of Formula XXI are hydrogenated in the presence of a suitable catalyst, such as palladium on activated carbon, to give compounds of Formula XXII.

In step 4, compounds of Formula XXIII are formed by treating compounds of Formula XXII with substituted thiophenols or alkylthiols in ethanol in the presence of a mixture of iodine and potassium iodide. In step 5, compounds of Formula XXIII can be oxidized, typically using meta-chloroperbenzoic acid or OXONE® (supplied by DuPont, potassium peroxymonosulfate as active ingredient), to give compounds of Formula IX (n=1). The compounds of Formula IX can then be converted to the compounds of Formula I, as described in Scheme 1, steps 7-8 (vide supra). Optionally, the product of steps 7-8 can be directly alkylated, using an alkylating agent of formula $R^4$-LG, to give a compound of Formula I, where $R^4 \neq H$, as in Scheme I, step 9 (vide supra).

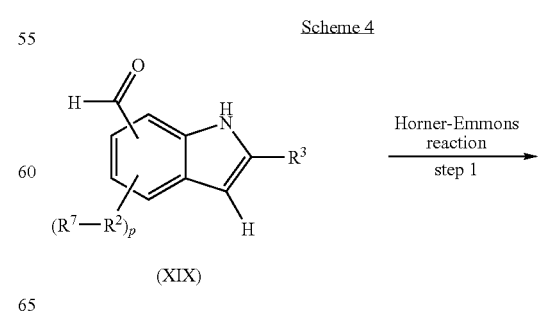

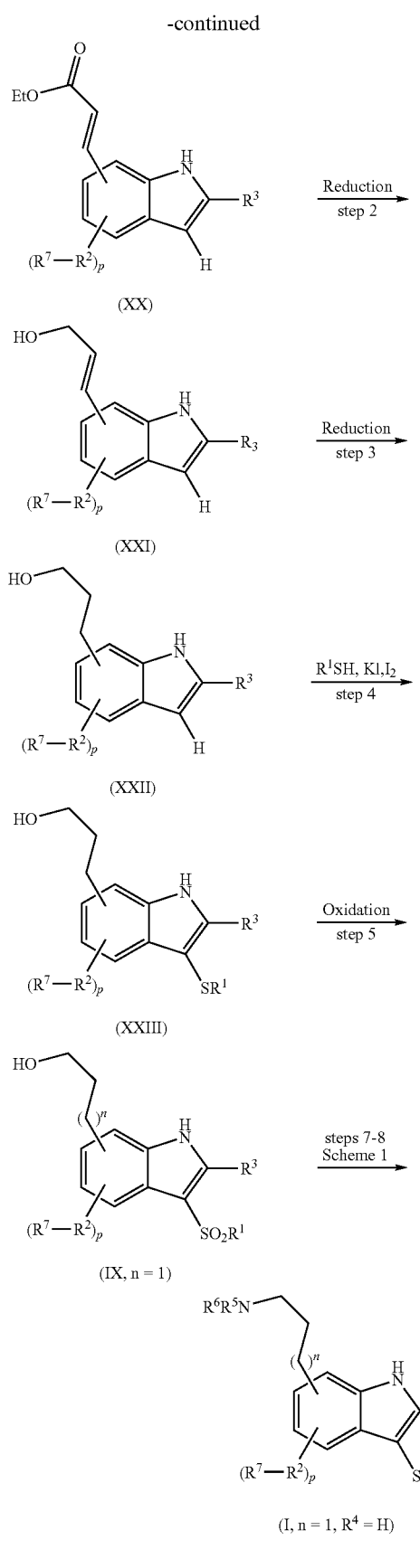

Compounds of Formula I, where A is an alkenylene group, can be synthesized as shown in Scheme 5. In step 1, compounds of Formula XXIV having a pendant alkenylene group are formed by a Heck coupling reaction by treating compounds of Formula IV with an appropriate vinyl compound, such as methyl acrylate, in the presence of a catalyst and a weak base. Typically, methyl acrylate and a compound of Formula IV are reacted in DMF in the presence of a catalytic amount of palladium acetate and triphenylphosphine and 1.25 equivalents of diisopropylamine, at 100° C. for 8-12 hours. In step 2, compounds of Formula XXV are formed by reduction of the ester and nitro groups of compounds of Formula XXIV using suitable reducing agents such as diisobutylaluminum hydride and Fe(0), Zn(0), or Sn(0), in the presence of a solvent and an acid such as acetic acid or concentrated hydrochloric acid.

Compounds of Formula XXV are then converted to indoles of Formula XXVI using the methods described for Scheme 1, steps 3-4 (vide supra). Compounds of Formula XXVI are then transformed to compounds of Formula I, wherein A is an alkenylene group, by the methods described for Scheme 1, steps 7-8, and, optionally step 9 (vide supra).

Scheme 5

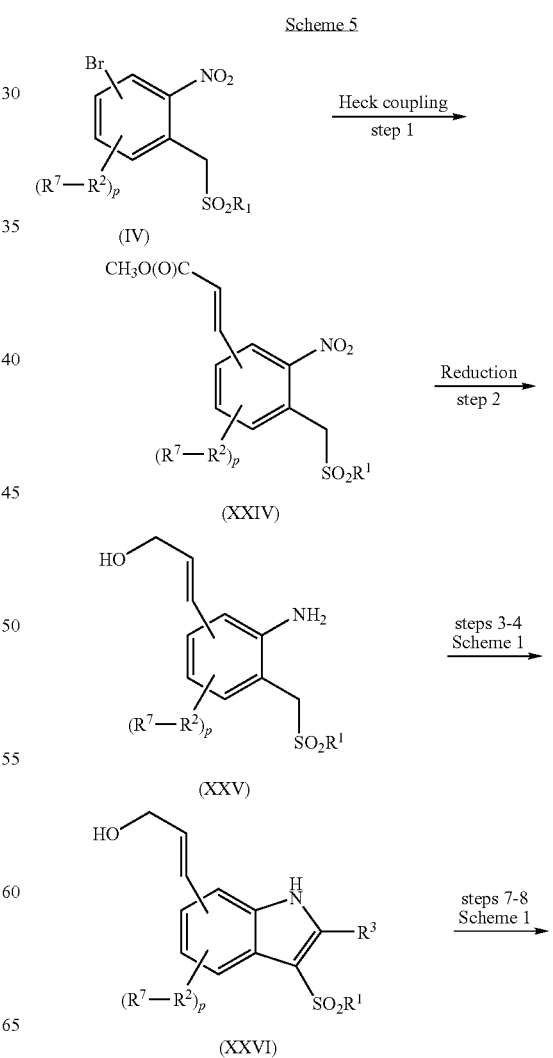

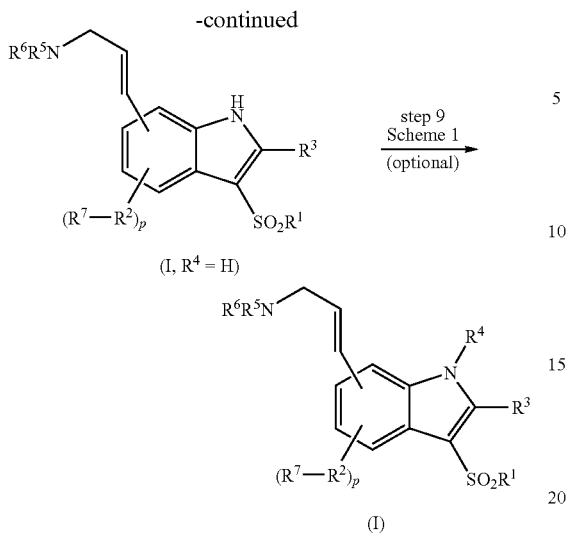

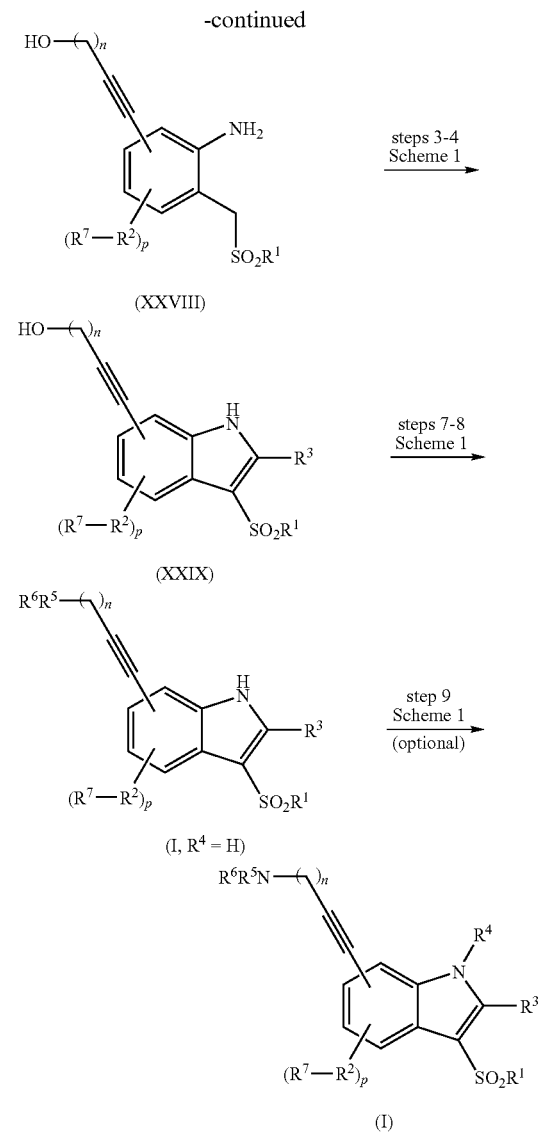

Compounds of Formula I, where A is an alkynylene group, can be synthesized as shown in Scheme 6. In step 1, compounds of Formula XXVII having a pendant alkynylene group are formed by a Sonagashira coupling reaction by treating compounds of Formula IV with an appropriate substituted alkyne, such as propargyl or homo propargyl alcohol, in the presence of a catalyst. Step 1 is typically carried out by reacting the substituted alkyne with a compound of Formula IV in toluene in the presence of five equivalents of diisopropyl amine and a catalytic amount of tetrakis(triphenylphosphine)palladium and copper(I) iodide at 90° C.

In step 2, compounds of Formula XXVIII are formed by reduction of the nitro group of compounds of Formula XXVII with a reducing agent. Step 2 is typically carried out by reacting the compound of Formula XXVII with $SnCl_2$ in ethyl acetate at reflux temperature.

Compounds of Formula XXVIII are then converted to indoles of Formula XXIX using the methods described for Scheme 1, steps 3-4 (vide supra). Compounds of Formula XXIX are then transformed to compounds of Formula I, wherein A is an alkynylene group, by the methods described for Scheme 1, steps 7-8, and, optionally step 9 (vide supra).

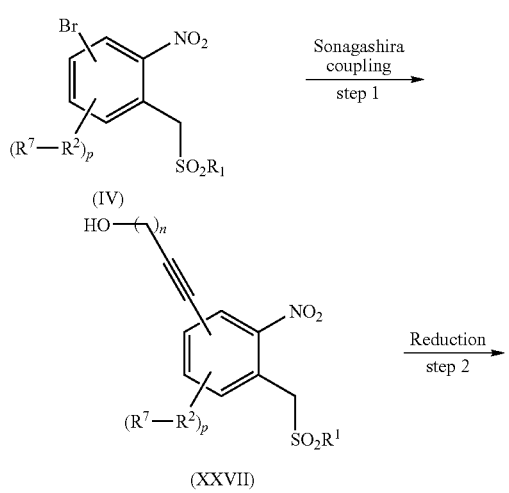

In order that the invention disclosed herein may be more efficiently understood, examples are provided below. It should be understood that these examples are for illustrative purposes only and are not to be construed as limiting the invention in any manner.

EXAMPLES

The following abbreviations are used herein: "DMF" is dimethylformamide; "THF" is tetrahydrofuran; "DMSO" is dimethylsulfoxide; "TEA" is triethylamine; "DCE" is 1,2-dichloroethane; "MCPBA" is meta-chloroperbenzoic acid; "EDTA" is ethylene diamine tetraacetic acid; "EA" is elemental analysis; "MS" is mass spectroscopy; "NMR" is nuclear magnetic resonance; "O$^t$Bu" is tert-butoxide; "Et" is ethyl; "Me" is methyl; "Bn" is benzyl; "Ph" is phenyl; "Bu" is butyl; "tBu" or "$^t$Bu" is tert-butyl; "Ac" is acetyl; "OTs" is a O-tosyl(p-toluenesulfonyloxy) group; "Ra Ni" is Raney nickel; "py" is pyridine; "Dec" is decomposition; "Mp" is melting point; and "min" is minute(s).

As used herein, the term "chromatography" generally refers to flash chromatography on silica gel. As used herein, "E" refers to the solvent ethyl acetate and "H" refers to the solvent hexane(s). As used herein, "E:H" refers to volume:volume mixtures of E and H generally used as chromatography solvent. All products are characterized by EA, MS and $^1$H NMR unless otherwise noted. As used herein, the term "brine" refers to saturated aqueous NaCl.

As used herein, the term "[3H]-LSD" refers to tritiated lysergic acid. As used herein, the term "MDCK-Net6" refers to Madin-Darby canine kidney. As used herein, the term "FBS" refers to fetal bovine serum. As used herein, the term "HEPES" refers to 4-(2-hydroxyethyl)-1-piperazineethanesulfonic acid. As used herein, the term "FLIPR" refers to Fluorometric Imaging Plate Reader. As used herein, the term "cDNA" refers to complimentary DNA. As used herein, the term "CHO cells" refers to chinese hamster ovary. As used herein, the term "PBS" refers to phosphate buffered saline. As used herein, the term "DOI" refers to 1-(2,5-Dimethoxy-4-iodophenyl)-2-aminopropane hydrochloride. As used herein, the term "HBSS" refers to Hank's Balanced Salt Solution. As used herein, the term "hNET" refers to human norepinephrine transporter. As used herein, the term "MDL" refers to MDL 100907, ((R)-α-(2,3-dimethoxyphenyl)-1-[2-(4-fluorophenyl)ethyl]-4-piperidinemethanol). As used herein, the term "Tris.HCl" refers to Tris(hydroxymethyl)aminomethane hydrochloride. As used herein, the term "DMEM" refers to Dulbecco's Modified Eagle Medium.

In mass spectral data, MS(ES+) refers to positive electrospray which generally gives a peak for M+H while MS(ES−) refers to negative electrospray which generally gives a peak for M−H. Melting points (mp) are uncorrected. Reactions are run under nitrogen atmosphere with stirring unless noted otherwise. Ambient temperature is assumed to be between 15° C. and 20° C.

The definitions of terms provided herein and throughout the application refer to every reference to said terms throughout the present application and are not intended to be restricted to one particular embodiment of the invention, unless otherwise indicated.

Example 1

N,N-DIMETHYL-N-{2-[3-(PHENYLSULFONYL)-1H-INDOL-5-YL]ETHYL}AMINE HYDROCHLORIDE

Step 1: Preparation of 5-bromo-2-nitrobenzyl phenyl sulfone:

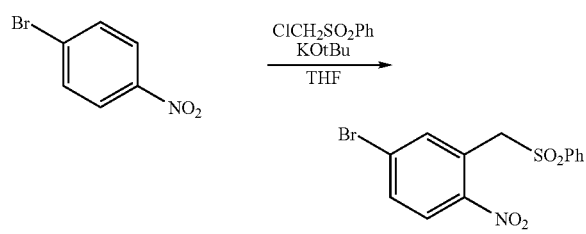

To a stirred solution of 1-bromo-4-nitrobenzene (5.05 g, 25 mmol) and chloromethyl-phenylsulfone (4.76 g, 25 mmol) in dry THF (50 mL) at −65° C. under nitrogen is added 1.0M KO$^t$Bu in THF (55 mL, 55 mmol). The deep purple reaction is allowed to warm to 0° C. over 1.5 hours and then treated with glacial acetic acid (4 mL). The reaction is diluted with water (100 mL) and saturated aqueous NaHCO$_3$ (100 mL), and then extracted with CH$_2$Cl$_2$ (2×200 mL). The extracts are dried (MgSO$_4$) and concentrated in vacuo to a light orange solid. Trituration with ethyl acetate and hexanes affords the title compound as a pale yellow solid (6.45 g, 72%). Mp: 143-144° C. MS (ES−): 354 (M−H).

Step 2: Preparation of 4-bromo-2-[(phenylsulfonyl)methyl]aniline:

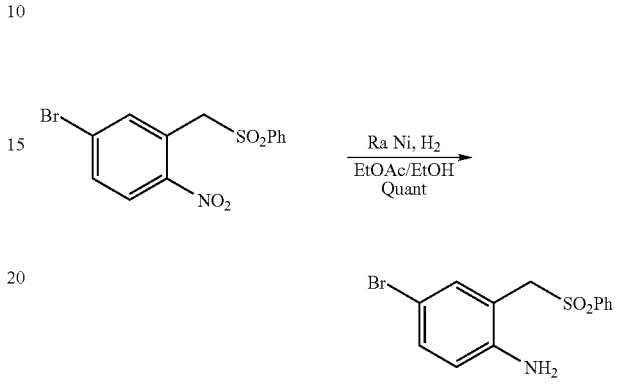

This compound was prepared by catalytic hydrogenation of 5-bromo-2-nitrobenzyl phenyl sulfone (0.23 g, 0.64 mmol) in the presence of Raney nickel and hydrogen (45 psi) in ethyl acetate (30 ml) for 1 hour. The reaction mixture is filtered through celite and concentrated in vacuo to give the title compound as a light brown solid (0.21 g, 99%). Mp: 140-141° C. MS (ES+): 326 (M+H).

Step 3: Preparation of 5-bromo-3-(phenylsulfonyl)-1H-indole:

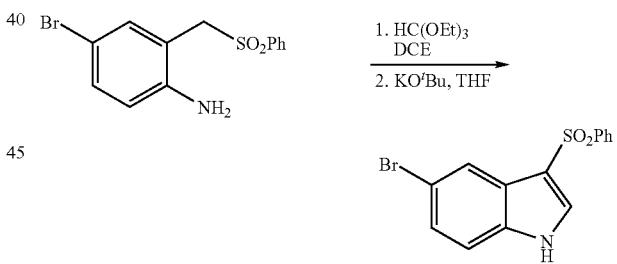

A stirred solution of 4-bromo-2-[(phenylsulfonyl)methyl] aniline (3.26 g, 10.00 mmol, p-toluenesulfonic acid monohydrate (0.20 g), triethyl orthoformate (8.32 mL, 50 mmol) and 1,2-dichloroethane (70 mL) is heated at reflux under nitrogen for 5 hours and then at room temperature for 16 hours. The reddish reaction is concentrated in vacuo to a red oil. The resulting crude intermediate iminoether is stirred in dry THF (50 mL) and treated with 1.0M KO$^t$Bu in THF (13 mL, 13 mmol). After 5 min, a tan precipitate is evident. After 1 hour, the reaction is treated with water (30 mL) and NH$_4$Cl (0.60 g), extracted with CH$_2$Cl$_2$ (150 mL), dried (MgSO$_4$), filtered and concentrated in vacuo to a light orange solid. Trituration with ethyl acetate and hexanes affords the title compound as a light orange solid (2.78 g, 72%). Mp: 176-178° C. MS (ES−): 334 (M−H).

Step 4: Preparation of 3-(phenylsulfonyl)-5-vinyl-1H-indole:

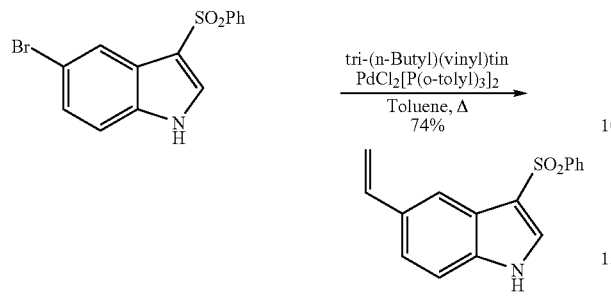

5-bromo-3-(phenylsulfonyl)-1H-indole (505 mg, 1.50 mmol) and dichlorobis(tri-o-tolylphosphine)-palladium(II) (118 mg, 0.09 mmol) were dissolved in toluene (5 mL) and stirred for 10 minutes at room temperature under a nitrogen atmosphere. Tributyl(vinyl)tin (619 mg, 1.95 mmol) was added and the mixture was refluxed for 1 hour. The mixture was cooled to room temperature, diluted with ethyl acetate (10 mL), 1 M KF (5 mL) and stirred for 12 hours. The resultant tin salt precipitate is removed by suction filtration and the organic layer was washed with water (5 mL), then brine and dried over MgSO$_4$, filtered and concentrated in vacuo. Purification by flash chromatography (40% ethyl acetate/petroleum ether) gave the title compound as a white solid (313 mg, 74%). Mp: 140-145° C. MS (ES+): 284 (M+H).

Step 5: Preparation of 2-[3-(phenylsulfonyl)-1H-indol-5-yl]ethanol:

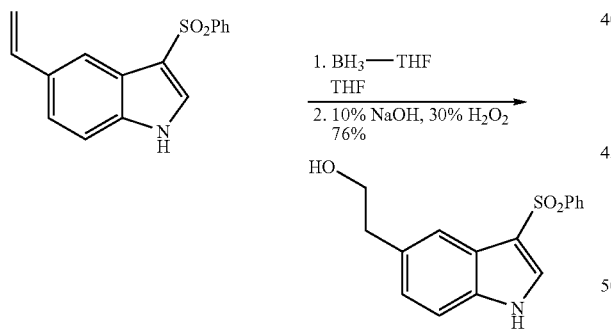

To a solution of 3-(phenylsulfonyl)-5-vinyl-1H-indole (1.9 g, 6.7 mmol) in THF (10 mL) at 0° C. was added dropwise BH$_3$-THF (6.7 mL of 1 M THF solution, 6.7 mmol). The solution was stirred for 3 hours at 0° C., and H$_2$O (7 mL) was added slowly. To this mixture was added 10% NaOH (10 mL), 30% H$_2$O$_2$ and the mixture was stirred vigorously at room temperature for 15 hours. The mixture was partitioned between ethyl acetate and H$_2$O, and the aqueous layer was extracted with ethyl acetate (2×25 mL). The combined organic layers were washed with brine, dried (MgSO$_4$), filtered and concentrated under reduced pressure. Silica gel chromatography (50% ethyl acetate/dichloromethane) gave the title compound as a white solid (1.5 g, 76%). Mp: 55-60° C. MS (ES−): 300 (M−H)

Step 6: Preparation of 2-[3-(phenylsulfonyl)-1H-indol-5-yl]ethyl 4-methylbenzenesulfonate

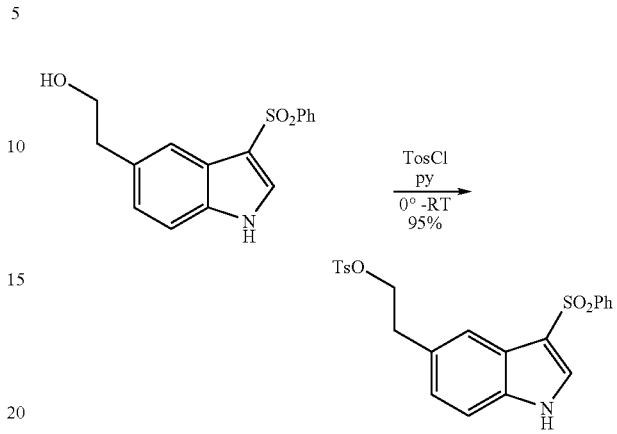

To a solution of 2-[3-(phenylsulfonyl)-1H-indol-5-yl]ethanol (0.88 g, 2.91 mmol) in anhydrous pyridine (15 mL) at 0° C. was added toluenesulfonyl chloride (0.58 g, 3.05 mmol). The solution was stirred for 12 hours at room temperature. The mixture was partitioned between ethyl acetate and H$_2$O, and the aqueous layer was extracted with ethyl acetate (3×30 mL). The combined organic layers were washed with 2 M HCl, (2×25 mL), brine, dried (MgSO$_4$), filtered and concentrated under reduced pressure. Silica gel chromatography (50% ethyl acetate/dichloromethane) gave the title compound as a white solid (1.3 g, 95%). Mp: 60-63° C. MS (ES−): 454 (M−H).

Step 7: Preparation of N,N-dimethyl-N-{2-[3-(phenylsulfonyl)-1H-indol-5-yl]ethyl}amine hydrochloride:

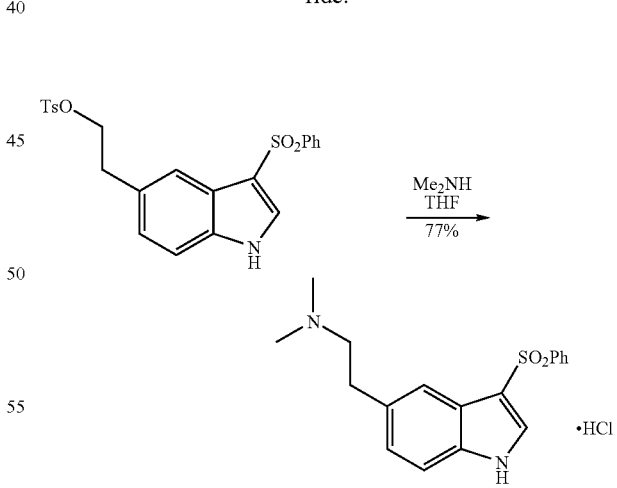

A solution of 2-[3-(phenylsulfonyl)-1H-indol-5-yl]ethyl 4-methylbenzenesulfonate (0.09 g, 0.198 mmol) in anhydrous THF (2 mL) was added an excess of dimethylamine (0.4 mL of 2 M THF solution, 0.79 mmol) and heated to 71° C. for 24 hours. The mixture was partitioned between ethyl acetate and H$_2$O, and the aqueous layer was extracted with ethyl acetate (10 mL). The combined organic layers were washed with 2 M NaOH, (2×15 mL), brine, dried (MgSO₄), filtered and concentrated under reduced pressure. Silica gel chromatography (10% EtOH/2N ammonia/dichloromethane) gave the title compound as a white solid (0.05 g, 77%). This solid was dissolved in diethyl ether and treated with 1 N HCl in diethyl ether (0.16 mL, 0.16 mmol) to afford a white precipitate isolated by vacuum filtration. Mp: 251° C. MS (ES+): 329 (M+H).

Examples 2-11

In an analogous fashion to that described in Example 1, step 7, substituting the appropriate displacing amine, the following examples are prepared.

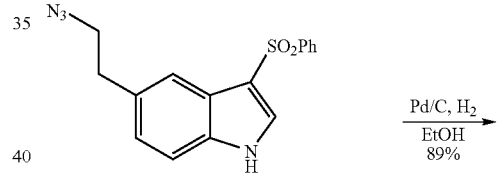

| Example | R⁵ | R⁶ | Mp (° C.) | MS | Appearance |
|---|---|---|---|---|---|
| 2 | H | Propyl | 189-192 | (M + H) 343 | White solid |
| 3 | H | Isopropyl | 263 | (M + H) 343 | White solid |
| 4 | H | Cyclopropyl | 205-208 | (M + H) 341 | Light pink solid |
| 5 | H | Cyclopentyl | 252 | (M + H) 369 | Tan solid |
| 6 | H | Benzyl | 215-220 | (M + H) 391 | Tan solid |
| 7 | Me | Et | 203 | (M + H) 343 | White solid |
| 8 | Et | Et | 193-195 | (M + H) 357 | White solid |
| 9 | Pyrrolidin-1-yl | | 230-232 | (M + H) 355 | White solid |
| 10 | Piperidin-1-yl | | 272 | (M + H) 369 | White solid |
| 11 | Morpholin-4-yl | | 250-255 | (M + H) 371 | White solid |

Example 12

{2-[3-(phenylsulfonyl)-1H-indol-5-yl]ethyl}amine hydrochloride

Step 1: Preparation of 5-(2-azido-ethyl)-3-benzenesulfonyl-1H-indole:

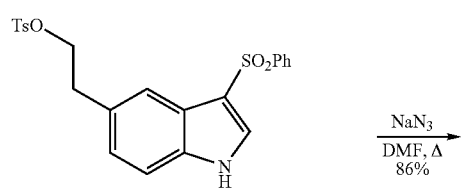

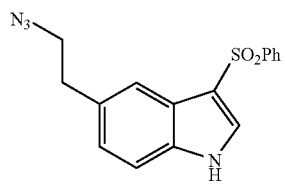

A solution of 2-[3-(phenylsulfonyl)-1H-indol-5-yl]ethyl 4-methylbenzenesulfonate (0.20 g, 0.44 mmol) in anhydrous DMF (2.5 mL) was added sodium azide (0.14 g, 2.2 mmol) and heated to 100° C. for 6 hours. The mixture was partitioned between ethyl acetate and H₂O, and the aqueous layer was extracted with ethyl acetate (10 mL). The combined organic layers were washed with brine (1×15 mL), dried (MgSO₄), filtered concentrated under reduced pressure. Silica gel chromatography (40% Ethyl acetate/petroleum ether) gave the azide as a clear glass (0.13 g, 86%) which was used directly in the next step.

Step 2: Preparation of {2-[3-(phenylsulfonyl)-1H-indol-5-yl]ethyl}amine hydrochloride:

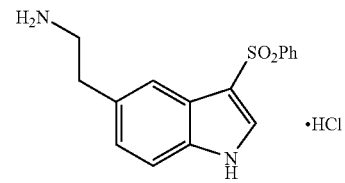

The azide (0.125 g, 0.383 mmol) was reduced by catalytic hydrogenation in the presence of palladium on carbon and hydrogen (40 psi) in ethanol (30 ml) for 1 hour. The reaction mixture was filtered through celite and concentrated in vacuo to give a white solid (0.1 g, 86%). This solid was dissolved in diethyl ether and treated with 1 N HCl in diethyl ether (0.16 mL, 0.16 mmol) to afford a white precipitate isolated by vacuum filtration. Mp: 200° C. MS (ES+): 301 (M+H).

Example 13

3-(PHENYLSULFONYL)-5-(2-PIPERAZIN-1-YL-ETHYL)-1H-INDOLE HYDROCHLORIDE

Step 1: Preparation of 5-[2-(4-benzylpiperazin-1-yl)ethyl]-3-(phenylsulfonyl)-1H-indole:

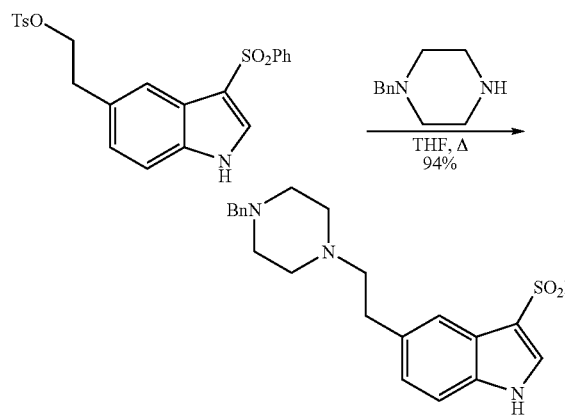

A solution of 2-[3-(phenylsulfonyl)-1H-indol-5-yl]ethyl 4-methylbenzenesulfonate (0.16 g, 0.25 mmol) in anhydrous THF (2.5 mL) was added an excess of benzyl piperazine (0.18 mL, 1.02 mmol) and heated to 71° C. for 24 hours. The mixture was partitioned between ethyl acetate and $H_2O$, and the aqueous layer was extracted with ethyl acetate (10 mL). The combined organic layers were washed with 2 M NaOH, (2×15 mL), brine, dried ($MgSO_4$), filtered and concentrated under reduced pressure. Silica gel chromatography (10% EtOH/2N ammonia/dichloromethane) gave the title compound as a light yellow solid (0.11 g, 94%). Mp: 150-153° C. MS (ES+): 460 (M+H).

Step 2: Preparation of 3-(phenylsulfonyl)-5-(2-piperazin-1-ylethyl)-1H-indole hydrochloride:

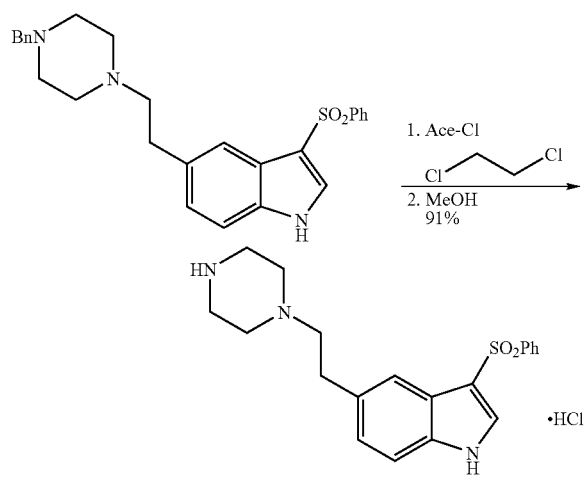

A stirred mixture of 5-[2-(4-benzylpiperazin-1-yl)ethyl]-3-(phenylsulfonyl)-1H-indole (0.110 g, 0.24 mmol) and 1-chloroethylchloroformate (0.05 mL, 0.36 mmlole) in 1,2-dichloroethane (2 mL) was heated to reflux for 12 hours. The reaction mixture was cooled and concentrated in vacuo to a brown glass. The glass was taken up in methanol (4 mL) and heated to reflux for 6 h, then cooled and concentrated in vacuo to a semi solid. This solid was dissolved in diethyl ether and treated with 1 N HCl in diethyl ether (0.22 mL, 0.22 mmol) to afford a white precipitate isolated by vacuum filtration. Mp: 220° C. MS (ES+): 370 (M+H).

Example 14

N-METHYL-N-{2-[3-(PHENYLSULFONYL)-1H-INDOL-5-YL]ETHYL}AMINE

Step 1: Preparation of methyl[2-(4-nitrophenyl)ethyl]carbamate:

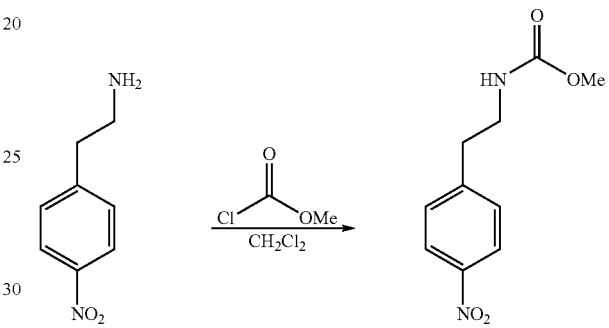

To a stirred solution of [2-(4-nitrophenyl)ethyl]amine (6.06 g, 30 mmol) in $CH_2Cl_2$ (75 ml), MeOH (5 ml), and TEA (9.5 ml) at 0° C. was added chloromethylformate (3.39 g, 36 mmol) dropwise. The reaction mixture was stirred at room temperature for 1 hour concentrated in vacuo, and partitioned between ethyl acetate and water, and the aqueous layer was extracted with ethyl acetate. The combined organic layers were washed with water (50 mL), brine (50 mL), dried ($MgSO_4$), filtered and concentrated under reduced pressure to afford a yellow solid (6.6 g, 98%). Mp: 38° C., MS (ES-): 223 (M-H).

Step 2: Preparation of methyl methyl[2-(4-nitrophenyl)ethyl]carbamate

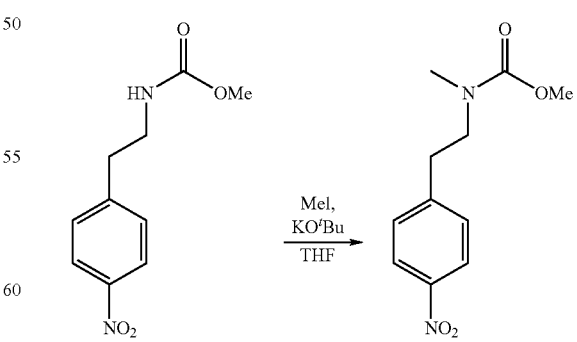

To a stirred solution of methyl[2-(4-nitrophenyl)ethyl]carbamate (224 mg, 1 mmol) in THF (2 mL) was added $KO^tBu$ (201 mg, 1.8 mmol) and MeI (256 mg, 1.8 mmol) sequentially. The reaction mixture was stirred for 12 hours at room temperature. The reaction was diluted with water (5 mL), extracted with EtOAc (2×15 mL), washed with water (5 mL), dried (MgSO₄), filtered and concentrated under reduced pressure. Silica gel chromatography (60% ethyl acetate/hexane) afforded the title compound as a semi solid (160 mg, 67.2%). MS (ES+): 239 (M+H).

Step 3: Preparation of methyl methyl(2-{4-nitro-3-[(phenylsulfonyl)methyl]phenyl}ethyl)carbamate

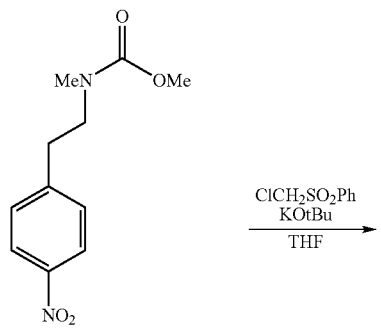

The title compound was prepared in substantially the same manner as described in Example 1, step 1 starting from methyl methyl[2-(4-nitrophenyl)ethyl]carbamate (2.47 g, 10.38 mmol), and was obtained as a white solid, (2.06 g, 51%). Mp: 42° C., MS (ES+): 393 (M+H).

Step 4: Preparation of methyl (2-{4-amino-3-[(phenylsulfonyl)methyl]phenyl}ethyl)methylcarbamate:

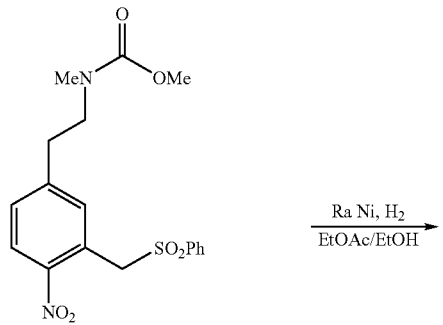

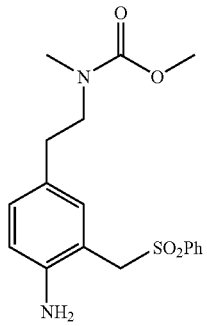

The title compound was prepared in substantially the same manner as described in Example 1, step 2 starting from methyl methyl(2-{4-nitro-3-[(phenylsulfonyl)methyl]phenyl}ethyl)carbamate (1.8 g, 4.6 mmol), and was obtained as a white solid, (1.36 g, 82%). Mp: 95-96° C. MS (ES+) 363 (M+H).

Step 5: Preparation of methyl methyl{2-[3-(phenylsulfonyl)-1H-indol-5-yl]ethyl}carbamate:

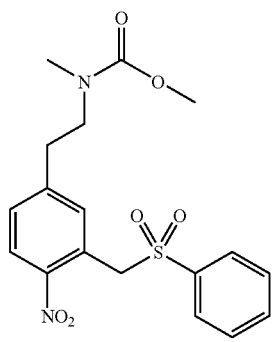

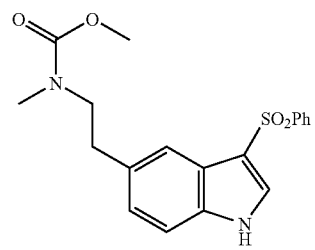

The title compound was prepared in substantially the same manner as described in Example 1, step 3 starting from methyl (2-{4-amino-3-[(phenylsulfonyl)methyl]phenyl}ethyl)methylcarbamate (350 mg, 0.97 mmol), and was obtained as a white solid, (240 mg, 66.5%). Mp: 195-197° C., MS (+) 373 (M+H).

Step 6: Preparation of N-methyl-N-{2-[3-(phenylsul-fonyl)-1H-indol-5-yl]ethyl}amine

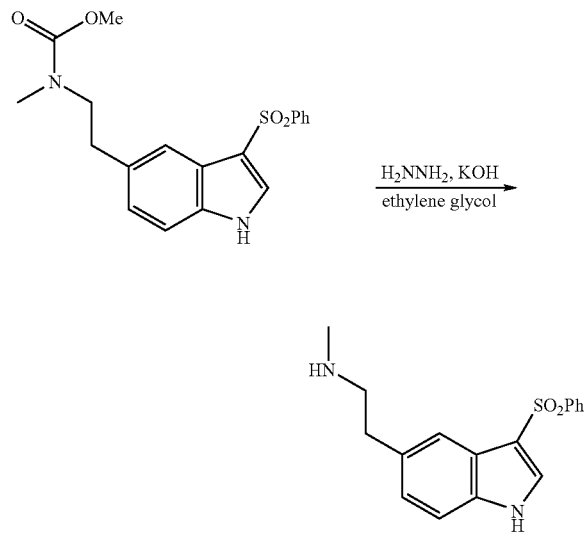

To a stirred solution of methyl methyl{2-[3-(phenylsulfonyl)-1H-indol-5-yl]ethyl}carbamate (171 mg, 0.46 mmol) in ethylene glycol (5 ml) was added $H_2NNH_2$ (147 mg, 4.6 mmol), KOH (1.9 g 13.8 mmol), and heated to 110° C. for 12 hours. The mixture was cooled to room temperature, diluted with water (5 mL) and extracted with EtOAc. The combined organic layers were washed with water (7 mL), brine (10 mL), dried (MgSO4), filtered and concentrated under reduced pressure to a residue which is triturated with $CH_2Cl_2$ to afford an off white solid, (131 mg, 93%). Mp: 151-154° C., MS (ES−) 313 (M−H).

Example 15

N-METHYL-N-{2-[2-METHYL-3-(PHENYLSULFONYL)-1H-INDOL-5-YL]ETHYL}AMINE

Step 1: Preparation of methyl methyl{2-[2-methyl-3-(phenylsulfonyl)-1H-indol-5-yl]ethyl}carbamate

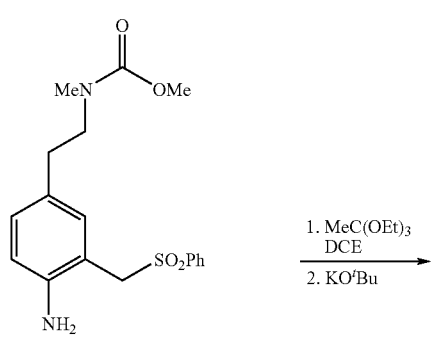

The title compound was prepared in substantially the same manner as described in Example 1, step 3 starting from methyl (2-{4-amino-3-[(phenylsulfonyl)methyl]phenyl}ethyl)methylcarbamate (160 mg, 0.44 mmol), and triethyl ortho acetate, and was obtained as a white solid. Mp: 188-191° C., MS (+) 387 (M+H).

Step 2: Preparation of N-methyl-N-{2-[2-methyl-3-(phenylsulfonyl)-1H-indol-5-yl]ethyl}amine:

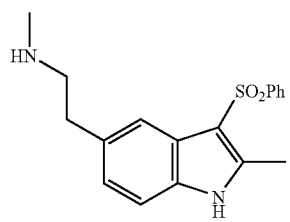

The title compound was prepared in substantially the same manner as described in Example 14, step 6 starting from methyl methyl{2-[2-methyl-3-(phenylsulfonyl)-1H-indol-5-yl]ethyl}carbamate (0.08 g, 0.2 mmol), and was obtained as a off white solid. Mp: 213-215° C. MS (ES+) 329.1 (M+H).

Examples 16-17

In an analogous fashion to that described in Example 15, steps 1 and 2, substituting the appropriate ortho formate, the following examples are prepared.

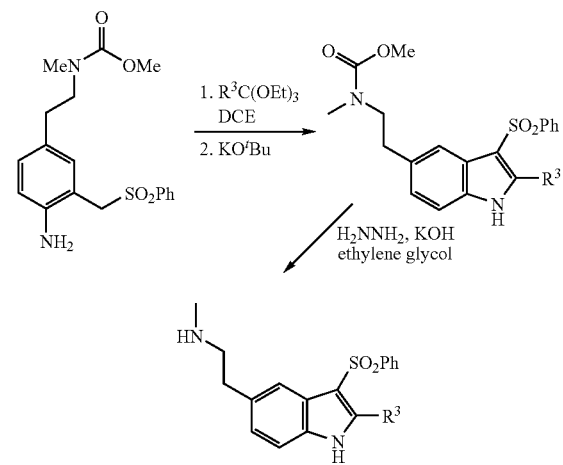

| Example | R³ | Mp (° C.) | MS | Appearance |
|---|---|---|---|---|
| 16 | Ethyl | 179-182 | (M + H) 343 | Off white solid |
| 17 | Phenyl | 180-185 | (M + H) 391.1 | Tan solid |

Example 18

N,N-DIMETHYL-N-{2-[3-(PHENYLSULFONYL)-1H-INDOL-7-YL]ETHYL}AMINE HYDROCHLORIDE

Step 1:
1-bromo-2-nitro-3-[(phenylsulfonyl)methyl]benzene:

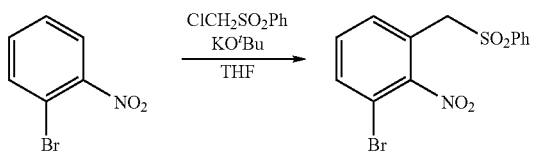

The title compound was prepared in substantially the same manner as described in Example 1, step 1 starting from 1-Bromo-2-nitro-benzene (10 g, 50 mmol), and was obtained as a tan solid, (13 g, 73%). Mp: 138-141° C. MS (ES+) 354 (M+H).

Step 2: Preparation of {2-bromo-6-[(phenylsulfonyl)methyl]phenyl}amine:

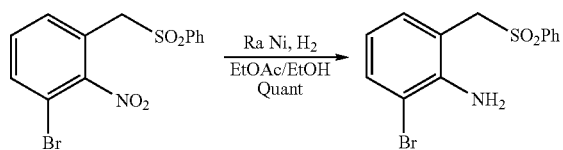

The title compound was prepared in substantially the same manner as described in Example 1, step 2 starting from 1-bromo-2-nitro-3-[(phenylsulfonyl)methyl]benzene (11.4 g, 32 mmol), and was obtained as a white solid, (10.4 g, 99%). Mp: 174-177° C. MS (ES+) 326 (M+H).

Step 3: Preparation of 7-bromo-3-(phenylsulfonyl)-1H-indole:

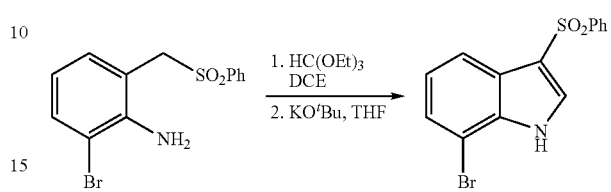

The title compound was prepared in substantially the same manner as described in Example 1, step 3 starting from {2-bromo-6-[(phenylsulfonyl)methyl]phenyl}amine (0.98 g, 3 mmol), and was obtained as a yellow foam, (0.958 g, 95%). MS (ES−) 334 (M−H).

Step 4: Preparation of 3-(phenylsulfonyl)-7-vinyl-1H-indole:

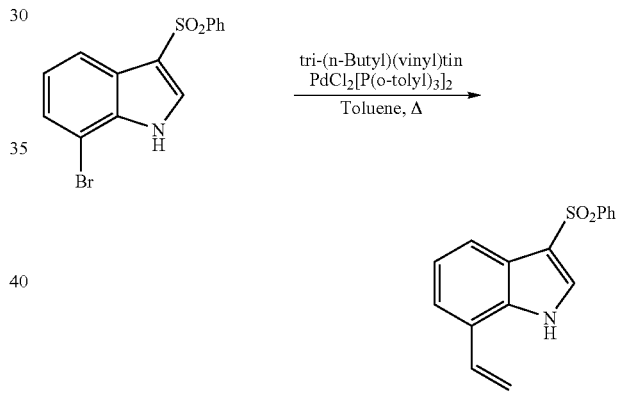

The title compound was prepared in substantially the same manner as described in Example 1, step 4 starting from 7-bromo-3-(phenylsulfonyl)-1H-indole (1.0 g, 3 mmol), and was obtained as a yellow oil, (0.663 g, 78%). MS (ES+) 284 (M+H).

Step 5: Preparation of 2-[3-(phenylsulfonyl)-1H-indol-7-yl]ethanol:

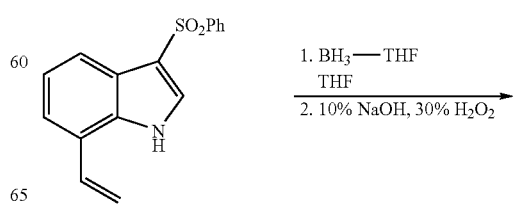

-continued

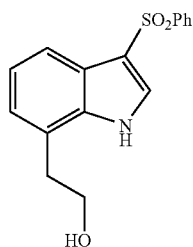

The title compound was prepared in substantially the same manner as described in Example 1, step 5 starting from 3-(phenylsulfonyl)-7-vinyl-1H-indole (0.56 g, 2 mmol), and was obtained as a pink semi solid, (0.4 g, 66%). MS (ES+) 302 (M+H).

Step 6: Preparation of 2-[3-(phenylsulfonyl)-1H-indol-7-yl]ethyl 4-methylbenzenesulfonate:

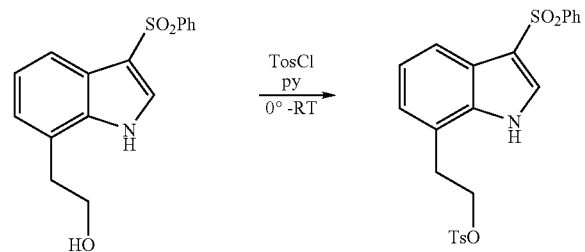

The title compound was prepared in substantially the same manner as described in Example 1, step 6 starting from 2-[3-(phenylsulfonyl)-1H-indol-7-yl]ethanol (0.988 g, 3.28 mmol), and was obtained as a white solid, (1.29 g, 86%). Mp: 142-145° C. MS (ES+) 456.2 (M+H).

Step 7: Preparation of N,N-dimethyl-N-{2-[3-(phenylsulfonyl)-1H-indol-7-yl]ethyl}amine hydrochloride:

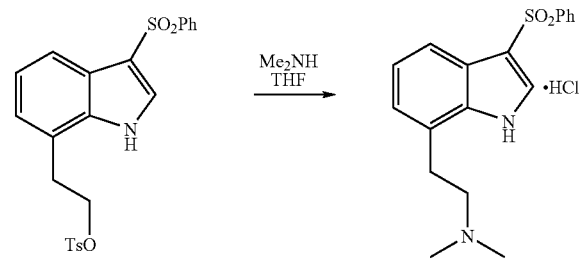

The title compound was prepared in substantially the same manner as described in Example 1, step 7 starting from 2-[3-(phenylsulfonyl)-1H-indol-7-yl]ethyl 4-methylbenzenesulfonate (0.107 g, 0.235 mmol), and was obtained as a yellow solid, (0.08 g, 99%). Mp: 205-208° C. (Dec). MS (ES−) 327.2 (M−H).

Examples 19-28

In an analogous fashion to that described in Example 18, step 7, substituting the appropriate displacing amine, the following examples are prepared.

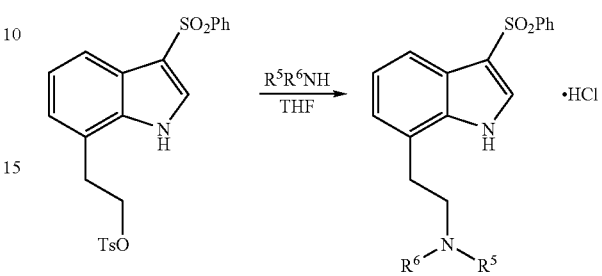

| Example | $R^5$ | $R^6$ | Mp (° C.) | MS | Appearance |
|---|---|---|---|---|---|
| 19 | H | Me | 187-188 | (M − H) 313.1 | White solid |
| 20 | H | Propyl | 260-262 | (M + H) 343 | White solid |
| 21 | H | Isopropyl | 291-293 (dec) | (M + H) 343.1 | White solid |
| 22 | H | Cyclopropyl | 213-216 (dec) | (M + H) 341.1 | White solid |
| 23 | H | Cyclopentyl | 255-256 (dec) | (M + H) 369.1 | White solid |
| 24 | Me | Et | 215-218 (dec) | (M + H) 343.1 | White solid |
| 25 | Et | Et | 165-166 (dec) | (M + H) 357.1 | White solid |
| 26 | Pyrrolidin-1-yl | | 250-252 (dec) | (M + H) 355.1 | White solid |
| 27 | Piperidin-1-yl | | 231-233 | (M + H) 369.1 | Off white solid |
| 28 | Morpholin-4-yl | | 246-248 (dec) | (M + H) 371.1 | White solid |

Example 29

{2-[3-(PHENYLSULFONYL)-1H-INDOL-7-YL]ETHYL}AMINE HYDROCHLORIDE

Step 1: Preparation of 7-(2-azido-ethyl)-3-benzenesulfonyl-1H-indole:

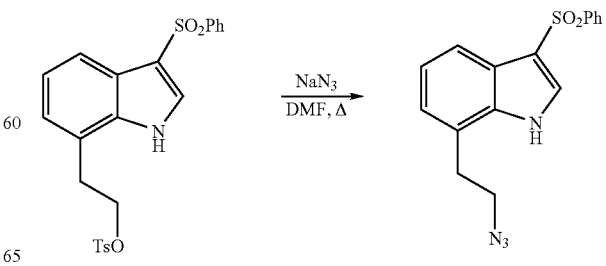

The azide was prepared in substantially the same manner as described in Example 12, step 1 starting from 2-[3-(phenyl-sulfonyl)-1H-indol-7-yl]ethyl 4-methylbenzenesulfonate (0.205 g, 0.45 mmol), and was obtained as a yellow solid, (0.135 g, 93%). MD: 160-163° C. MS (ES−) 325.1 (M−H).

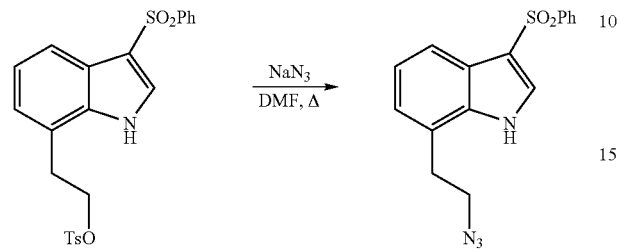

Step 2: Preparation of {2-[3-(phenylsulfonyl)-1H-indol-7-yl]ethyl}amine hydrochloride:

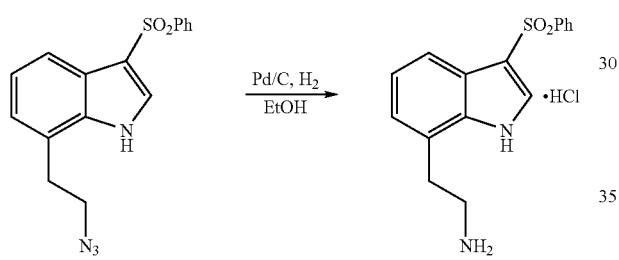

The amine was prepared in substantially the same manner as described in Example 12, step 2 starting from 7-(2-azido-ethyl)-3-(phenylsulfonyl)-1H-indole (0.110 g, 0.34 mmol), and was obtained as a white solid, (0.115 g, 99%). Mp: 185 (dec) ° C. MS (ES+) 342.1 (M+H).

Example 30

3-(PHENYLSULFONYL)-7-(2-PIPERAZIN-1-YL-ETHYL)-1H-INDOLE HYDROCHLORIDE

Step 1: Preparation of 7-[2-(4-benzylpiperazin-1-yl)ethyl]-3-(phenylsulfonyl)-1H-indole:

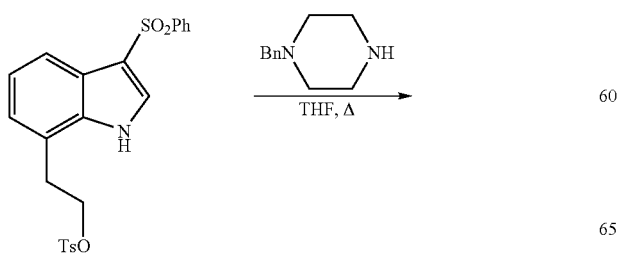

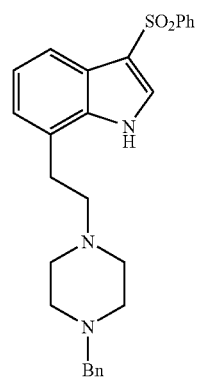

This compound was prepared in substantially the same manner as described in Example 13, step 1 starting from 2-[3-(phenylsulfonyl)-1H-indol-7-yl]ethyl 4-methylbenzenesulfonate (0.107 g, 0.235 mmol), and was obtained as a white foam, (0.130 g, 87%). Mp: 80-82° C. MS (ES+) 460.2 (M+H).

Step 2: Preparation of 3-(phenylsulfonyl)-7-(2-piperazin-1-ylethyl)-1H-indole hydrochloride:

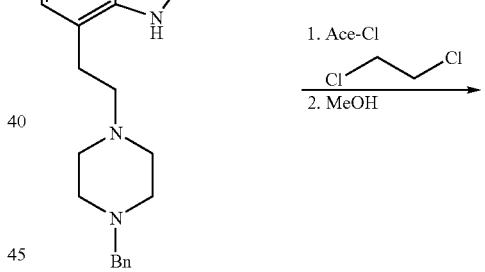

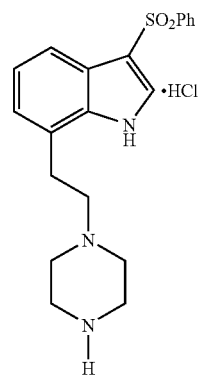

This compound was prepared in substantially the same manner as described in Example 13, step 2 starting from 7-[2-(4-benzylpiperazin-1-yl)ethyl]-3-(phenylsulfonyl)-1H-indole (0.116 g, 0.25 mmol), and was obtained as a white solid, (0.06 g, 64%). Mp: 190° C. MS (ES+) 370.1 (M+H).

Example 31

N,N-DIMETHYL-N-{2-[3-(PHENYLSULFONYL)-1H-INDOL-4-YL]ETHYL}AMINE HYDROCHLORIDE

Step 1: Preparation of 4-bromo-3-(phenylthio)-1H-indole:

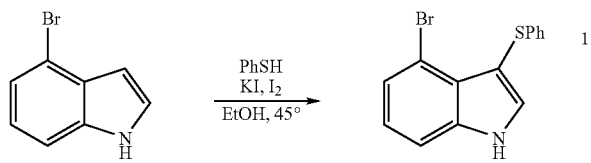

A stirred solution of 4-bromo-1H-indole (4.69 g, 23.9 mmol) in ethanol (110 mL) was added thiophenol (2.46 mL, 23.9 mmol). A solution of potassium iodide (3.97 g, 24 mmol) and iodine (6.07 g, 24 mmol) dissolved in water (5 mL) and ethanol (5 mL) is added over 5 minutes and the reaction was heated at 45° C. for 12 hours. The brown reaction is concentrated in vacuo to a dark brown oil and diluted with ethyl acetate (250 mL). The organic layer is washed with water (80 mL×2), saturated $Na_2S_2O_3$ (80 mL), and brine (80 mL), dried ($MgSO_4$), filtered and concentrated in vacuo. Purification by flash chromatography (20-30% ethyl acetate/petroleum ether) gave the title compound as a white solid (7.24 g, 99.5%). Mp: 137-139° C. MS (ES−): 302 (M−H).

Step 2: Preparation of 4-bromo-3-(phenylsulfonyl)-1H-indole:

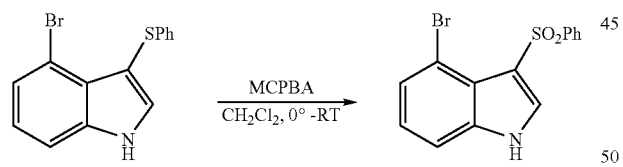

m-Chloroperbenzoic acid (26.2 g, 75% tech., 151.9 mmol) was added to a solution of 4-bromo-3-(phenylthio)-1H-indole (7.7 g, 25.3 mmol) in dry methylene chloride (250 mL) cooled to 0° C. The reaction mixture was stirred at room temperature for 4 hours then diluted with methylene chloride (150 mL) and quenched with a saturated solution of sodium bicarbonate (100 mL). After 1 hour the organic layer was separated and washed sequentially with water (75 mL), saturated sodium bicarbonate (75 mL) and brine (75 mL). The organic layer was dried ($MgSO_4$) and concentrated in vacuo to a yellow solid. Trituration with ethyl acetate and hexanes (20%) affords the title compound as a pale yellow solid (7.1 g, 83%). Mp: 202-207° C. MS (ES+): 336 (M+H).

Step 3: Preparation of 3-(phenylsulfonyl)-4-vinyl-1H-indole:

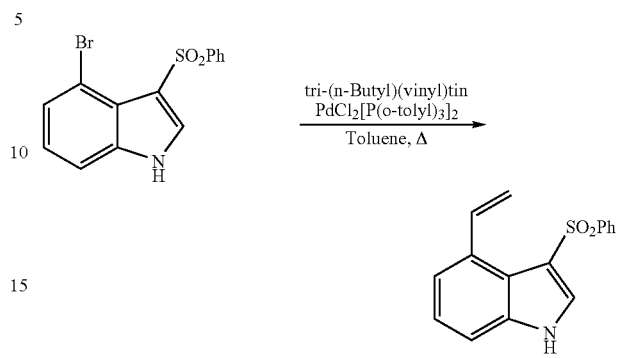

The title compound was prepared in substantially the same manner as described in Example 1, step 4 starting from 4-bromo-3-(phenylsulfonyl)-1H-indole (500 mg, 1.5 mmol), and was obtained as a white solid, (0.345 g, 82%). Mp: 125-128° C. MS (ES+) 284.1 (M+H).

Step 4: Preparation of 2-[3-(phenylsulfonyl)-1H-indol-4-yl]ethanol:

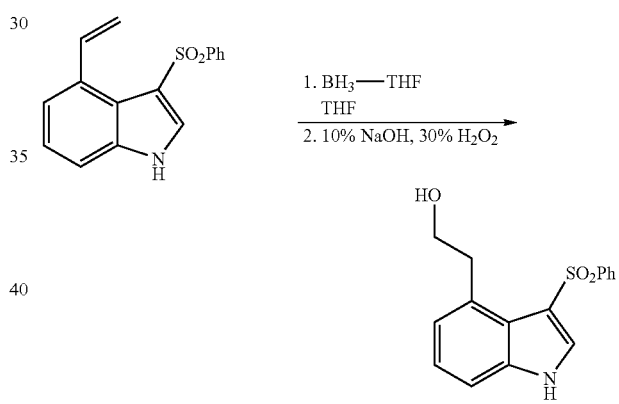

The title compound was prepared in substantially the same manner as described in Example 1, step 5 starting from 3-(phenylsulfonyl)-4-vinyl-1H-indole (338 mg, 1.2 mmol), and was obtained as a white solid, (0.27 g, 75%). Mp: 55-60° C. MS (ES+) 302.1 (M+H).

Step 5: Preparation of 2-[3-(phenylsulfonyl)-1H-indol-4-yl]ethyl 4-methylbenzenesulfonate:

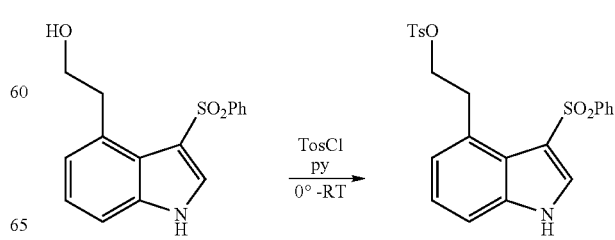

The title compound was prepared in substantially the same manner as described in Example 1, step 6 starting from 2-[3-(phenylsulfonyl)-1H-indol-4-yl]ethanol (257 mg, 0.85 mmol), and was obtained as a white foam, (0.35 g, 90%). Mp: 58-60° C. MS (ES+) 455.9 (M+H).

Step 6: Preparation of N,N-dimethyl-N-{2-[3-(phenylsulfonyl)-1H-indol-4-yl]ethyl}amine hydrochloride:

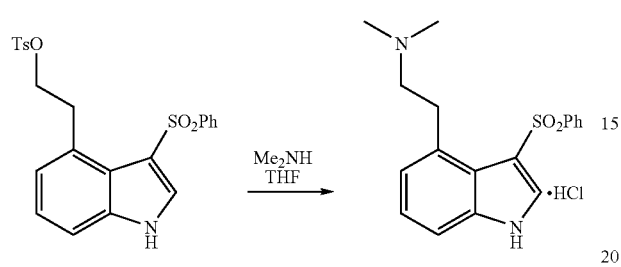

The title compound was prepared in substantially the same manner as described in Example 1, step 7 starting from 2-[3-(phenylsulfonyl)-1H-indol-4-yl]ethyl 4-methylbenzenesulfonate (116 mg, 0.25 mmol), and was obtained as a tan solid, (0.08 g, 95%). Mp: 122-126° C. MS (ES+) 329.1 (M+H).

Examples 32-60

In an analogous fashion to that described in Example 1, step 7, substituting the appropriate displacing amine, the following examples are prepared.

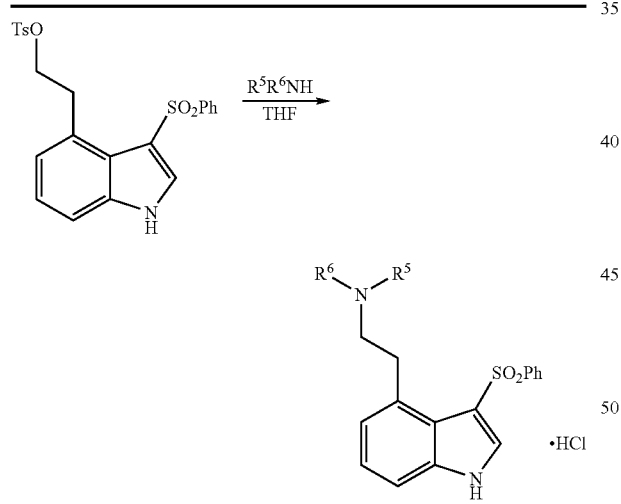

| Example | R⁵ | R⁶ | Mp (° C.) | MS | Appearance |
|---|---|---|---|---|---|
| 32 | H | Methyl | 168-170 | (M + H) 315 | Tan solid |
| 33 | H | Ethyl | 225-228 | (M + H) 329.1 | Tan solid |
| 34 | H | Propyl | 217 | (M + H) 343.1 | White solid |
| 35 | H | Isopropyl | 185-187 | (M + H) 343.1 | White solid |
| 36 | H | Cyclopropyl | 145-150 | (M + H) 341.1 | Tan solid |
| 37 | H | Cyclobutyl | 95-103 | (M + H) 355.1 | Tan solid |

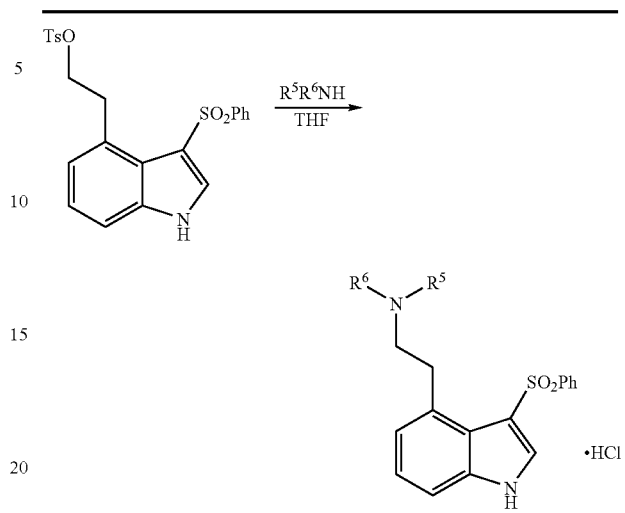

| Example | R⁵ | R⁶ | Mp (° C.) | MS | Appearance |
|---|---|---|---|---|---|
| 38 | H | Cyclopentyl | 190-191 | (M + H) 369.1 | Tan solid |
| 39 | H | Cyclohexyl | 241 | (M + H) 383.1 | White solid |
| 40 | Me | Et | 92-98 | (M + H) 343.1 | Tan solid |
| 41 | Me | Cyclohexyl | 132-140 | (M + H) 397.1 | Tan solid |
| 42 | Et | Et | 77-83 | (M + H) 357.1 | Brown solid |
| 43 | | Pyrrolidin-1-yl | 145-150 | (M + H) 355.1 | Tan solid |
| 44 | | Piperidin-1-yl | 200-205 | (M + H) 369.1 | White solid |
| 45 | | Morpholin-4-yl | 164-165 | (M + H) 371.1 | White solid |
| 46 | H | 1,2,2,-trimethylpropyl | 275 | (M + H) 385.2 | White solid |
| 47 | H | Benzyl | 172 | (M + H) 391.148 | White solid |
| 48 | H | Isobutyl | 220 | (M + H) 357.1 | White solid |
| 49 | H | 2,2-dimethylpropyl | 135 | (M + H) 371.1 | White solid |
| 50 | H | Dimethylamino propyl | NA | (M + H) 386.2 | White solid |
| 51 | H | (tetrahydrofur-2-yl)methyl | 110-115 | (M + H) 385.1 | Brown solid |
| 52 | | 2,6-Dimethyl-piperidin-1-yl | NA | (M − H) 395 | Off white solid |
| 53 | Me | Isopropyl | NA | (M + H) 357 | White solid |
| 54 | Et | Isopropyl | NA | (M + H) 371 | White solid |
| 55 | | 2-Methyl-pyrrolidin-1-yl | NA | (M + H) 369 | White solid |
| 56 | | 2-Methyl-piperidin-1-yl | NA | (M + H) 383 | White solid |
| 57 | | 3-Methyl-piperidin-1-yl | NA | (M + H) 383 | White needles |
| 58 | | Azepan-1-yl | NA | (M + H) 383 | Light tan needles |
| 59 | | 4-Methyl-piperazin-1-yl | NA | (M − H) 382 | Yellow solid |
| 60 | | Piperazin-1-yl | NA | (M + H) 370.5 | White solid |

Example 61

{2-[3-(PHENYLSULFONYL)-1H-INDOL-4-YL]ETHYL}AMINE HYDROCHLORIDE

Step 1: Preparation of 4-(2-azido-ethyl)-3-benzenesulfonyl-1H-indole:

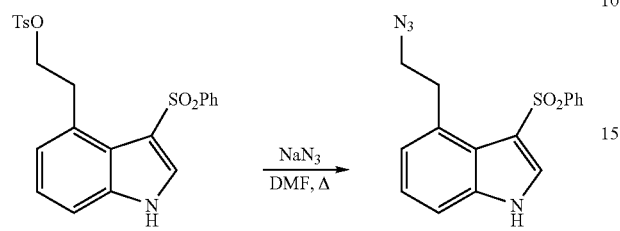

The azide was prepared in substantially the same manner as described in Example 12, step 1 starting from methyl 2-[3-(phenylsulfonyl)-1H-indol-4-yl]ethyl 4-methylbenzenesulfonate (171 mg, 0.37 mmol), and was obtained as a clear waxy solid, (120 mg, 93%). Mp: 143° C. MS (ES+) 327.1 (M+H).

Step 2: Preparation of 2-[3-(phenylsulfonyl)-1H-indol-4-yl]ethyl}amine hydrochloride:

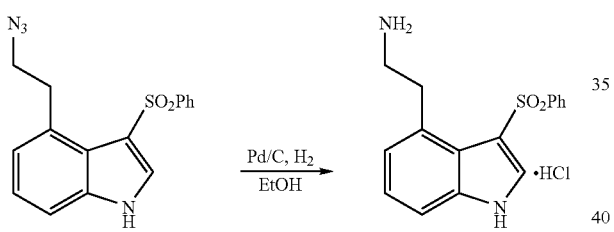

This compound was prepared in substantially the same manner as described in Example 12, step 2 starting from methyl 4-(2-azidoethyl)-3-(phenylsulfonyl)-1H-indole (100 mg, 0.30 mmol), and was obtained as a light brown foam, (90 mg, 99%). Mp: 130-134° C. MS (ES+) 301 (M+H).

Example 62

N,N-DIMETHYL-N-{2-[3-(3-FLUOROPHENYLSULFONYL)-1H-INDOL-4-YL]ETHYL}AMINE HYDROCHLORIDE

This compound was prepared in substantially the same manner as described in Example 31, step 1-6 starting from 4-bromo-1H-indole and 3-fluorothiophenol. Retention time=3.908 min. MS (ES+) 347.3 (M+H).

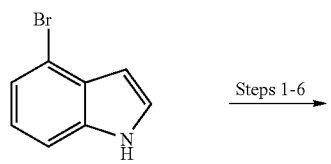

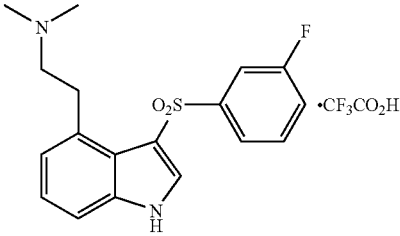

Examples 63-84

In an analogous fashion to that described in Example 1, step 7, substituting the appropriate displacing amine, the following examples are prepared.

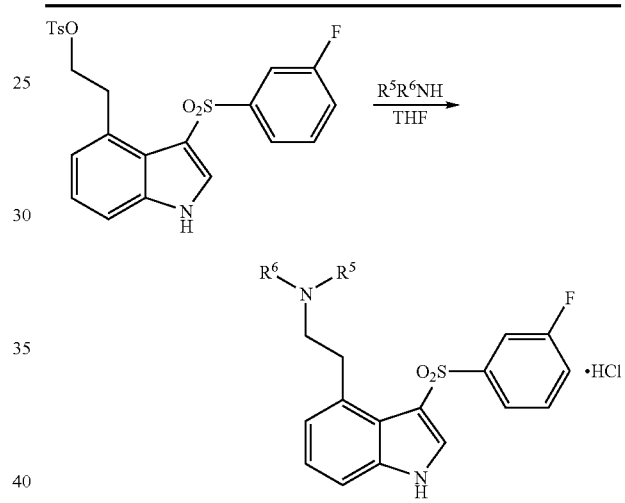

| Example | $R^5$ | $R^6$ | Retention time (min) | MS |
|---|---|---|---|---|
| 63 | H | Methyl | 3.791 | (M + H) 333.3 |
| 64 | H | Ethyl | 3.978 | (M + H) 347.3 |
| 65 | H | Propyl | 4.354 | (M + H) 361.3 |
| 66 | H | Isopropyl | 4.305 | (M + H) 361.3 |
| 67 | H | Cyclopropyl | 4.242 | (M + H) 359.3 |
| 68 | H | Cyclobutyl | 4.451 | (M + H) 373.3 |
| 69 | H | Cyclopentyl | 4.766 | (M + H) 387.4 |
| 70 | H | Cyclohexyl | 4.88 | (M + H) 401.3 |
| 71 | Me | Et | 4.262 | (M + H) 361.3 |
| 72 | Me | Cyclohexyl | 5.181 | (M + H) 415.35 |
| 73 | Et | Et | 4.27 | (M + H) 375.3 |
| 74 | | Pyrrolidin-1-yl | 4.162 | (M + H) 373.3 |
| 75 | | Piperidin-1-yl | 4.555 | (M + H) 387.4 |
| 76 | | Morpholin-4-yl | 4.048 | (M + H) 389.3 |
| 77 | H | Isobutyl | 4.555 | (M + H) 375.3 |
| 78 | H | Pentan-3-yl | 4.984 | (M + H) 389.35 |
| 79 | H | 2-Methyl-1-butyl | 5.01 | (M + H) 389.3 |
| 80 | H | 1,2,2,-Trimethylpropyl | 4.92 | (M + H) 403.4 |
| 81 | H | 2,2-Dimethylpropyl | 4.949 | (M + H) 389.3 |
| 82 | H | (tetrahydrofur-2-yl)methyl | 4.211 | (M + H) 403.3 |
| 83 | H | 3-(Dimethylamino)propyl | 1.242 | (M + H) 404.4 |
| 84 | Me | 2-hydroxyethyl | 4.013 | (M + H) 377.3 |

Example 85

{2-[3-(3-FLUOROPHENYLSULFONYL)-1H-IN-DOL-4-YL]ETHYL}AMINE HYDROCHLORIDE

Step 1: Preparation of 4-(2-Azido-ethyl)-3-(3-fluoro-benzenesulfonyl)-1H-indole:

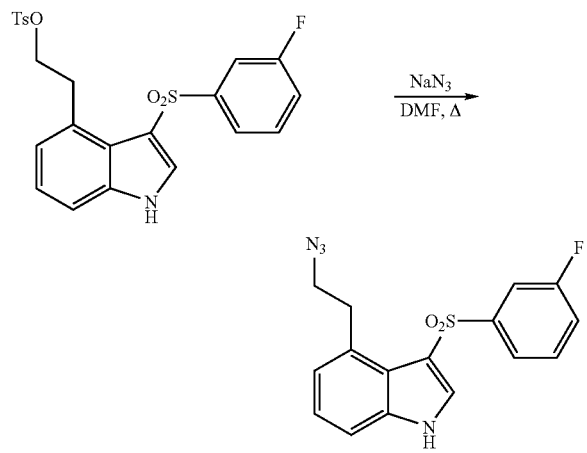

The azide was prepared in substantially the same manner as described in Example 12, step 1 starting from methyl 2-[3-(3-fluorophenylsulfonyl)-1H-indol-4-yl]ethyl 4-methylbenzenesulfonate (213 mg, 0.45 mmol), and was obtained as a off white solid, (152 mg, 99%). Mp: 136-138° C. MS (ES−) 343.0 (M−H).

Step 2: Preparation of {2-[3-(3-fluorophenylsulfonyl)-1H-indol-4-yl]ethyl}amine hydrochloride:

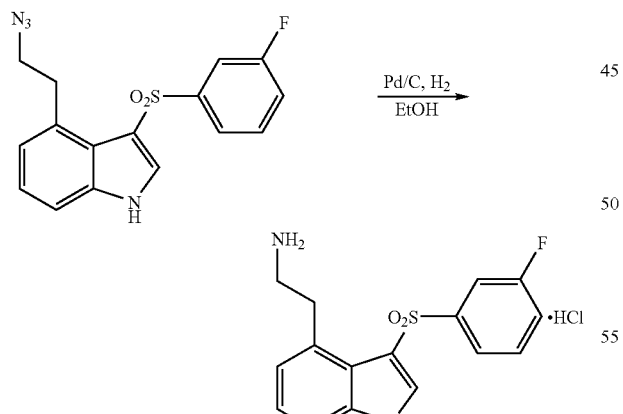

This compound was prepared in substantially the same manner as described in Example 12, step 2 starting from methyl 4-(2-azidoethyl)-3-(3-fluorophenylsulfonyl)-1H-indole (140 mg, 0.40 mmol), and was obtained as a light tan foam, (140 mg, 99%). Mp: 122-125° C. MS (ES+) 319.1 (M+H).

Example 86

N,N-DIMETHYL-N-{2-[3-(PHENYLSULFONYL)-1H-INDOL-6-YL]ETHYL}AMINE HYDROCHLORIDE

Step 1: Preparation of 6-bromo-3-(phenylthio)-1H-indole:

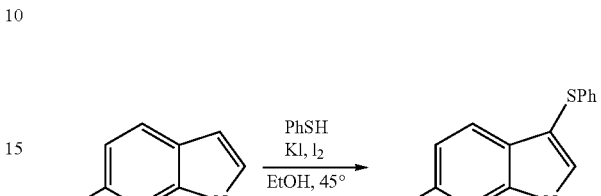

The sulfide compound was prepared in substantially the same manner as described in Example 31, step 1 starting from 6-bromo-1H-indole (3.8 g, 19.4 mmol), and was obtained as an off white solid, (5.90 g, 99%). Mp: 145-148° C. MS (ES−) 302.1 (M−H).

Step 2: Preparation of 6-bromo-3-(phenylsulfonyl)-1H-indole:

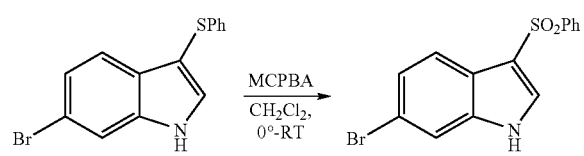

The sulfonyl compound was prepared in substantially the same manner as described in Example 31, step 2 starting from 4-bromo-3-(phenylthio)-1H-indole (5.9 g, 19.4 mmol), and was obtained as an white solid, (5.22 g, 80%). Mp: 230.5° C. MS (ES−) 334.1 (M−H).

Step 3: Preparation of 3-(phenylsulfonyl)-6-vinyl-1H-indole:

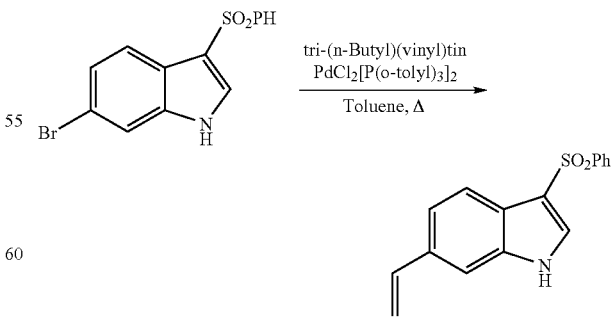

The vinyl compound was prepared in substantially the same manner as described in Example 1, step 4 starting from 4-bromo-3-(phenylsulfonyl)-1H-indole (500 mg, 1.5 mmol), and was obtained as a white solid, (0.345 g, 82%). Mp: 125-128° C. MS (ES+) 284.1 (M+H).

Step 4: Preparation of 2-[3-(phenylsulfonyl)-1H-indol-6-yl]ethanol:

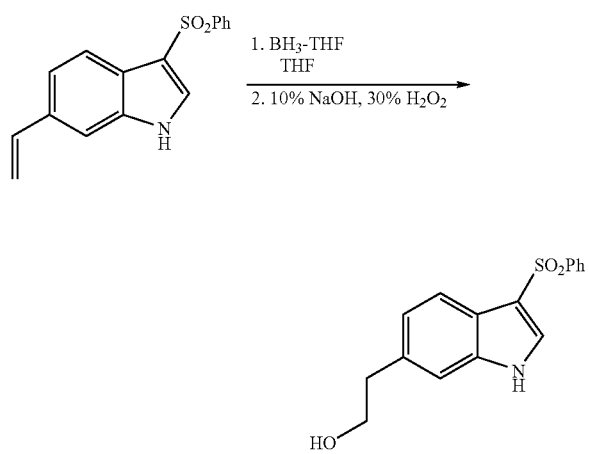

The hydroxyl compound was prepared in substantially the same manner as described in Example 1, step 5 starting from 3-(phenylsulfonyl)-6-vinyl-1H-indole (3.28 g, 8.11 mmol), and was obtained as a white solid, (1.49 g, 62%). Mp: 74-75° C. MS (ES+) 302.1 (M+H).

Step 5: Preparation of 2-[3-(phenylsulfonyl)-1H-indol-6-yl]ethyl 4-methylbenzenesulfonate:

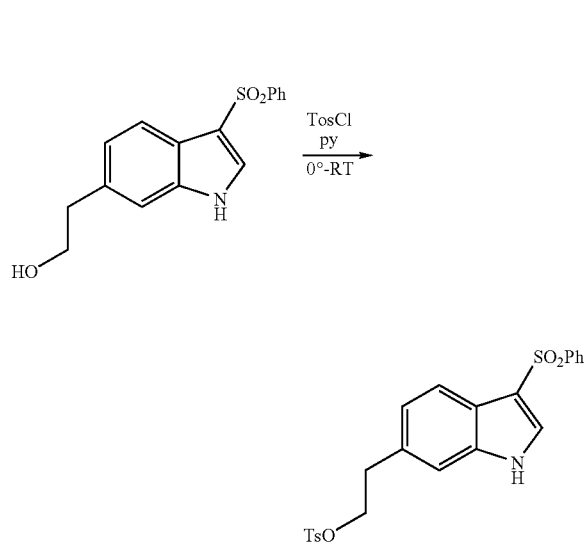

The tosylate compound was prepared in substantially the same manner as described in Example 1, step 6 starting from 2-[3-(phenylsulfonyl)-1H-indol-6-yl]ethanol (1.41 g, 4.68 mmol), and was obtained as a white solid, (2.04 g, 96%). Mp: 129-132° C. MS (ES−) 454.1 (M−H).

Step 6: Preparation of N,N-dimethyl-N-{2-[3-(phenylsulfonyl)-1H-indol-6-yl]ethyl}amine hydrochloride:

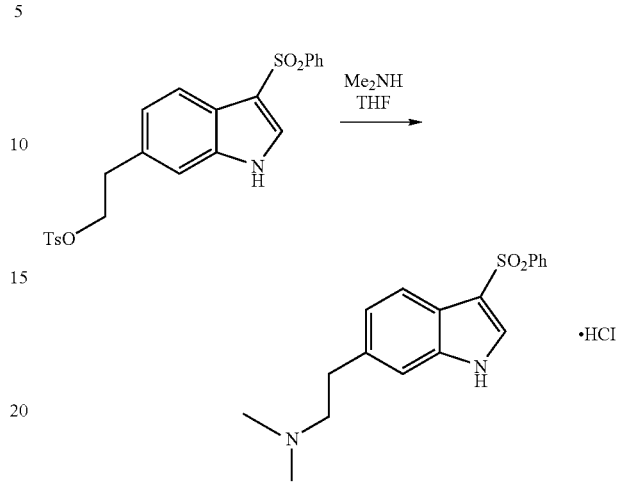

The title compound was prepared in substantially the same manner as described in Example 1, step 7 starting from 2-[3-(phenylsulfonyl)-1H-indol-6-yl]ethyl 4-methylbenzenesulfonate (46 mg, 0.1 mmol), and was obtained as a yellow solid, (0.26 mg, 80%). Mp: 118-120° C. MS (ES+) 329.1 (M+H).

Examples 87-108

In an analogous fashion to that described in Example 1, step 7, substituting the appropriate displacing amine and using trifluoroacetic acid instead of hydrochloric acid, the following examples are prepared.

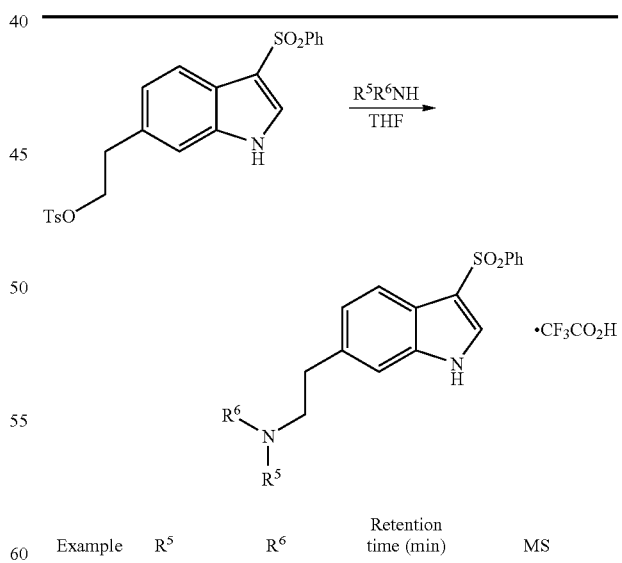

| Example | $R^5$ | $R^6$ | Retention time (min) | MS |
|---|---|---|---|---|
| 87 | H | Methyl | 4.14 | (M + H) 315.1 |
| 88 | H | Ethyl | 4.224 | (M + H) 329.3 |
| 89 | H | Propyl | 4.30 | (M + H) 343.3 |
| 90 | H | Isopropyl | 4.41 | (M + H) 343.3 |
| 91 | H | Cyclopropyl | 4.344 | (M + H) 341.3 |
| 92 | H | Cyclobutyl | 4.476 | (M + H) 355.3 |
| 93 | H | Cyclopentyl | 4.574 | (M + H) 369.3 |

-continued

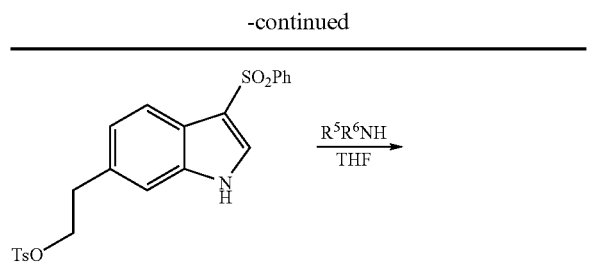

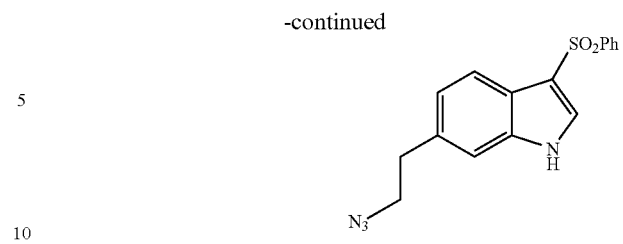

| Example | R[5] | R[6] | Retention time (min) | MS |
|---|---|---|---|---|
| 94 | H | Cyclohexyl | 5.106 | (M + H) 383.4 |
| 95 | Me | Et | 4.264 | (M + H) 343.3 |
| 96 | Me | Cyclohexyl | 4.882 | (M + H) 397.4 |
| 97 | Et | Et | 4.316 | (M + H) 357.4 |
| 98 | | Pyrrolidin-1-yl | 4.255 | (M + H) 355.3 |
| 99 | | Piperidin-1-yl | 4.283 | (M + H) 369.3 |
| 100 | | Morpholin-4-yl | 4.126 | (M + H) 371.3 |
| 101 | | Piperazin-1-yl | 4.119 | (M + H) 370.4 |
| 102 | H | Isobutyl | 4.516 | (M + H) 357.3 |
| 103 | H | 3-Pentyl | 4.685 | (M + H) 371.4 |
| 104 | H | 2-methyl-1-butyl | 4.774 | (M + H) 371.4 |
| 105 | H | 1,2,2,-trimethylpropyl | 4.871 | (M + H) 385.4 |
| 106 | H | 2,2-dimethylpropyl | 4.526 | (M + H) 371.4 |
| 107 | H | (tetrahydrofur-2-yl)methyl | 4.455 | (M + H) 385.3 |
| 108 | | Azetidin-1-yl | 4.199 | (M + H) 341.3 |

Example 109

{2-[3-(PHENYLSULFONYL)-1H-INDOL-6-YL]ETHYL}AMINE HYDROCHLORIDE

Step 1: Preparation of 6-(2-azido-ethyl)-3-benzenesulfonyl-1H-indole:

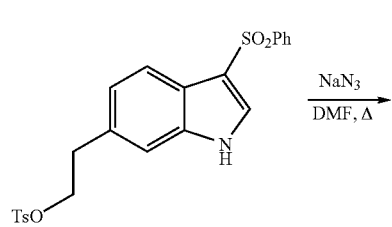

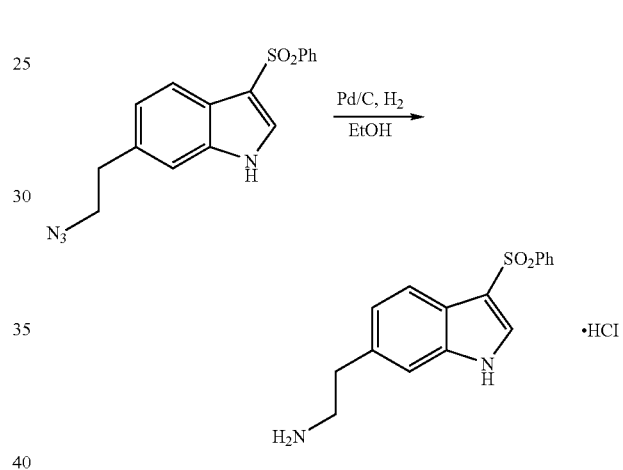

The azide compound was prepared in substantially the same manner as described in Example 12, step 1 starting from methyl 2-[3-(phenylsulfonyl)-1H-indol-6-yl]ethyl 4-methyl-benzenesulfonate (205 mg, 0.43 mmol), and was obtained as a clear white foam (140 mg, 99%). Mp: 130-134° C. MS (ES+) 327.1 (M+H).

Step 2: Preparation of {2-[3-(phenylsulfonyl)-1H-indol-6-yl]ethyl}amine hydrochloride:

The title compound was prepared in substantially the same manner as described in Example 12, step 2 starting from methyl 6-(2-azidoethyl)-3-(phenylsulfonyl)-1H-indole (120 mg, 0.37 mmol), and was obtained as a light brown solid, (100 mg, 90%). Mp: 178° C. MS (ES+) 301.1 (M+H).

Example 110

N-ISOPROPYL-3-[3-(PHENYLSULFONYL)-1H-INDOL-4-YL]PROPAN-1-AMINE HYDROCHLORIDE

Step 1: Preparation of 3-(1H-indol-4-yl)propan-1-ol:

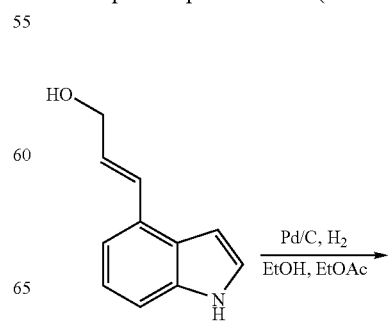

-continued

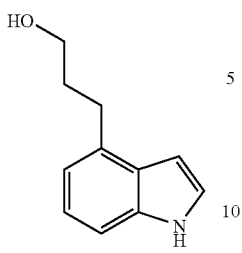

To a suspension of 10% palladium on carbon (200 mg) in absolute ethanol (30 mL) was added a solution of (2E)-3-(1H-indol-4-yl)prop-2-en-1-ol (0.98 g, 5.66 mmol) in ethyl acetate (30 mL) and the mixture hydrogenated at 50 psi for 15 min. The reaction mixture was filtered through celite and concentrated in vacuo to give a light purple syrup. (2E)-3-(1H-indol-4-yl)prop-2-en-1-ol was prepared by the method of Kardos, N.; Genet J-P. Tetrahedron Asymmetry 1994, 5, 1525-1533, which is incorporated herein by reference in its entirety. Purification by flash chromatography (20% to 50% ethyl acetate/hexane) gave the title compound as a colorless syrup (0.92 g, 93%). MS (ES+) m/z 176.2 (M+H).

Step 2: Preparation of 3-[3-(3-phenylthio)-1H-indol-4-yl]propan-1-ol:

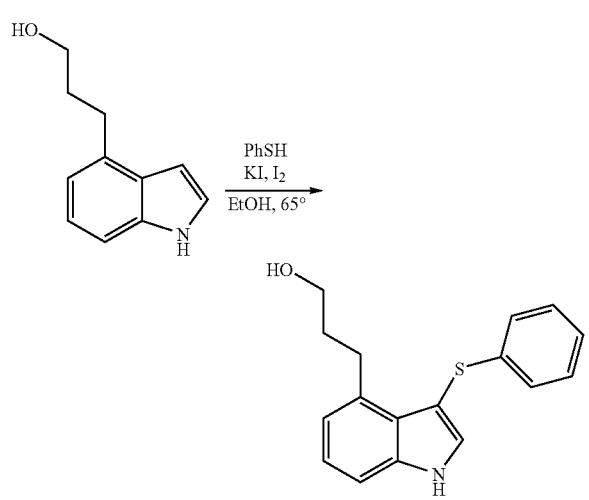

To a solution of 3-(1H-indol-4-yl)propan-1-ol (0.91 g, 5.19 mmol) and thiophenol (0.53 mL, 5.19 mmol) in absolute ethanol (30 mL) was added a solution of potassium iodide (0.862 g, 5.19 mmol) and iodine (1.318 g, 5.19 mmol) in ethanol (7.5 mL) and water (22.5 mL) over 5 minutes, and the reaction was then heated at 65° C. for 5.5 hours. The cooled reaction mixture was diluted with ethyl acetate (250 mL), washed with 5% aqueous Na₂S₂O₃ solution (250 mL), water (250 mL) and brine (250 mL), dried (Na₂SO₄), filtered and concentrated in vacuo to afford an off-white solid. Purification by flash chromatography (25 to 75% ethyl acetate/hexane) afforded a white solid. The product was recrystallized from 3:1 v/v hexane:ethyl acetate (60 mL) to afford the title compound as a white crystalline solid (1.048 g, 71%). MS (ES+) m/z 284.1 (M+H).

Step 3: Preparation of 3-[3-(phenylsulfonyl)-1H-indol-4-yl]propan-1-ol:

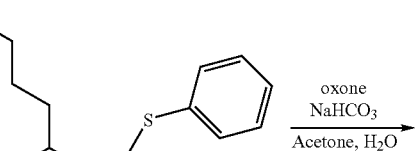

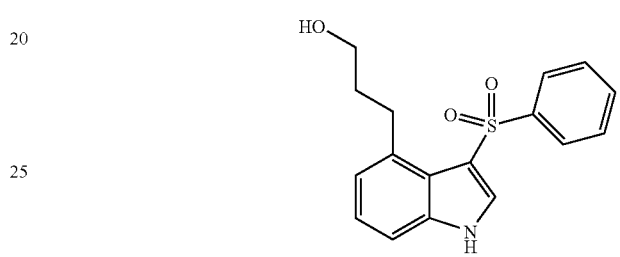

To a solution of 3-[3-(phenylthio)-1H-indol-4-yl]propan-1-ol (1.024 g, 3.61 mmol) in acetone (45 mL) was added a solution of sodium hydrogen carbonate (0.759 g, 9.03 mmol) in water (45 mL) followed by OXONE® (supplied by DuPont, potassium peroxymonosulfate as active ingredient) (5.55 g, 9.03 mol) and the reaction mixture stirred at room temperature for 26 hours. The acetone was removed in vacuo and the resulting suspension partitioned between ethyl acetate (120 mL) and water (100 mL). The organic phase was separated, washed with water (100 mL) and brine (100 mL), dried (Na₂SO₄), filtered and concentrated in vacuo to afford a white foam. Ethyl acetate (30 mL) was added to the crude product and the mixture stirred vigorously for 2 hours then filtered to afford the title compound as a white solid (1.027 g, 90%). MS (ES−) m/z 314.0 (M−H).

Step 4: Preparation of 3-phenylsulfonyl-4-(3-chloropropyl)-1H-indole and 3-[3-(phenylsulfonyl)-1H-indol-4-yl]propyl 4-methylbenzenesulfonate:

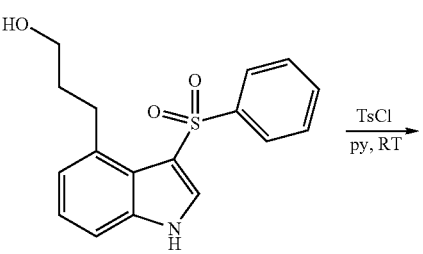

-continued

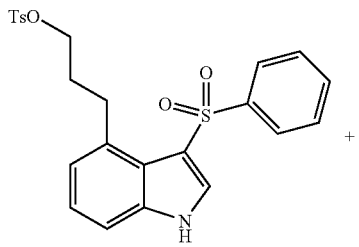

+

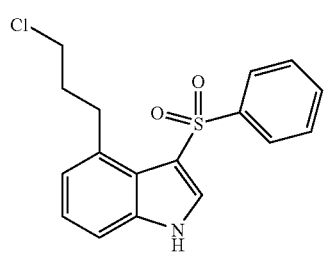

To a solution of 3-[3-(phenylsulfonyl)-1H-indol-4-yl]propan-1-ol (1.006 g, 3.19 mmol) in anhydrous acetonitrile (25 mL) at room temperature under nitrogen was added pyridine (0.65 mL, 7.97 mmol) followed by p-toluenesulfonyl chloride, and the reaction mixture stirred for 11 days. The reaction mixture was then concentrated to a small volume in vacuo, and the mixture partitioned between ethyl acetate (100 mL) and 1 N aqueous HCl (100 mL). The organic phase was separated, washed with water (2×100 mL) and brine (200 mL), dried (Na$_2$SO$_4$), filtered and concentrated in vacuo to afford a yellow syrup. Purification by flash chromatography (0 to 40% ethyl acetate/hexane) afforded 3-phenylsulfonyl-4-(3-chloro-propyl)-1H-indole as a colorless foam (0.51 g, 48%). MS (ES+) m/z 334 (M+H). Further elution afforded 3-[3-(phenylsulfonyl)-1H-indol-4-yl]propyl 4-methylbenzenesulfonate as a white foam (0.48 g, 32%). MS (ES+) m/z 469.7 (M+H).

Step 5: Preparation of N-isopropyl-3-[3-(phenylsulfonyl)-1H-indol-4-yl]propan-1-amine hydrochloride:

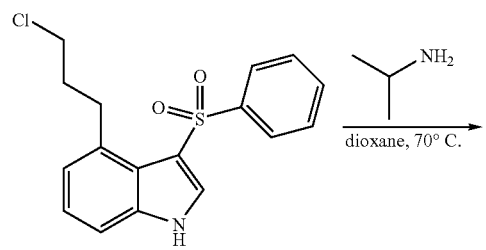

-continued

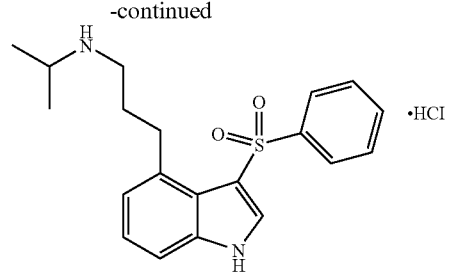

To a solution of 3-phenylsulfonyl-4-(3-chloro-propyl)-1H-indole (0.255 g, 0.76 mmol) in anhydrous dioxane (5 mL) was added isopropylamine (0.65 mL, 7.64 mmol) and the reaction mixture heated to 70° C. in a sealed vessel for 7 days. The cooled reaction mixture was then diluted with 1 N aqueous NaOH (50 mL) and the resulting milky suspension extracted with ethyl acetate (50 mL). The organic phase was separated, washed with water (50 mL) and brine (50 mL), dried (Na$_2$SO$_4$), filtered and concentrated in vacuo to afford a yellow foam. Purification by flash chromatography (0 to 10% ammonia saturated methanol/dichloromethane) afforded N-isopropyl-3-[3-(phenylsulfonyl)-1H-indol-4-yl]propan-1-amine as a yellow foam (0.23 g, 86%). The product was dissolved in absolute ethanol (10 mL), 1.25 N HCl in ethanol (0.78 mL, 0.98 mmol, 1.5 equivalents) added, the mixture stirred for 15 min and then concentrated in vacuo to afford a yellow foam. The product was crystallized from 1:1 v/v ethanol:tert-butyl methyl ether (10 mL) to give the title compound as white crystals (0.172 g, 57%). MS (ES+) m/z 357.3 (M+H).

Example 111

3-(PHENYLSULFONYL)-4-(3-PIPERIDIN-1-YL-PROPYL)-1H-INDOLE

The title compound was prepared in an analogous fashion to that described in Example 110, step 5, substituting piperidine for isopropylamine, and was obtained as a white solid. MS 383.3 (M+H).

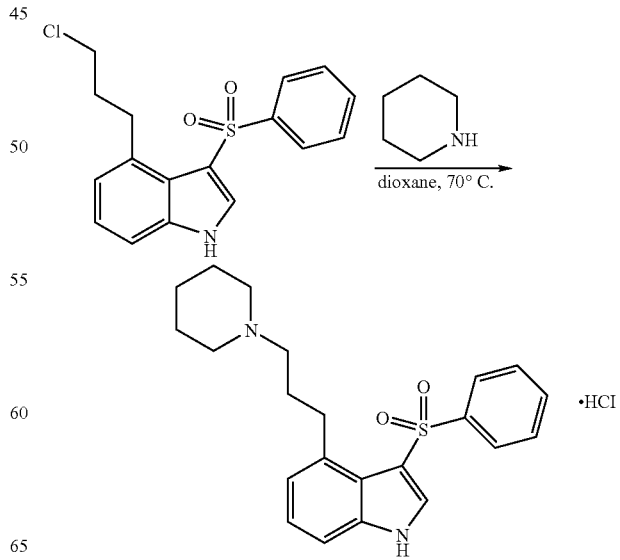

Example 112

N-ETHYL-N-METHYL-3-[3-(PHENYLSULFO-NYL)-1H-INDOL-4-YL]PROPAN-1-AMINE HYDROCHLORIDE

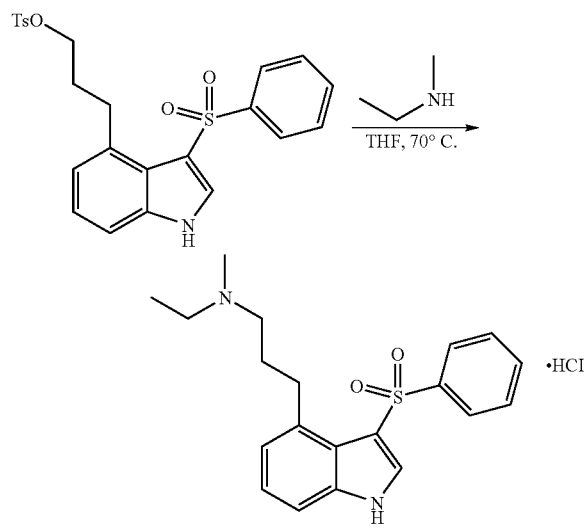

To a solution of 3-[3-(phenylsulfonyl)-1H-indol-4-yl]propyl 4-methylbenzenesulfonate (0.21 g, 0.447 mmol) in anhydrous THF (5 mL) was added N-ethylmethylamine (0.77 mL, 8.944 mmol) and the reaction mixture heated to 65° C. in a sealed vessel for 16 hours. The cooled reaction mixture was then diluted with 1 N aqueous NaOH (50 mL) and the resulting milky suspension extracted with ethyl acetate (50 mL). The organic phase was separated, washed with water (50 mL) and brine (50 mL), dried ($Na_2SO_4$), filtered and concentrated in vacuo to afford N-ethyl-N-methyl-3-[3-(phenylsulfonyl)-1H-indol-4-yl]propan-1-amine as a cream solid (0.16 g, 100%). The product was dissolved in absolute ethanol (10 mL), 1.25 N HCl in ethanol (0.47 mL, 0.583 mmol, 1.3 equivalents) added, the mixture stirred for 15 min and then concentrated in vacuo to afford a yellow syrup. The product was crystallized from ethanol (5 mL) to give the title compound as white needles (0.121 g, 69%). MS (ES+) m/z 356.9 (M+H).

Comparative Evaluation of 5-$HT_6$ Binding Affinity of Test Compounds

The affinity of test compounds for the 5-$HT_6$ receptor is evaluated in the following manner. Cultured Hela cells expressing human cloned 5-$HT_6$ receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 microliter volumes. Bovine Serum Albumin is used as the standard in the protein determination according to the method described in Lowry et al., *J. Biol. Chem.* 1951, 193, 265. The volume of the suspended cell membranes is adjusted to give a tissue protein concentration of 1.0 mg/mL of suspension. The prepared membrane suspension (10 times concentrated) is aliquoted in 1.0 mL volumes and stored at −70° C. until used in subsequent binding experiments.

Binding experiments are performed in a 96 well microtiter plate format in a total volume of 200 microliters. To each well is added the following mixture: 80.0 microliter of incubation buffer made in 50 mM Tris.HCl buffer (pH 7.4) containing 10.0 mM $MgCl_2$ and 0.5 mM EDTA and 20 microliters of [$^3$H]-LSD (S.A., 86.0 Ci/mmol, available from Amersham Life Science), 3.0 nM. The dissociation constant, $K_D$ of the [$^3$H]-LSD at the human 5-$HT_6$ receptor is 2.9 nM, as determined by saturation binding with increasing concentrations of [$^3$H]-LSD. The reaction is initiated by the final addition of 100.0 microliters of tissue suspension. Nonspecific binding is measured in the presence of 10.0 micromoles methiothepin. The test compounds are added in 20.0 microliter volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 microliter Microscint®-20 scintillant to each shallow well. The unifilter plate is heat-sealed and counted in a Packard TopCount® with a tritium efficiency of 31%.

Specific binding to the 5-$HT_6$ receptor is defined as the total radioactivity bound less the amount bound in the presence of 10.0 microliter unlabelled methiothepin. Binding in the presence of varying concentrations of test compound is expressed as a percentage of specific binding in the absence of test compound. The results are plotted as log % bound versus log concentration of the test compound. Nonlinear regression analysis of data points with a computer assisted program Prism® yielded both the $IC_{50}$ and the $K_i$ values of the test compounds with 95% confidence limits. A linear regression is plotted, from which the $IC_{50}$ value is determined and the $K_i$ value is determined based upon the following equation: $K_i=IC_{50}/(1+L/K_D)$ where L is the concentration of the radioactive ligand used and $K_D$ is the dissociation constant of the ligand for the receptor, both expressed in nM.

Using this assay, the $K_i$ values were determined and the compared to those values obtained by representative compounds known to demonstrate binding to the 5-$HT_6$ receptor. The data shown in Table 1 (vide infra) demonstrate that the compounds of the present invention have a high degree of affinity for the 5-$HT_6$ receptor.

Comparative Evaluation of Functional Norepinephrine (NE) Uptake Inhibition of Test Compounds

Cell Lines, Culture Reagents and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 µg/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% $CO_2$). On day 2, growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. Plates containing cells with 200 µl of assay buffer were equilibrated for 10 minutes at 37° C. prior to addition of compounds. A stock solution of desipramine was prepared in DMSO (10 mM) and delivered to triplicate wells containing cells for a final test concentration of 1 µM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 µl of assay buffer. The cells in assay buffer with test compounds were incubated for 20 minutes at 37° C. To initiate the NE uptake, [$^3$H]NE diluted in assay buffer (120 nM final assay concentration) was delivered in 25 µl aliquots to each well and the plates were incubated for 5 minutes (37° C.). The reaction was terminated by decanting the supernatant from the plate. The plates containing cells were washed twice with 200 µl assay buffer (37° C.) to remove free radioligand. The plates were then inverted, left to dry for 2 minutes, then reinverted and air-dried for an additional 10 minutes. The cells were lysed in 25 µl of 0.25 N NaOH solution (4° C.), placed on a shake table and vigorously shaken for 5 minutes. After cell lysis, 75 µl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $IC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake (1 µM desipramine). Estimation of the $IC_{50}$ value was completed on a log scale and the line was fit between the maximum and minimum binding or uptake values. All graphic data representation was generated by normalizing each data point to a mean percent based on the maximum and minimum binding or uptake values. The $IC_{50}$ values reported from multiple experiments were calculated by pooling the raw data from each experiment and analyzing the pooled data as one experiment.

Comparative Evaluation of Functional 5-$HT_{2A}$ Antagonism of Test Compounds

5-$HT_{2A}$ FLIPR Assay

Cell Cultures, Culture Reagents, and Assays

CHO cells transfected with cDNA expressing the human 5-$HT_{2A}$ receptor are cultured in Dulbecco's modified Eagle's medium (Gibco #11995-065) supplemented with 10% fetal bovine serum, non-essential amino acids and selection markers. Cells are washed with PBS without $Ca^{2+}$ and 3 mL Trypsin is added to dissociate cells. After 3 minute incubation, 7 mL Trypsin Neutralizing Solution is added. Cells are then aspirated from flask and mixed in a 50 mL conical tube. 10 µL sample is used to count cells on a hemacytometer. Cells are then plated at 40,000 cells per well into sterile black 96 well plates with clear bottoms (VWR #29443-152) for 24 hours.

Drug Plate Preparation

Two 96-well drug plates are prepared for each cell plate. Plate 1 will contain compounds to be tested and plate 2 will contain the agonist DOI (3 nM) to activate a calcium response. Specific details of compound preparation are listed below. All compounds are made in 1×HBSS (Gibco #14175-095) supplemented with 20 mM HEPES (Gibco #15630-080). Outside wells are not used due to an edge effect seen in these cells. The reference compounds DOI and 5-HT are used as standard 5HT agonists. MDL and Mianserin are used as standard $5HT_{2A}$ selective receptor antagonists.

Preparation of Plate 1: Test Compound Plate

For screening test compounds at 1 µM, a 1 mM stock is diluted to 19 µM (FLIPR will make final dilution) and added to 4 wells in the test plate at 50 µL per well. Standards for plate one are Vehicle, 1 µM DOI, and 3 nM MDL.

For $IC_{50}$ value determination, concentrations are generated by serial dilution of a 1 mM stock solution. On the day of the assay, test compound solutions of appropriate concentrations are diluted in assay buffer as described for single concentration testing. This procedure is followed to ensure that the solvent concentration is consistent across dilutions. The typical concentration testing range of compounds is $10^{-10}$-$10^{-5}$ M in half log or full log increments.

Preparation of Plate 2: Agonist (DOI) Plate

A 10 µM DOI stock is diluted to 60 nM and added to the respective wells. The pipeting station of the FLIPR will make an additional 20-fold dilution for a final concentration of 3 nM. Standards for this plate include Vehicle and 3 nM DOI.

Calcium Dye Preparation

Contents of dye vial (Molecular Devices #R8090) are dissolved in 100 mL of 1×HBSS supplemented with 20 mM HEPES. Aliquots can be frozen at −20° C. for up to one week for future use. On the day of assay, dye is thawed and diluted to half concentration. Probenecid (Sigma #P-8761), a calcium anion exchange inhibitor, is made fresh from powder on the day of the experiment and added to the Calcium Buffer at a 2.5 mM final concentration prior to addition to the cells.

FLIPR Machine Loading

Cells are allowed to adhere for 24 hours in 96-well plates. At time of assay, the cultured media is removed from the cells and replaced with 180 μL per well of Calcium 3 Assay Buffer and incubated for 1 hour at 37° C. with 5% $CO_2$.

Cell, compound and DOI plates are loaded into the FLIPR machine. The baseline fluorescence level is read once every second for 1 minute. Compound (10 μL) is transferred from the compound plate to the cells and the fluorescence level recorded every 6 seconds for 2 minutes to determine any agonist activity. Baseline fluorescence is recorded again every second for 10 seconds. For antagonist determination, 10 μL of 3 nM DOI is transferred from the DOI plate to the cells and the fluorescence level recorded every 6 seconds for 5 minutes. The pipetting unit of the FLIPR machine completes all transfers.

Analysis of Results

Single Concentration

Agonist stimulation is expressed as a percentage of the response observed with 1 uM DOI.

Antagonist inhibition of 3 nM DOI stimulation is expressed as a percentage of the response observed with 3 nM DOI alone.

Concentration Curve

A 4-parameter logistic function is used to generate the $IC_{50}$ values. The data are log transformed prior to analysis.

TABLE 1

| Example No. | Ki (nM) @ 5-HT$_6$ receptor | % inhibition at 1 micromole |
|---|---|---|
| 1 | 9 | |
| 2 | 34.7 | |
| 3 | 56.7 | |
| 4 | 15 | |
| 5 | 37 | |
| 6 | 24 | |
| 7 | 7 | |
| 8 | 17 | |
| 9 | 28 | |
| 10 | 10.3 | |
| 11 | 39 | |
| 12 | 7 | |
| 13 | 68 | |
| 14 | 5.2 | |
| 15 | 44 | |
| 16 | 29 | |
| 17 | 355 | |
| 18 | 2.3 | |
| 19 | 2.3 | |
| 20 | 9.1 | |
| 21 | 9.4 | |
| 22 | 5.5 | |
| 23 | 18 | |
| 24 | 11 | |
| 25 | 21 | |
| 26 | 18 | |
| 27 | 13 | |
| 28 | 99 | |
| 29 | 1.5 | |
| 30 | 7.5 | |
| 31 | 142 | 75 |
| 32 | 143 | |
| 33 | 207 | |

TABLE 1-continued

| Example No. | Ki (nM) @ 5-HT$_6$ receptor | % inhibition at 1 micromole |
|---|---|---|
| 34 | 216 | |
| 35 | 194 | |
| 36 | 170 | |
| 37 | 47 | |
| 38 | 137 | |
| 39 | | 42 |
| 40 | | 52 |
| 41 | 126 | |
| 42 | | 35 |
| 43 | 73 | |
| 44 | | 69 |
| 45 | | 59 |
| 46 | 107 | |
| 47 | 123 | |
| 48 | | 66 |
| 49 | | 63 |
| 50 | 91.5 | |
| 51 | 191 | |
| 61 | 993 | 44 |
| 62 | | 72 |
| 63 | | 61 |
| 64 | | 57 |
| 65 | | 67 |
| 66 | | 58 |
| 67 | | 77 |
| 68 | 23.5 | |
| 69 | 78 | |
| 70 | 180 | |
| 71 | 116 | |
| 72 | | 66 |
| 73 | | 78 |
| 74 | 72 | |
| 75 | | 69 |
| 76 | | 62 |
| 77 | 14 | |
| 78 | 80 | |
| 79 | 120 | |
| 80 | 13 | |
| 81 | | 74 |
| 82 | | 72 |
| 83 | | 42 |
| 84 | | 73 |
| 85 | 348 | |
| 86 | 41.3 | |
| 87 | 10.5 | |
| 88 | 96.3 | |
| 89 | 150 | |
| 90 | | 78 |
| 91 | 41 | |
| 92 | | 75 |
| 93 | | 71 |
| 94 | | 51 |
| 95 | 118 | |
| 96 | | 75 |
| 97 | 12.3 | |
| 98 | | 76 |
| 99 | | 79 |
| 100 | | 54 |
| 101 | | 55 |
| 102 | | 72 |
| 103 | | 63 |
| 104 | | 69 |
| 105 | | 55 |
| 106 | | 67 |
| 107 | 85 | |
| 108 | 74 | |
| 109 | 10 | |
| Clozapine | 6.0 | |
| Loxapine | 41 | |
| Bromocriptine | 23 | |
| Methiothepin | 8.3 | |
| Mianserin | 44 | |
| Olanzepine | 19.5 | |

TABLE 2

| Example | 5-HT$_6$ Ki (nM) | 5-HT$_6$ % Inhibition @ 1 uM | hNET IC$_{50}$ (nM) | hNET % Inhibition @ 1 uM | 5-HT$_{2A}$ IC$_{50}$ (nM) | 5-HT$_{2A}$ % Inhibition @ 1 uM |
|---|---|---|---|---|---|---|
| 31 | 142 | | 80 | | 459 | |
| 32 | 143 | | 353 | | 1105 | |
| 33 | 207 | | 148 | | 1104 | |
| 34 | 216 | | 302 | | 1078 | |
| 35 | 194 | | 51 | | 645 | |
| 36 | 170 | | 371 | | 458 | |
| 37 | 47 | | 99 | | 600 | |
| 38 | 137 | | 460 | | 31 | |
| 39 | 599 | | 1434 | | 61 | |
| 40 | 354 | | 48 | | 832 | |
| 41 | 126 | | 109 | | 418 | |
| 42 | | 35 | 241 | | | 99 |
| 43 | 73 | | 144 | | 197 | |
| 44 | 434 | | 47 | | 180 | |
| 45 | 767 | | | 28 | | |
| 46 | 107 | | 2397 | | 24 | |
| 47 | 123 | | 311 | | 836 | |
| 48 | 450 | | 430 | | 528 | |
| 49 | 642 | | | 37 | | |
| 50 | 92 | | | 28 | | |
| 51 | 191 | | | 52 | | 94 |
| 52 | | | | 32 | | 16 |
| 53 | | | 126 | | 628 | |
| 54 | | | 485 | | 197 | |
| 55 | | | 121 | | 114 | |
| 56 | | | 139 | | 73 | |
| 57 | | | 1092 | | 72 | |
| 58 | | | 221 | | 90 | |
| 59 | | | 1305 | | | 13 |
| 60 | | | 573 | | | 24 |
| 61 | 993 | | 961 | | 14020 | |
| 110 | | | 11 | | 5979 | |
| 111 | | | 932 | | 7972 | |
| 112 | | | 28 | | 477 | |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

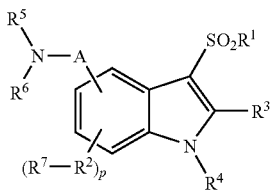

or pharmaceutically acceptable salt thereof, wherein:

A is $C_{2-5}$ alkylene, $C_{2-5}$ alkenylene, or $C_{2-5}$ alkynylene, wherein each is optionally substituted with 1, 2, 3, or 4 independently selected $R^A$ groups;

$R^1$ is aryl optionally substituted by 1, 2, 3, or 4 independently selected $R^{1a}$ groups;

each $R^2$ is, independently, a bond, O, S, C(O), C(O)O, C(O)N($R^{2a}$), OC(O)N($R^{2a}$), S(O), S(O)$_2$, S(O)N($R^{2a}$), S(O)$_2$N($R^{2a}$), or N($R^{2a}$);

$R^3$ is H, $C_{1-6}$ alkyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, cycloalkyl, heterocycloalkyl, aryl, heteroaryl, cycloalkylalkyl, heterocycloalkylalkyl, arylalkyl, or heteroarylalkyl are each optionally substituted by 1, 2, 3, or 4 independently selected $R^{3a}$ groups;

$R^4$ is H, $C_{1-6}$ alkyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, cycloalkyl, heterocycloalkyl, aryl, heteroaryl, cycloalkylalkyl, heterocycloalkylalkyl, arylalkyl, or heteroarylalkyl are each optionally substituted by 1, 2, 3, or 4 independently $R^{4a}$ groups;

$R^5$ is H, $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{5a}$ groups;

$R^6$ is H, $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-10}$ alkyl, $C_{1-10}$ haloalkyl, $C_{2-10}$ alkenyl, $C_{2-10}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups;

each $R^7$ is, independently, H, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl are each optionally substituted by 1, 2, 3, or 4 independently selected $R^{7a}$ groups;

each $R^8$ is, independently, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, OR$^{8b}$, SR$^{8b}$, C(O)R$^{8b}$, C(O)NR$^{8e}$R$^{8f}$, C(O)OR$^{8c}$, OC(O)R$^{8b}$, OC(O)NR$^{8e}$R$^{8f}$, NR$^{8e}$R$^{8f}$, NR$^{8b}$C(O)R$^{8c}$, NR$^{8b}$C(O)OR$^{8c}$, S(O)R$^{8d}$, S(O)NR$^{8e}$R$^{8f}$, S(O)$_2$R$^{8c}$, NR$^{8b}$S(O)$_2$R$^{8c}$, or S(O)$_2$NR$^{8e}$R$^{8f}$, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl are each optionally substituted with 1, 2, 3, or 4 independently selected $R^{8a}$ groups;

each $R^A$ is, independently, halogen, CN, NO$_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, OR$^{Ab}$, SR$^{Ab}$, C(O)R$^{Ab}$, C(O)NR$^{Ae}$R$^{Af}$, C(O)OR$^{Ac}$, OC(O)R$^{Ab}$, OC(O)NR$^{Ae}$R$^{Af}$, NR$^{Ae}$R$^{Af}$, NR$^{Ab}$C(O)R$^{Ac}$, NR$^{Ab}$C(O)OR$^{Ac}$, S(O)R$^{Ad}$, S(O)NR$^{Ae}$R$^{Af}$, S(O)$_2$R$^{Ac}$, NR$^{Ab}$S(O)$_2$R$^{Ac}$, or S(O)$_2$NR$^{Ae}$R$^{Af}$;

each $R^{Ab}$, $R^{Ac}$, $R^{Ae}$, and $R^{Af}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{Ad}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cyofoalkylalkyl, heterocycloalkylalkyl, arylalkyl, or heteroarylalkyl;

or any $R^{Ae}$ and $R^{Af}$, together with the N atom to which they are attached, form a 4-, 5-, 6- or 7-membered heterocycloalkyl group;

each $R^{1a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{1b}$, $SR^{1b}$, $C(O)R^{1b}$, $C(O)NR^{1e}R^{1f}$, $C(O)OR^{1c}$, $OC(O)R^{1b}$, $OC(O)NR^{1e}R^{1f}$, $NR^{1e}R^{1f}$, $NR^{1b}C(O)R^{1c}$, $NR^{1b}C(O)OR^{1c}$, $S(O)R^{1d}$, $S(O)NR^{1e}R^{1f}$, $S(O)_2R^{1c}$, $NR^{1b}S(O)_2R^{1c}$, or $S(O)_2NR^{1e}R^{1f}$;

each $R^{1b}$, $R^{1c}$, $R^{1e}$ and $R^{1f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{1d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{1e}$ and $R^{1f}$, together with the N atom to which they are attached, form a 4-, 5-, 6- or 7-membered heterocycloalkyl group;

each $R^{2a}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl are each optionally substituted with 1, 2, 3, or 4 independently selected $R^{2b}$ groups;

each $R^{2b}$ is, independently, halogen, CN, $NO_2$, OH, $C_{1-6}$ alkyl, $C_{1-6}$ haloalkyl, $C_{1-6}$ alkyloxy, cycloalkyloxy, heterocycloalkyloxy, aryloxy, heteroaryloxy, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{3a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{3b}$, $SR^{3b}$, $C(O)R^{3b}$, $C(O)NR^{3e}R^{3f}$, $C(O)OR^{3c}$, $OC(O)R^{3b}$, $OC(O)NR^{3e}R^{3f}$, $NR^{3e}R^{3f}$, $NR^{3b}C(O)R^{3c}$, $NR^{3b}C(O)OR^{3c}$, $S(O)R^{3d}$, $S(O)N R^{3e}R^{3f}$, $S(O)_2R^{3c}$, $NR^{3b}S(O)_2R^{3c}$, or $S(O)_2NR^{3e}R^{3f}$;

each $R^{3b}$, $R^{3c}$, $R^{3e}$, and $R^{3f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{3d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{3e}$ and $R^{3f}$, together with the N atom to which they are attached, form a 4-, 5-, 6- or 7-membered heterocycloalkyl group;

each $R^{4a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{4b}$, $SR^{4b}$, $C(O)R^{4b}$, $C(O)NR^{4e}R^{4f}$, $C(O)O^{4c}$, $OC(O)R^{4b}$, $OC(O)NR^{4e}R^{4f}$, $NR^{4e}R^{4f}$, $NR^{4b}C(O)R^{4c}$, $NR^{4b}C(O)OR^{4c}$, $S(O)R^{4d}$, $S(O)NR^{4e}R^{4f}$, $S(O)_2R^{4c}$, $NR^{4b}S(O)_2R^{4c}$, or $S(O)_2NR^{4e}R^{4f}$;

each $R^{4b}$, $R^{4c}$, $R^{4e}$, and $R^{4f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{4d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{4e}$ and $R^{4f}$, together with the N atom to which they are attached, form a 4-, 5-, 6- or 7-membered heterocycloalkyl group;

each $R^{5a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{5b}$, $SR^{5b}$, $C(O)R^{5b}$, $C(O)NR^{5e}R^{5f}$, $C(O)OR^{5c}$, $OC(O)R^{5b}$, $OC(O)NR^{5e}R^{5f}$, $NR^{5e}R^{5f}$, $NR^{5b}C(O)R^{5c}$, $NR^{5b}C(O)OR^{5c}$, $S(O)R^{5d}$, $S(O)NR^{5e}R^{5f}$, $S(O)_2R^{5c}$, $NR^{5b}S(O)_2R^{5c}$, or $S(O)_2NR^{5e}R^{5f}$;

each $R^{5b}$, $R^{5c}$, $R^{5e}$, and $R^{5f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{1-6}$ haloalkyl, $C_{2-6}$ alkenyl, $C_{2-6}$ alkynyl, cycloalkyl, heterocycloalkyt, aryl, heteroaryl, cycloalkylalkyl, heterocycloalkylalkyl, arylalkyl, and heteroarylalkyl is optionally substituted with 1, 2, 3, or 4 independently selected $R^{5'}$ groups;

each $R^{5d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein each is optionally substituted with 1, 2, 3, or 4 independently selected $R^{5'}$ groups;

or any $R^{5e}$ and $R^{5f}$, together with the N atom to which they are attached, form a 4-, 5-, 6- or 7-membered heterocycloalkyl group;

each $R^{6a}$ is, independently, halogen, CN, $NO_2$, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, heteroarylalkyl, $OR^{6b}$, $SR^{6b}$, $C(O)R^{6b}$, $C(O)NR^{6e}R^{6f}$, $C(O)OR^{6c}$, $OC(O)R^{6b}$, $OC(O)NR^{6e}R^{6f}$, $NR^{6e}R^{6f}$, $NR^{6b}C(O)R^{6c}$, $NR^{6b}C(O)OR^{6c}$, $S(O)R^{6d}$, $S(O)NR^{6e}R^{6f}$, $S(O)_2R^{6c}$, $NR^{6b}S(O)_2R^{6c}$, or $S(O)_2NR^{6e}R^{6f}$, each $R^{6b}$, $R^{6c}$, $R^{6e}$, and $R^{6f}$ is, independently, H, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein said $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, and heteroarylalkyl is optionally substituted with 1, 2, 3, or 4 independently selected $R^{6'}$ groups;

each $R^{6d}$ is, independently, $C_{1-6}$ alkyl, $C_{1-6}$ haloalkyl, $C_{2-6}$ alkenyl, $C_{2-6}$ alkynyl, cycloalkyl, heterocycloalkyl, aryl, heteroaryl, cycloalkylalkyl, heterocycloalkylalkyl, arylalkyl, or heteroarylalkyl, wherein each is optionally substituted with 1, 2, 3, or 4 independently selected $R^{6'}$ groups;

or any $R^{6e}$ and $R^{6f}$, together with the N atom to which they are attached, form a 4-, 5-, 6-or 7-membered heterocycloalkyl group;

each $R^{5'}$ and $R^{6'}$ is, independently, halogen, CN, NO$_2$, C$_{1-6}$ alkyl, C$_{2-6}$ alkenyl, C$_{2-6}$ alkynyl, C$_{1-6}$ haloalkyl, C$_{1-6}$ alkyloxy, cycloalkyloxy, heterocycloalkyloxy, aryloxy, heteroaryloxy, cycloalkyl, heterocycloalkyl, aryl, heteroaryl, cycloalkylalkyl, heterocycloalkylalkyl, arylalkyl, or heteroarylalkyl;

each $R^{7a}$ is, independently, halogen, CN, NO$_2$, C$_{1-6}$alkyl, C$_{1-6}$haloalkyl, C$_{2-6}$alkenyl, C$_{2-6}$alkynyl, cycloalkyl, heterocycloalkyl, aryl, heteroaryl, cycloalkylalkyl, heterocycloalkylalkyl, arylalkyl, heteroarylalkyl, OR$^{7b}$, SR$^{7b}$, C(O)R$^{7b}$, C(O)NR$^{7e}$R$^{7f}$, C(O)OR$^{7c}$, OC(O)R$^{7b}$, OC(O)NR$^{7e}$R$^{7f}$, NR$^{7e}$R$^{7f}$, NR$^{7b}$C(O)R$^{7c}$, NR$^{7b}$C(O)OR$^{7c}$, S(O)R$^{7d}$, S(O)NR$^{7e}$R$^{7f}$, S(O)$_2$R$^{7c}$, NR$^{7b}$S(O)$_2$R$^{7c}$, or S(O)$_2$NR$^{7e}$R$^{7f}$;

each $R^{7b}$, $R^{7c}$, $R^{7e}$, and $R^{7f}$ is, independently, H, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{7d}$ is, independently, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{7e}$ and $R^{7f}$, together with the N atom to which they are attached, form a 4-, 5-, 6- or 7-membered heterocycloalkyl group;

each $R^{8a}$ is, independently, halogen, CN, NO$_2$, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, heteroarylalkyl, OR$^{8b'}$, SR$^{8b'}$, C(O)R$^{8b'}$, CO(O)NR$^{8e'}$R$^{8f'}$, C(O)OR$^{8c'}$, OC(O)R$^{8b'}$, OC(O)NR$^{8e'}$R$^{8f'}$, NR$^{8e'}$R$^{8f'}$, NR$^{8b'}$C(O)R$^{8c'}$, NR$^{8b'}$C(O)OR$^{8c'}$, S(O)R$^{8d'}$, S(O)NR$^{8e'}$R$^{8f'}$, S(O)$_2$R$^{8c'}$, NR$^{8b'}$S(O)$_2$R$^{8c'}$, or S(O)$_2$NR$^{8e'}$R$^{8f'}$;

each $R^{8b}$, $R^{8c}$, $R^{8e}$, and $R^{8f}$ is, independently, H, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8d}$ is, independently, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8b'}$, $R^{8c'}$, $R^{8e'}$, and $R^{8f'}$ is, independently, H, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, or heteroarylalkyl;

each $R^{8d'}$ is, independently, C$_{1-6}$ alkyl, C$_{1-6}$ haloalkyl, C$_{2-6}$ alkenyl, C$_{2-6}$ alkynyl, cycloalkyl, heterocycloalkyl, aryl, heteroaryl, cycloalkylalkyl, heterocycloalkylalkyl, arylalkyl, or heteroarylalkyl;

or any $R^{8e'}$ and $R^{8f'}$, together with the N atom to which they are attached, form a 4-, 5-, 6- or 7-membered heterocycloalkyl group; and p is 0, 1, 2, or 3;

with the proviso that if $R^7$ is halogen, CN, or NO$_2$, then $R^2$ is a bond.

2. The compound of claim 1 wherein A is C$_{2-5}$ alkylene.

3. The compound of claim 1 wherein A is ethan-1,2-diyl or propan-1,3-diyl.

4. The compound of claim 1 wherein $R^1$ is aryl substituted with 1, 2, 3, or 4 independently selected $R^{1a}$ groups.

5. The compound of claim 1 wherein $R^1$ is phenyl substituted with 1, 2, 3, or 4 independently selected $R^{1a}$ groups.

6. The compound of claim 1 wherein $R^1$ is phenyl or 3-fluorophenyl.

7. The compound of claim 1 wherein $R^1$ is phenyl.

8. The compound of claim 1 wherein each $R^2$ is, independently, a bond.

9. The compound of claim 1 wherein $R^3$ is H, C$_{1-6}$ alkyl, or aryl.

10. The compound of claim 1 wherein $R^3$ is H, methyl, ethyl, or phenyl.

11. The compound of claim 1 wherein $R^4$ is H.

12. The compound of claim 1 wherein:

$R^5$ is H, C$_{1-10}$ alkyl, cycloalkyl, heterocycloalkylalkyl, or arylalkyl, wherein said C$_{1-10}$ alkyl is substituted with 1, 2, 3, or 4 independently selected $R^{5a}$ groups; and $R^6$ is H, C$_{1-10}$ alkyl, cycloalkyl, heterocycloalkylalkyl, or arylalkyl, wherein said C$_{1-10}$ alkyl is substituted with 1, 2, 3, or 4 independently selected $R^{6a}$ groups.

13. The compound of claim 1 wherein $R^5$ and $R^6$ are each, independently, H, methyl, ethyl, propyl, isopropyl, isobutyl, pentan-3-yl, 1,2,2-trimethylpropyl, 2,2-dimethylpropyl, 2-methyl-1-butyl, 2-hydroxyethyl, dimethylaminopropyl, cyclopropyl, cyclobutyl, cyclopentyl, cyclohexyl, benzyl, or (tetrahydrofur-2-yl)methyl.

14. The compound of claim 1 wherein $R^5$ and $R^6$, together with the N atom to which they are attached, form a 3-, 4-, 5-, 6-, 7- or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups.

15. The compound of claim 1 wherein $R^5$ and $R^6$, together with the N atom to which they are attached, form a 3-, 4-, 5-, 6-, 7-, or 8-membered heterocycloalkyl ring, wherein said heterocycloalkyl ring is optionally substituted with 1, 2, 3, or 4 independently selected $R^8$ groups.

16. The compound of claim 1 wherein $R^5$ and $R^6$, together with the N atom to which they are attached, form a pyrrolidin-1-yl, piperidin-1-yl, morpholin-4-yl, piperazin-1-yl, 2-methylpiperidin-1-yl, 3-methylpiperidin-1-yl, 2,6-dimethylpiperidin-1-yl, 2-methylpyrrolidin-1-yl, azepan-1-yl, 4-methylpiperazin-1-yl, or azetidin-1-yl ring.

17. The compound of claim 1 wherein each $R^7$ is H.

18. The compound of claim 1 wherein:

A is C$_{2-5}$ alkylene which is optionally substituted with 1, 2, 3, or 4 independently selected $R^4$ groups;

each $R^2$ is, independently, a bond;

$R^3$ is H, C$_{1-6}$ alkyl, cycloalkyl, aryl, or heteroaryl, wherein said C$_{1-6}$ alkyl, cycloalkyl, aryl, and heteroaryl are each optionally substituted by 1, 2, 3, or 4 independently selected $R^{3a}$ groups;

$R^4$ is H, C$_{1-6}$ alkyl, cycloalkyl, aryl, or heteroaryl, wherein said C$_{1-6}$ alkyl, cycloalkyl, aryl, and heteroaryl are each optionally substituted by 1, 2, 3, or 4 independently selected $R^{4a}$ groups;

$R^5$ is H, C$_{1-10}$ alkyl, cycloalkyl, aryl, heterocycloalkylalkyl, or arylalkyl, wherein said C$_{1-10}$ alkyl, cycloalkyl, heterocycloalkylalkyl, and arylalkyl are each optionally substituted with 1, 2, 3, or 4 independently selected $R^{5a}$ groups;

$R^6$ is H, C$_{1-10}$ alkyl, cycloalkyl, aryl, heterocycloalkylalkyl, or arylalkyl, wherein said C$_{1-10}$ alkyl, cycloalkyl, heterocycloalkylalkyl, and arylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring or 5-, 6-, 7- or 8-membered heteroaryl ring, wherein said heterocycloalkyl ring and said heteroaryl ring are each optionally substituted with 1, 2, 3, or 4 independently selected $R^8$ groups; and each $R^7$ is, independently, H, halogen, $C_{1-6}$ alkyl, cycloalkyl, aryl, or heteroaryl, wherein said $C_{1-6}$ alkyl, cycloalkyl, aryl, and heteroaryl are each optionally substituted by 1, 2, 3, or 4 independently selected $R^{7a}$ groups.

19. The compound of claim 1 wherein:

A is $C_{2-5}$ alkylene;

$R^1$ is aryl, which is optionally substituted by 1, 2, 3, or 4 independently selected $R^{1a}$ groups;

each $R^2$ is, independently, a bond;

$R^3$ is H, $C_{1-6}$ alkyl, or aryl, wherein said $C_{1-6}$ alkyl and aryl are each optionally substituted by 1, 2, 3, or 4 independently selected $R^{3a}$ groups;

$R^4$ is H;

$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{5a}$ groups;

$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring, wherein said heterocycloalkyl ring is optionally substituted with 1, 2, 3, or 4 independently selected $R^8$ groups; and each $R^7$ is, independently, H.

20. The compound of claim 1 wherein:

A is ethan-1,2-diyl or propan-1,3-diyl;

$R^1$ is phenyl, which is optionally substituted by 1, 2, 3, or 4 independently selected $R^{1a}$ groups;

each $R^2$ is, independently, a bond;

$R^3$ is H, $C_{1-6}$ alkyl, or phenyl;

$R^4$ is H;

$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{5a}$ groups;

$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring, wherein said heterocycloalkyl ring is optionally substituted with 1, 2, 3, or 4 independently selected $R^8$ groups;

each $R^7$ is, independently, H;

each $R^{1a}$ is, independently, halogen;

each $R^{5a}$ is, independently, $OR^{5b}$ or $NR^{5e}R^{5f}$;

each $R^{6a}$ is, independently, $OR^{6b}$ or $NR^{6e}R^{6f}$;

each $R^8$ is, independently, $C_{1-6}$ alkyl.

21. The compound of claim 1 wherein:

A is ethan-1,2-diyl or propan-1,3-diyl;

$R^1$ is phenyl, which is optionally substituted by 1, 2, 3, or 4 independently selected $R^{1a}$ groups;

each $R^2$ is, independently, a bond;

$R^3$ is H, methyl, ethyl, or phenyl;

$R^4$ is H;

$R^5$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{5a}$ groups;

$R^6$ is H, $C_{1-10}$ alkyl, cycloalkyl, aryl, heterocycloalkylalkyl, or arylalkyl, wherein said $C_{1-10}$ alkyl, cycloalkyl, heterocycloalkylalkyl, and arylalkyl are each optionally substituted with 1, 2, 3, or 4 independently selected $R^{6a}$ groups;

or $R^5$ and $R^6$, together with the N atom to which they are attached, form a 3-, 4-, 5-, 6- 7- or 8-membered heterocycloalkyl ring, wherein said heterocycloalkyl ring is optionally substituted with 1, 2, 3, or 4 independently selected $R^8$ groups;

each $R^7$ is, independently, H;

each $R^{1a}$ is, independently, F;

each $R^{5a}$ is, independently, OH or $N(CH_3)_2$;

each $R^{6a}$ is, independently, OH or $N(CH_3)_2$;

each $R^8$ is, independently, methyl; and p is 0 or 1.

22. The compound of claim 1 wherein:

A is ethan-1,2-diyl or propan-1,3-diyl;

$R^1$ is phenyl or 3-fluorophenyl;

$R^3$ is H, methyl, ethyl or phenyl;

$R^4$ is H $R^5$ is H, methyl, ethyl, propyl, isopropyl, isobutyl, pentan-3-yl, 1,2,2-trimethylpropyl, 2,2-dimethylpropyl, 2-methyl-1-butyl, cyclopropyl, cyclobutyl, cyclopentyl, cyclohexyl, benzyl, or (tetrahydrofur-2-yl)methyl, wherein said ethyl is optionally substituted with 1 $R^{5a}$;

$R^6$ is H, methyl, ethyl, propyl, isopropyl, isobutyl, pentan-3-yl, 1,2,2-trimethylpropyl, 2,2-dimethylpropyl, 2-methyl-1-butyl, cyclopropyl, cyclobutyl, cyclopentyl, cyclohexyl, benzyl, or (tetrahydrofur-2-yl)methyl, wherein said propyl is optionally substituted with 1 $R^{6a}$;

or $R^5$ and $R^6$, together with the N atom to which they are attached, form a pyrrolidin-1-yl, piperidin-1-yl, morpholin-4-yl, piperazin-1-yl, 2-methylpiperidin-1-yl, 3-methylpiperidin-1-yl, 2,6-dimethyipiperidin-1-yl, 2-methylpyrrolidin-1-yl, azepan-1-yl, 4-methylpiperazin-1-yl, or azetidin-1-yl ring;

each $R^{5a}$ is, independently, OH;

each $R^{6a}$ is, independently, $N(CH_3)_2$; and p is 0.

23. The compound of claim 1 wherein:

A is ethan-1,2-diyl or propan-1,3-diyl;

$R^1$ is phenyl or 3-fluorophenyl;

$R^3$ is H, methyl, ethyl or phenyl;

$R^4$ is H $R^5$ is H, methyl, ethyl, propyl, isopropyl, isobutyl, pentan-3-yl, 1,2,2-trimethylpropyl, 2,2-dimethylpropyl, 2-methyl-1-butyl, 2-hydroxyethyl, dimethylaminopropyl, cyclopropyl, cyclobutyl, cyclopentyl, cyclohexyl, benzyl, or (tetrahydrofur-2-yl) methyl, $R^6$ is H, methyl, ethyl, propyl, isopropyl, isobutyl, pentan-3-yl, 1,2,2-trimethylpropyl, 2,2-dimethylpropyl, 2-methyl-1-butyl, 2-hydroxyethyl, dimethylaminopropyl, cyclopropyl, cyclobutyl, cyclopentyl, cyclohexyl, benzyl, or (tetrahydrofur-2-yl)methyl.

or $R^5$ and $R^6$, together with the N atom to which they are attached, form a pyrrolidin-1-yl, piperidin-1-yl, morpholin-4-yl, piperazin-1-yl, 2-methylpiperidin-1-yl, 3-methylpiperidin-1-yl, 2,6-dimethylpiperidin-1-yl, 2-methylpyrrolidin-1-yl, azepan-1-yl, 4-methylpiperazin-1-yl or azetidin-1-yl ring; and p is 0.

24. The compound of claim 1 having Formula I-A:

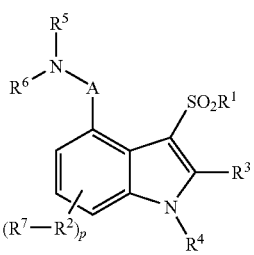

or pharmaceutically acceptable salt thereof.

25. The compound of claim 1 having Formula I-B:

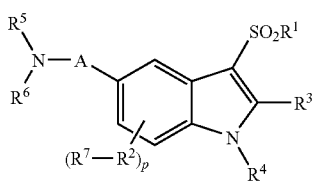

or pharmaceutically acceptable salt thereof.

26. The compound of claim 1 having Formula I-C:

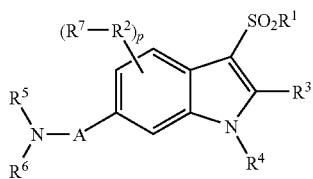

or pharmaceutically acceptable salt thereof.

27. The compound of claim 1 having Formula I-D:

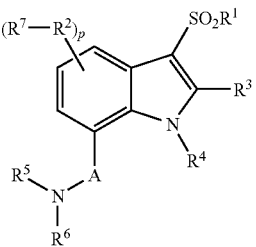

or pharmaceutically acceptable salt thereof.

28. The compound of claim 1 which is:
N,N-dimethyl-N-{2-[3-(phenylsulfonyl)-1H-indol-5-yl]ethyl}amine;
N{2-[3-(phenylsulfonyl)-1H-indol-5-yl]ethyl}-N-propylamine;
N{2-[3-(phenylsulfonyl)-1H-indol-5-yl]ethyl}propan-2-amine;
N{2-[3-(phenylsulfonyl)-1H-indol-5-yl]ethyl}cyclopropanamine;
N{2-[3-(phenylsulfonyl)-1H-indol-5-yl]ethyl}cyclopentanamine;
N-benzyl-N-{2[3-(phenlylsulfonyl)-1H-indol-5-yl]ethyl}amine;
N-ethyl-N-methyl-N-{2-[3-(phenylsulfonyl)-1H-indol-5-yl]ethyl}amine;
N,N-diethyl-N-{2-[3-(phenylsulfonyl)-1H-indol-5-yl]ethyl}amine;
3-(phenylsulfonyl)-5-(2-pyrrolidin-1-ylethyl)-1H-indole;
3-(phenylsulfonyl)-5-(2-piperidin-1-ylethyl)-1H-indole;
5-(2-morpholin-4-ylethyl)-3-(phenylsulfonyl)-1H-indole;
{2-[3-(phenylsulfonyl)-1H-indol-5-yl]ethyl}amine;
3-(phenylsulfonyl)-5-(2-piperazin-1-ylethyl)-1H-indole;
N-methyl-N-{2[3-(phenylsulfonyl)-1H-indol-5-yl]ethyl}amine;
N-methyl-N-{2[2-methyl-3-phenysulfonyl-1H-indol-5-yl]ethyl}amine;
N-{2-[2-ethyl-3-(phenylsulfonyl)-1-H-indol-5-yl]ethyl}-N-methylamine;
N-methyl-N-{2-[2-phenyl-3-(phenylsulfonyl)-1H-indol-5-yl]ethyl}amine;
N,N-dimethyl-N-{2-[3-(phenylsulfonyl)-1H-indol-7-yl]ethyl}amine;
N-methyl-N-{2-[3-(phenylsulfonyl)-1H-indol-7-yl]ethyl}amine;
N-{2-[3-(phenylsulfonyl)-1H-indol-7-yl]ethyl}-N-propylamine;
N-{2-[3-(phenylsulfonyl)-1H-indol-7-yl]ethyl}propan-2-amine;
N-{2-[3-(phenylsulfonyl)-1H-indol-7-yl]ethyl}cyclopropanamine;
N-{2-[3-(phenylsulfonyl)-1H-indol-7-yl]ethyl}cyclopentanamine;
N-ethyl-N-methyl-N-{2-[3-(phenylsulfonyl)-1H-indol-7-yl]ethyl}amine;
N,N-diethyl-N-{2-[3-(phenylsulfonyl)-1H-indol-7-yl]ethyl}amine;
3-(phenylsulfonyl)-7-(2-pyrrolidin-1-ylethyl)-1H-indole;
3-(phenylsulfonyl)-7-(2-piperidin-1-ylethyl)-1H-indole;
7-(2-morpholin-4-ylethyl)-3-(phenylsulfonyl)-1H-indole;
{2-[3-(phenylsulfonyl)-1H-indol-7-yl]ethyl}amine;
3-(phenylsulfonyl)-7-(2-piperazin-1-ylethyl)-1H-indole;
N,N-dimethyl-N-{2-[3-(phenylsulfonyl)-1H-indol-4-yl]ethyl}amine;
N-methyl-N-{2-[3-(phenylsulfonyl)-1H-indol-4-yl]ethyl}amine;
N-ethyl-N-{2-[3-(phenylsulfonyl)-1H-indol-4-yl]ethyl}amine;
N-{2-[3-(phenylsulfonyl)-1H-indol-4-yl]ethyl}-N-propylamine;
N-{2-[3-(phenylsulfonyl)-1H-indol-4-yl]ethyl}propan-2-amine;
N-{2-[3-(phenylsulfonyl)-1H-indol-4-yl]ethyl}cyclopropanamine;
N-{2-[3-(phenylsulfonyl)-1H-indol-4-yl]ethyl}cyclobutanamine;
N-{2-[3-(phenylsulfonyl)-1H-indol-4-yl]ethyl}cyclopentanamine;
N-{2-[3-(phenylsulfonyl)-1H-indol-4-yl]ethyl}cyclohexanamine;
N-ethyl-N-methyl-N-{2-[3-(phenylsulfonylyl)-1H-indol-4-yl]ethyl}amine;
N-cyclohexyl-N-methyl-N-{2-[3-(phenylsulfonyl)-1H-indol-4-yl]ethyl}amine;
N,N-diethyl-N-{2-[3-(phenylsulfonyl)-1H-indol-4-yl]ethyl}amine;
3-(phenylsulfonyl)-4-(2-pyrrolidin1-ylethyl)-1H-indole;

3-(phenylsulfonyl)-4-(2-piperidin-1-ylethyl)-1H-indole;
4-(2-morpholin-4-ylethyl)-3-(phenylsulfonyl)-1H-indole;
N-{2-[3-(phenylsulfonyl)-1H-indol-4-yl]ethyl}-N-(1,2,2-trimethylpropyl)amine;
N-benzyl-N-{2-[3-(phenylsulfonyl)1H-indol-4-yl]ethyl}amine;
N-isobutyl-N-{2-[3-(phenylsulfonyl)1H-indo-4-yl]ethyl}amine;
N-(2,2-dimethylpropyl)-N-{2-[3-(phenylsulfonyl)1H-indo-4-yl]ethyl}amine;
N,N-dimethyl-N'-{2-[3-(phenylsulfonyl)1H-indol-4-yl]ethyl}propane-1,3-diamine;
N-{2-[3-(phenylsulfonyl)-1H-indol-4-yl]ethyl}-N-((tetrahydrofur-2-yl)methyl)amine;
4-{2-[(2R*,6S*)-2,6-dimethylpiperidin-1-yl]ethyl}-3-(phenylsulfonyl)-1H-indole;
N-methyl-N-{2-[3-(phenylsulfonyl)-1H-indole-4-yl]ethyl}propan-2-amine;
N-ethyl-N-{2-[3-(phenylsulfonyl)-1H-indole-4-yl]ethyl}propan-2-amine;
4-[2-(2-methylpyrrolidin-1-yl)ethyl]-3-(phenylsulfonyl)-1H-indole;
4-[2-(2-methylpiperidin-1-yl)ethyl]-3-(phenylsulfonyl)-1H-indole;
4-[2-(3-methylpiperidin-1-yl)ethyl]-3-(phenylsulfonyl)-1H-indole;
4-(2-azepan-1-ylethyl)-3-(phenylsulfonyl)-1H-indole;
4-[2(4-methylpiperazin-1-yl]ethyl-3-(phenylsulfonyl)-1H-indole;
3-(phenylsulfonyl)-4-(2-piperazin-1-ylethyl)-1H-indole;
{2-[3-(phenylsulfonyl)-1H-indol-4-yl]ethyl}amine;
N-methyl-N-{2-[3-(3-fluorophenylsulfonyl)-1H-indol-4-yl]ethyl}amine;
N-ethyl-N-{2-[3-(3-fluorophenylsulfonyl)-1H-indol-4-yl]ethyl}amine;
N,N-dimethyl-N-{2-[3-(3-fluorophenylsulfonyl)-1H-indol-4-yl]ethyl}amine;
N-{2-[3-(3-fluorophenylsulfonyl)-1H-indol-4-yl]ethyl}-N-propylamine;
N-{2-[3-(3-fluorophenylsulfonyl)-1H-indol-4-yl]ethyl}propan-2-amine;
N-{2-[3-(3-fluorophenylsulfonyl)-1H-indol-4-yl]ethyl}cyclopropanamine;
N-{2-[3-(3-fluorophenylsulfonyl)-1H-indol-4-yl]ethyl}cyclobutanamine;
N-{2-[3-(3-fluorophenylsulfonyl)-1H-indol-4-yl]ethyl}cyclopentanamine;
N-{2-[3-(3-fluorophenylsulfonyl)-1H-indol-4-yl]ethyl}cyclohexanamine;
N-ethyl-N-methyl-N-{2-[3-(3-fluorophenylsulfonyl)-1H-indol-4-yl]ethyl}amine;
N-cyclohexyl-N-methyl-N-{2-[3-(3-fluorophenylsulfonyl)-1H-indol-4-yl]ethyl}amine;
N,N-diethyl-N-{2-[3-(3-fluorophenylsulfonyl)-1H-indol-4-yl]ethyl}amine;
3-(3-fluorophenylsulfonyl)-4-(2-pyrrolidin-1-ylethyl)-1H-indole;
3-(3-fluorophenylsulfonyl)-4-(2-piperidin-1-ylethyl)-1H-indole;
4-(2-morpholin-4-ylethyl)-3-(3-fluorophenylsulfonyl)-1H-indole;
N-isobutyl-N-{2-[3-(3-fluorophenylsulfonyl)-1H-indol-4-yl]ethyl}amine;
(1-Ethyl-propyl)-{2-[3-(3-fluorophenylsulfonyl)-1H-indol-4-yl]-ethyl}-amine;
{2-[3-(3-Fluorophenylsulfonyl)-1-indol-4-yl]-ethyl}-(2-methyl-butyl)-amine;
N-{2-[3-(3-fluorophenylsulfonyl)-1H-indol-4-yl]-ethyl}-N-(1,2,2-trimethylpropyl)amine;
N-(2,2-dimethylpropyl)-N-{2-[3-(3-fluorophenylsulfonyl)-1H-indol-4-yl]ethyl}amine;
N-{2-[3-(3fluorophenylsulfonyl)-1H-indol-4-yl]ethyl}-N-((tetrahydrofur-2-yl)methyl)amine;
N'-{2-[3-(3-Fluorophenylsulfonyl)-1H-indol-4-yl]-ethyl}-N,N-dimethyl-propane-1,3-diamine;
2-({2-[3-(3-Fluorophenylsulfonyl)-1H-indol-4-yl]1-ethyl}-methyl-amino)-ethanol;
{2-[3-(3-fluorophenylsulfonyl)-1H-indol-6-yl]ethyl}amine;
N,N-dimethyl-N-{2-[3-(phenylsulfonyl)-1H-indol-6-yl]ethyl}amine;
N-methyl-N-{2-[3-(phenylsulfonyl)-1H-indol-6-yl]ethyl}amine;
N-ethyl-N-{2-[3-(phenylsulfonyl)-1H-indol-6-yl]ethyl}amine;
N-{2-[3-(phenylsulfonyl)-1H-indol-6-yl]ethyl}-N-propylamine;
N-{2-[3-(phenylsulfonyl)-1H-indol-6-yl]ethyl}propan-2-amine;
N-{2-[3-(phenylsulfonyl)-1H-indol-6-yl]ethyl}cyclopropanamine;
N-{2-[3-(phenylsulfonyl)-1H-indol-6-yl]ethyl}cyclobutanamine;
N-{2-[3-(phenylsulfonyl)-1H-indol-6-yl]ethyl}cyclopentanamine;
N-{2-[3-(phenylsulfonyl)-1H-indol-6-yl]ethyl)}cyclohexanamine;
N-ethyl-N-methyl-N-{2-[3-(phenylsulfonyl)-1H-indol-6-yl]ethyl}amine;
N-cyclohexyl-N-methyl-N-{2-[3-(phenylsulfonyl)-1H-indol-6-yl]ethyl}amine;
N,N-diethyl-N-{2-[3-(phenylsulfonyl)-1H-indol-6-yl]ethyl}amine;
3-(phenylsulfonyl)-6-(2-pyrrolidin-1-ylethyl)-1H-indole;
3-(phenylsulfonyl)-6-(2-piperidin-1-ylethyl)-1H-indole;
4-(2-morpholin-6-ylethyl)-3-(phenylsulfonyl)-1H-indole;
3-phenylsulfonyl-6-(2-piperazin-1-yl-ethyl)-1H-indole;
N-isobutyl-N-{2-[3-(phenylsulfonyl)-1H-indol-6-yl]ethyl}amine;
(1-Ethyl-propyl)-{2-[3-(phenylsulfonyl)-1H-indol-6-yl]-ethyl}-amine;
{2-[3-(phenylsulfonyl)-1H-indol-6-yl]-ethyl}-(2-methyl-butyl)-amine;
N-{2-[3-(phenylsulfonyl)-1H-indol-6-yl]ethyl}-N-(1,2,2-trimethylpropyl)amine;
N-(2,2-dimethylpropyl)-N-{2-[3-(phenylsulfonyl)-1H-indol-6-yl]ethyl}amine;
N-{2-[3-(phenylsulfonyl)-1H-indol-6-yl]ethyl}-N-((tetrahydrofur-2-yl)methyl)amine;
6-(2-Azetidin-1-yl-ethyl)-3-phenylsulfonyl-1H-indole;
{2-[3-(phenylsulfonyl)-1H-indol-6-yl]ethyl}amine;
N-isopropyl-3-[3-(phenylsulfonyl)-1H-indol-4-yl]propan-1-amine;
3-(phenylsulfonyl)-4-(3-piperidin-1-ylpropyl)-1H-indole; or
N-ethyl-N-methyl-3-[3-(phenylsulfonyl)-1H-indol-4-yl]propan-1-amine;
or pharmaceutically acceptable salt thereof.

29. A pharmaceutical composition comprising a pharmaceutically acceptable carrier and a compound of claim 1, or pharmaceutically acceptable salt thereof.

* * * * *

UNITED STATES PATENT AND TRADEMARK OFFICE
CERTIFICATE OF CORRECTION

PATENT NO.         : 7,645,752 B2                                                Page 1 of 1
APPLICATION NO. : 11/622649
DATED              : January 12, 2010
INVENTOR(S)        : McDevitt et al.

It is certified that error appears in the above-identified patent and that said Letters Patent is hereby corrected as shown below:

Column 93, line 5, please replace the term "cyofoalkylalkyl" with "cycloalkylalkyl".

Column 94, line 28, please replace the term "heterocycloalkyt" with "heterocycloalkyl".

Signed and Sealed this

Twentieth Day of April, 2010

David J. Kappos
*Director of the United States Patent and Trademark Office*